US008592389B2

(12) United States Patent
Thum et al.

(10) Patent No.: US 8,592,389 B2
(45) Date of Patent: *Nov. 26, 2013

(54) MICRORNA (MIRNA) AND DOWNSTREAM TARGETS FOR DIAGNOSTIC AND THERAPEUTIC PURPOSES

(75) Inventors: Thomas Thum, Hannover (DE); Johann Bauersachs, Wurzburg (DE); Stefan Engelhardt, Munich (DE); Carina Gross, Wolfstein (DE)

(73) Assignee: Julius-Maximilians-Universitat Wurzburg, Wurzburg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/535,652

(22) Filed: Jun. 28, 2012

(65) Prior Publication Data

US 2013/0018084 A1    Jan. 17, 2013

Related U.S. Application Data

(63) Continuation of application No. 12/919,592, filed as application No. PCT/EP2009/001590 on Feb. 26, 2009, now Pat. No. 8,236,777.

(60) Provisional application No. 61/033,340, filed on Mar. 3, 2008, provisional application No. 61/031,835, filed on Feb. 27, 2008.

(30) Foreign Application Priority Data

Feb. 27, 2008  (EP) .................................... 08003570
Feb. 19, 2009  (WO) ................. PCT/EP2009/051986

(51) Int. Cl.
    *A61K 48/00*    (2006.01)
    *C07H 21/04*    (2006.01)
    *C07H 21/02*    (2006.01)

(52) U.S. Cl.
    USPC ...... 514/44; 536/23.1; 536/24.31; 536/24.33; 536/24.5

(58) Field of Classification Search
    None
    See application file for complete search history.

(56) References Cited

U.S. PATENT DOCUMENTS

| 2007/0213292 A1 | 9/2007 | Stoffel et al. |
| 2009/0192102 A1 | 7/2009 | Bader et al. |
| 2010/0010073 A1 | 1/2010 | Thum et al. |

FOREIGN PATENT DOCUMENTS

| JP | 2006-520760 A | 9/2006 |
| WO | 2004083430 A2 | 9/2004 |
| WO | 2006/053014 A2 | 5/2006 |
| WO | 2007/112754 A2 | 10/2007 |
| WO | 2008/043521 A2 | 4/2008 |
| WO | 2009/058818 A2 | 5/2009 |

OTHER PUBLICATIONS

Ambros, "The functions of animal microRNAs," Nature. Sep. 16, 2004;431(7006):350-5.
Buitrago et al., "The transcriptional repressor Nab1 is a specific regulator of pathological cardiac hypertrophy," Nat Med. Aug. 2005;11(8):837-44.
Cai et al., "Human microRNAs are processed from capped, polyadenylated transcripts that can also function as mRNAs," RNA (2004) 10: 1957-1966.
Care et al., "MicroRNA-133 controls cardiac hypertrophy," Nat Med., 2007;13:613-18.
Casci et al., "Sprouty, an intracellular inhibitor of Ras signaling," Cell. Mar. 5, 1999;96(5):655-65.
Castoldi et al., "A sensitive array for microRNA expression profiling (miChip) based on locked nucleic acids (LNA)," RNA. May 2006;12(5):913-20.
Chan et al., "MicroRNA-21 is an Antiapoptotic Factor in Human Glioblastoma Cells," Canc. Res. Jul. 15, 2005; 65 (14): 6029-6033.
Cheng et al.., "Antisense inhibition of human miRNAs and indications for an involvement of miRNA in cell growth and apoptosis," Nucl. Acids Res. Mar. 1, 2005; 33(4):1290-1297.
Cheng et al., "MicroRNAs are aberrantly expressed in hypertrophic heart: do they play a role in cardiac hypertrophy?," Am J Pathol. Jun. 2007;170(6):1831-40.
Collins et al., "Accuracy of echocardiographic estimates of left ventricular mass in mice," Am J Physiol Heart Circ Physiol. May 2001;280(5):H1954-62.
Engelhardt et al., "Progressive hypertrophy and heart failure in beta1-adrenergic receptor transgenic mice," Proc Natl Acad Sci USA. Jun. 8, 1999;96(12):7059-64.
Griffiths-Jones et al., "miRBase: microRNA sequences, targets and gene nomenclature," Nucleic Acids Res. Jan. 1, 2006;34(Database issue):D140-4.
Hanafusa et al., "Sprouty1 and Sprouty2 provide a control mechanism for the Ras/MAPK signalling pathway," Nat Cell Biol. Nov. 2002;4(11):850-8.
Iorio et al., "MicroRNA gene expression deregulation in human breast cancer," Cancer Res. Aug. 15, 2005;65 (16):7065-70.
Krutzfeldt et al., "Silencing of microRNAs in vivo with 'antagomirs'," Nature 2005;438:685-89.

(Continued)

*Primary Examiner* — Amy Bowman
(74) *Attorney, Agent, or Firm* — Casimir Jones, S.C.

(57) ABSTRACT

In some embodiments, the present invention concerns antisense oligonucleotides against targets of miR-21. In some embodiments, the invention is directed to a method for diagnosing fibrosis and/or fibrosis related diseases and to a method for screening a pharmaceutically active compound for the treatment of fibrosis and/or fibrosis related diseases. The present invention further relates to compositions for use in the treatment, amelioration, and/or prevention of fibrosis. In certain embodiments, the compositions modulate the activity of a miRNA for the treatment, amelioration, and/or prevention of fibrosis. In certain embodiments, the compositions inhibit the activity of miR-21 for the treatment, amelioration, and/or prevention of fibrosis.

21 Claims, 13 Drawing Sheets

(56) References Cited

OTHER PUBLICATIONS

Krutzfeldt et al., "Specificity, duplex degradation and subcellular localization of antagomirs," Nucl. Acids Res. (2007) 35: 2885-2892.

Lu et al., "MicroRNA expression profiles classify human cancers," Nature. Jun. 9, 2005;435(7043):834-8.

Manoharan, "Oligonucleotide Conjugates as Potential Antisense Drugs with Improved Uptake, Biodistribution, Targeted Delivery, and Mechanism of Action," Antisense & Nucleic Acid Drug Development, 2002;12:103-128.

Meister et al., "Sequence-specific inhibition of microRNA- and siRNA-induced RNA silencing," RNA, 2004; 10:544-550.

Merkle et al., "A role for caspase-1 in heart failure," Circ Res. Mar. 16, 2007;100(5):645-53.

Mi et al., "MicroRNA expression signatures accurately discriminate acute lymphoblastic leukemia from acute myeloid leukemia," Proc Natl Acad Sci USA. Dec. 11, 2007;104(50):19971-6.

Rottbauer et al., "VEGF-PLCgamma1 pathway controls cardiac contractility in the embryonic heart," Genes Dev. Jul. 1, 2005;19(13):1624-34.

Sayed et al., "MicroRNAs play an essential role in the development of cardiac hypertrophy," Circ Res. Feb. 16, 2007;100(3):416-24.

Si et al., "MiR-21-Mediated Tumor Growth," Oncogene 2007;26: 2799-2803.

Tatsuguchi et al., "Expression of microRNAs is dynamically regulated during cardiomyocyte hypertrophy," J Mol Cell Cardiol. Jun. 2007;42(6):1137-41.

Thum et al., "MicroRNAs in the human heart: a clue to fetal gene reprogramming in heart failure," Circulation. Jul. 17, 2007;116(3):258-67.

Thum and Borlak, "Mechanistic role of cytochrome P450 monooxygenases in oxidized low-density lipoprotein-induced vascular injury: therapy through LOX-1 receptor antagonism?," Circ Res. Jan. 9, 2004;94(1):e1-13.

Yang et al., "The muscle-specific microRNA miR-1 regulates cardiac arrhythmogenic potential by targeting GJA1 and KCNJ2," Nat Med. Apr. 2007;13(4):486-91.

Eurasian Search Report from Eurasian Application No. 201070992, dated Apr. 15, 2011 (3 pages).

International Preliminary Report on Patentability for International Application No. PCT/EP2009/001590, mailed Aug. 31, 2010 (7 pages).

Liu et al., "miR-21 mediates fibrogenic activation of pulmonary fibroblasts and lung fibrosis," J Exp Med, 2010, 207 (8):1589-1597.

Wynn, "Common and unique mechanisms regulate fibrosis in various fibroproliferative diseases," J Clin Invest., 2007, 117(3):524-529.

Zarjou et al., "Identification of a microRNA signature in renal fibrosis: role of miR-21," Am J Physiol Renal Physiol, 2011, 301:F793-F801.

Milam et al., "PPAR-gamma agonists inhibit profibrotic phenotypes in human lung fibroblasts and bleomycin-induced pulmonary fibrosis," Am J Physiol Lung Cell Mol Physiol, 2008, 294:L891-L901.

Kramer et al., "Reduction of proteinuria in adriamycin-induced nephropathy is associated with reduction of renal kidney injury molecule (Kim-1) over time," 2009, 296:F1136-F1145.

Varga et al., Eds., Preface to Fibrosis Research: Methods and Protocols, 2005, pp. v-ix, Humana Press Inc., Totowa, NJ.

Extended European Search Report for EP 13160931.5 mailed Jul. 18, 2013, 6 pages.

MICRORNA (MIRNA) AND DOWNSTREAM TARGETS FOR DIAGNOSTIC AND THERAPEUTIC PURPOSES

FIELD OF THE INVENTION

The present invention relates to the field of microRNA (miRNA), in particular miR-21 and its down-stream targets for the diagnosis, prevention and/or therapy of fibrosis and other diseases. The present invention further relates to compositions, methods and uses for the treatment for fibrosis. Such methods comprise modulating and inhibiting the activity of a miRNA in a subject having fibrosis.

BACKGROUND OF THE INVENTION

MicroRNAs are a broad class of small non-coding RNAs that control diverse biological processes including major signaling pathways by regulating the expression of complementary target mRNAs (Ambros, 2004). Dysregulation of microRNAs in various disease entities is caused by alterations in the genome (Mi et al., 2007), differential expression or viral infections in some cases changing microRNA function into tumor suppressors or oncogenes. MicroRNAs were recently implicated in the regulation of diverse cardiac functions in a series of elegant genetic studies (Care et al., 2007; Yang et al., 2007). Although these studies help to delineate the roles of microRNA in heart physiology, growth and morphogenesis, detailed molecular mechanisms for microRNAs in disease pathways in vivo are poorly understood. Single-stranded oligonucleotide microRNA antagonists have been shown to silence endogenous microRNAs in vitro and in vivo with resulting effects on target mRNA and protein levels and metabolism (Kruetzfeldt et al., 2005; Esau et al., 2006). These findings pointed to the application of microRNA antagonists for in vivo validation of microRNA function and, perhaps more importantly, as a novel therapeutic modality.

SUMMARY

The present invention relates to a promoter region of a microRNA, the use of a microRNA, in particular miR-21, and related elements for the diagnosis and for the manufacture of a medicament for the treatment and/or prevention of fibrosis and/or fibrosis related diseases. Additionally, the invention concerns various antisense oligonucleotides against targets of miR-21. A cell deficient for miR-21, the promoter region and targets of miR-21 and a knock-out organism thereof are also encompassed. Finally, the invention is directed to a method for diagnosing fibrosis and/or fibrosis related diseases and to a method for screening a pharmaceutically active compound for the treatment of fibrosis and/or fibrosis related diseases.

Provided herein are methods for treating fibrosis, comprising administering to a subject having or suspected of having fibrosis a compound comprising a modified oligonucleotide consisting of 12 to 30 linked nucleosides and having a nucleobase sequence complementary to an miRNA.

Provided herein are methods comprising identifying a subject having or suspected of having fibrosis; and administering to the subject a compound comprising a modified oligonucleotide consisting of 12 to 30 linked nucleosides, wherein the nucleobase sequence of the modified oligonucleotide is complementary a miRNA or a precursor thereof.

Provided herein are methods comprising administering to a subject at risk for developing fibrosis a compound comprising a modified oligonucleotide consisting of 12 to 30 linked nucleosides and having a nucleobase sequence which complementary to a miRNA or a precursor thereof, thereby preventing fibrosis. In certain embodiments, the fibrosis is liver fibrosis. In certain embodiments, the fibrosis is lung fibrosis. In certain embodiments, the fibrosis is skin fibrosis. In certain embodiments, the fibrosis is age-related fibrosis. In certain embodiments, the fibrosis is cardiac fibrosis. In certain embodiments, the fibrosis is kidney fibrosis. In certain embodiments, the fibrosis is spleen fibrosis.

Provided herein are methods comprising administering to a subject having or suspected of having fibrosis a compound comprising a modified oligonucleotide consisting of 12 to 30 linked nucleosides and having a nucleobase sequence which is complementary to a miRNA or a precursor thereof, wherein the subject has at least one cardiac disease or condition.

Provided herein are methods comprising identifying a subject having or suspected of having fibrosis, wherein the subject has at least one cardiac disease or condition; and administering to the subject a compound comprising a modified oligonucleotide consisting of 12 to 30 linked nucleosides, wherein the nucleobase sequence of the modified oligonucleotide is complementary to a miRNA or a precursor thereof.

In certain embodiments, the cardiac disease or condition is selected from the group consisting of cardiac hypertrophy, hypertensive heart failure, diastolic heart failure, systolic heart failure, heart-related storage disease, cardiomyopathy, constrictive pericarditis, coronary artery disease, acute myocardial infarction, chronic myocardial infarction, right heart failure, cardiac arrhythmias, myocarditis-related fibrosis, and heart valve disease.

In certain embodiments the cardiomyopathy is selected from the group consisting of dilatative cardiomyopathy, hypertrophic cardiomyopathy with obstruction, hypertrophic cardiomyopathy without obstruction, restrictive cardiomyopathy, arrhythmogenic right ventricular cardiomyopathy, and diabetic cardiomyopathy.

In certain embodiments the heart valve disease is selected from the group consisting of mitral valve stenosis, aortic valve stenosis, tricuspidal valve stenosis, and pulmonary valve stenosis.

In certain embodiments the heart valve disease is selected from the group consisting of mitral valve insufficiency, aortic valve insufficiency, tricuspidal valve insufficiency, and pulmonary valve insufficiency.

In certain embodiments the methods provided herein further comprise administering one or more additional pharmaceutical agents.

In certain embodiments the administering ameliorates heart weight increase, left ventricular dilation, or impairment of fractional shortening.

In certain embodiments the administering prevents heart weight increase, left ventricular dilation, or impairment of fractional shortening.

In certain embodiments the administering improves cardiac function.

In certain embodiments the administering comprises intravenous administration, subcutaneous administration, intraarterial administration, or intracardial administration.

Provided herein are methods for treating fibrosis, comprising administering to a subject having or suspected of having fibrosis a compound comprising a modified oligonucleotide consisting of 12 to 30 linked nucleosides and having a nucleobase sequence complementary to a miRNA or a precursor thereof, wherein the subject has at least one liver disease or condition.

Provided herein are methods comprising identifying a subject having or suspected of having fibrosis, wherein the subject has at least one liver disease or condition; and administering to the subject a compound comprising a modified oligonucleotide consisting of 12 to 30 linked nucleosides, wherein the nucleobase sequence of the modified oligonucleotide is complementary to a miRNA or a precursor thereof. In certain embodiments, the at least one liver disease or condition is chronic liver injury. In certain embodiments, the at least one liver disease or condition is hepatitis virus infection. In certain embodiments the hepatitis infection is hepatitis C virus infection. In certain embodiments the at least one liver disease or condition is non-alcoholic steatohepatitis. In certain embodiments the administration comprises intravenous administration or subcutaneous administration. In certain embodiments the at least one liver disease or condition is cirrhosis. In certain embodiments the administering improves liver function.

Provided herein are methods for treating fibrosis, comprising administering to a subject having or suspected of having fibrosis a compound comprising a modified oligonucleotide consisting of 12 to 30 linked nucleosides and having a nucleobase sequence complementary to a miRNA or a precursor thereof, wherein the subject has at least one lung disease or condition.

Provided herein are methods comprising identifying a subject having or suspected of having fibrosis, wherein the subject has at least one lung disease or condition; and administering to the subject a compound comprising a modified oligonucleotide consisting of 12 to 30 linked nucleosides, wherein the nucleobase sequence of the modified oligonucleotide is complementary to a miRNA or a precursor thereof. In certain embodiments the at least one other lung disease or condition is chronic obstructive lung disease. In certain embodiments the administering comprises pulmonary administration.

Provided herein are methods for treating fibrosis, comprising administering to a subject having or suspected of having fibrosis a compound comprising a modified oligonucleotide consisting of 12 to 30 linked nucleosides and having a nucleobase sequence complementary to a miRNA or a precursor thereof, wherein the subject has at least one other disease or condition.

Provided herein are methods comprising identifying a subject having or suspected of having fibrosis, wherein the subject has at least one other disease or condition; and administering to the subject a compound comprising a modified oligonucleotide consisting of 12 to 30 linked nucleosides, wherein the nucleobase sequence of the modified oligonucleotide is complementary to a miRNA or a precursor thereof. In certain embodiments the at least one other disease or condition is pulmonary hypertension. In certain embodiments the at least one other disease or condition is a blood vessel-related disease. In certain embodiments the blood-vessel related disease is selected from the group consisting of arterial stiffness, mediasclerosis, and arteriosclerosis. In certain embodiments the at least one other disease or condition is gut sclerosis. In certain embodiments the at least one other disease or condition is systemic sclerosis. In certain embodiments the at least one other disease or condition is selected from the group consisting of retroperitoneal fibrosis, proliferative fibrosis, neoplastic fibrosis, nephrogenic systemic fibrosis, injection fibrosis, mediastinal fibrosis, myelofibrosis, post-vasectomy pain syndrome, rheumatoid arthritis.

In certain embodiments, the administering ameliorates the fibrosis. In certain embodiments, the administering slows further progression of the fibrosis. In certain embodiments the administering halts further progression of fibrosis. In certain embodiments the administering reduces fibrosis. In certain embodiments the administering reduces collagen content.

Provided herein are methods for treating a fibroproliferative disorder comprising administering to a subject having or suspected of having a fibroproliferative disorder a compound comprising a modified oligonucleotide consisting of 12 to 30 linked nucleosides, wherein the nucleobase sequence of the modified oligonucleotide is complementary to a miRNA or a precursor thereof, thereby treating the fibroproliferative disorder.

In certain embodiments administration comprises intravenous administration, subcutaneous administration, pulmonary administration, intraarterial administration, or intracardiac administration.

Provided herein are methods for inhibiting fibroblast proliferation comprising contacting a fibroblast with a compound comprising a modified oligonucleotide consisting of 12 to 30 linked nucleosides, wherein the nucleobase sequence of the modified oligonucleotide is complementary to a miRNA or a precursor thereof, thereby inhibiting fibroblast proliferation.

Provided herein are methods for stimulating fibroblast apoptosis comprising contacting a fibroblast with a compound comprising a modified oligonucleotide consisting of 12 to 30 linked nucleosides, wherein the nucleobase sequence of the modified oligonucleotide is complementary to miR-21 or a precursor thereof, thereby stimulating fibroblast apoptosis.

Provided herein are methods for increasing Sprouty 1 protein in a fibroblast comprising contacting the fibroblast with a compound comprising a modified oligonucleotide consisting of 12 to 30 linked nucleosides, wherein the nucleobase sequence of the modified oligonucleotide is complementary to a miRNA or a precursor thereof, thereby stimulating Sprouty 1 protein expression.

Provided herein are compositions for inhibiting MicroRNA. In certain embodiments, the miRNA is miR-21. In certain embodiments the modified oligonucleotide has a nucleobase sequence complementary to a nucleobase sequence which is at least 80% identical to miR-21 or a precursor thereof. In certain embodiments miR-21 has the nucleobase sequence set forth as SEQ ID NO: 1. In certain embodiments the miR-21 precursor has the nucleobase sequence set forth as SEQ ID NO: 11.

In certain embodiments the modified oligonucleotide consists of 12 to 30 linked nucleosides. In certain embodiments the modified oligonucleotide consists of 12 linked nucleosides. In certain embodiments the modified oligonucleotide consists of 13 linked nucleosides. In certain embodiments the modified oligonucleotide consists of 14 linked nucleosides. In certain embodiments the modified oligonucleotide consists of 15 to 24 linked nucleosides. In certain embodiments the modified oligonucleotide consists of 15 linked nucleosides. In certain embodiments the modified oligonucleotide consists of 16 linked nucleosides. In certain embodiments the modified oligonucleotide consists of 17 linked nucleosides. In certain embodiments the modified oligonucleotide consists of 18 linked nucleosides. In certain embodiments the modified oligonucleotide consists of 19 linked nucleosides. In certain embodiments the modified oligonucleotide consists of 20 linked nucleosides. In certain embodiments the modified oligonucleotide consists of 21 linked nucleosides. In certain embodiments the modified oligonucleotide consists of 22 linked nucleosides. In certain embodiments the modified oligonucleotide consists of 23 linked nucleosides. In certain embodiments the modified oligonucleotide consists of 24 linked nucleosides.

In certain embodiments the nucleobase sequence of the modified oligonucleotide has no more than two mismatches to the nucleobase sequence of miR-21 or a precursor thereof.

In certain embodiments the nucleobase sequence of the modified oligonucleotide has no more than one mismatch to the nucleobase sequence of miR-21 br a precursor thereof. In certain embodiments the nucleobase sequence of the modified oligonucleotide has no mismatches to the nucleobase sequence of miR-21 or a precursor thereof.

In certain embodiments the nucleobase sequence of the modified oligonucleotide comprises at least 15 contiguous nucleobases of the nucleobase sequence of SEQ ID NO: 12. In certain embodiments the nucleobase sequence of the modified oligonucleotide comprises at least 16 contiguous nucleobases of the nucleobase sequence of SEQ ID NO: 12. In certain embodiments the nucleobase sequence of the modified oligonucleotide comprises at least 17 contiguous nucleobases of the nucleobase sequence of SEQ ID NO: 12. In certain embodiments the nucleobase sequence of the modified oligonucleotide comprises at least 18 contiguous nucleobases of the nucleobase sequence of SEQ ID NO: 12. In certain embodiments the nucleobase sequence of the modified oligonucleotide comprises at least 19 contiguous nucleobases of the nucleobase sequence of SEQ ID NO: 12. In certain embodiments the nucleobase sequence of the modified oligonucleotide comprises at least 20 contiguous nucleobases of the nucleobase sequence of SEQ ID NO: 12. In certain embodiments the nucleobase sequence of the modified oligonucleotide comprises at least 21 contiguous nucleobases of the nucleobase sequence of SEQ ID NO: 12. In certain embodiments the nucleobase sequence of the modified oligonucleotide comprises at least 22 contiguous nucleobases of the nucleobase sequence of SEQ ID NO: 12.

In certain embodiments the nucleobase sequence of the modified oligonucleotide consists of the nucleobase sequence of SEQ ID NO: 12.

In certain embodiments, the compound comprises a modified oligonucleotide conjugated to a ligand. In certain embodiments has the structure (III)

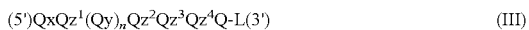
(5')QxQz$^1$(Qy)$_n$Qz$^2$Qz$^3$Qz$^4$Q-L(3')                (III)

Wherein
Each Q is independently a 2'-O-methyl modified nucleoside;
x is

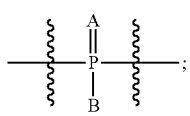

One of A and B is S while the other is O;
y is

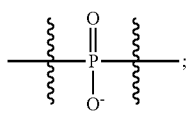 [SMILES: *P(*)(=O)[O-]]

Each of z$^1$, z$^2$, z$^3$, and z$^4$ is independently x or y;
n=6-17
L is

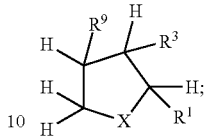

Wherein:
X is N(CO)R$^7$, or NR$^7$;
Each of R$^1$, R$^3$ and R$^9$, is independently, H, OH, or —CH$_2$OR$^b$ provided that at least one of R$^1$, R$^3$ and R$^9$ is OH and at least one of R$^1$, R$^3$ and R$^9$ is —CH$_2$OR$^b$;
R$^7$ is R$^d$ or C$_1$-C$_{20}$ alkyl substituted with NR$^c$R$^d$ or NHC(O)R$^d$;
R$^c$ is H or C$_1$-C$_6$ alkyl;
R$^d$ is a carbohydrate radical; or a steroid radical, which is optionally tethered to at least one carbohydrate radical; and
R$^b$ is

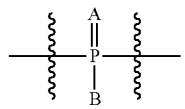

with one of A and B is S while the other is O.

In certain embodiments, Rd is cholesterol. In certain embodiments, each of z$^1$, z$^2$, z$^3$, and z$^4$ is

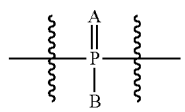

with one of A and B is S while the other is O.

In certain embodiments, R$^1$ is —CH$_2$OR$^b$. In certain embodiments, R$^9$ is OH. In certain embodiments, R$^1$ and R$^9$ are trans. In certain embodiments, R$^1$ and R$^3$ are trans. In certain embodiments, R$^3$ is —CH$_2$OR$^b$. In certain embodiments, R$^1$ is OH. In certain embodiments, R$^1$ and R$^3$ are trans. In certain embodiments, R$^3$ and R$^9$ are trans. In certain embodiments, R$^9$ is CH$_2$OR$^b$. In certain embodiments, X is NC(O)R$^7$. In certain embodiments, R$^7$ is —CH$_2$(CH$_2$)$_3$CH$_2$NHC(O)R$^d$.

In certain embodiments, at least one internucleoside linkage is a modified internucleoside linkage. In certain embodiments, each internucleoside linkage is a modified internucleoside linkage. In certain embodiments, at least one internucleoside linkage is a phosphorothioate internucleoside linkage. In certain embodiments, each internucleoside linkage is a phosphorothioate internucleoside linkage. In certain embodiments, at least one nucleoside comprises a modified sugar. In certain embodiments, a plurality of nucleosides comprises a modified sugar. In certain embodiments, each nucleoside comprises a modified sugar. In certain embodiments, each nucleoside comprises a 2'-O-methoxyethyl sugar. In certain embodiments, each of a plurality of nucleosides comprises a 2'-O-methoxyethyl sugar and each of a plurality of nucleosides comprises a 2'-fluoro sugar. In certain embodiments, each modified sugar is independently selected from a 2'-O-methoxyethyl sugar, a 2'-fluoro sugar, a 2'-O-methyl sugar, or a bicyclic sugar moiety. In certain embodiments, at least one nucleoside comprises a modified nucleobase. In certain embodiments, the modified nucleobase is a 5-methylcytosine. In certain embodiments, at least one nucleoside comprises a cytosine, wherein the cytosine is a 5-methylcytosine. In certain embodiments, each cytosine is a 5-methylcytosine.

In certain embodiments, the nucleobase sequence of the modified oligonucleotide is at least 90% complementary to the nucleobase sequence of SEQ ID NO: 1. In certain embodiments, the nucleobase sequence of the modified oligonucleotide is at least 95% complementary to the nucleobase sequence of SEQ ID NO: 1. In certain embodiments, the nucleobase sequence of the modified oligonucleotide is 100% complementary to the nucleobase sequence of SEQ ID NO: 1. In certain embodiments, the nucleobase sequence of the modified oligonucleotide has full-length complementary to the nucleobase sequence of SEQ ID NO: 1. In certain embodiments, the nucleobase sequence of the modified oligonucleotide is at least 90% complementary to the nucleobase sequence of SEQ ID NO: 11. In certain embodiments, the nucleobase sequence of the modified oligonucleotide is at least 95% complementary to the nucleobase sequence of SEQ ID NO: 11. In certain embodiments, the nucleobase sequence of the modified oligonucleotide is 100% complementary to the nucleobase sequence of SEQ ID NO: 11. In certain embodiments, the miR-21 nucleobase sequence consists of the nucleobase sequence of SEQ ID NO: 1. In certain embodiments, the precursor nucleobase sequence consists of the nucleobase sequence of SEQ ID NO: 11.

In certain embodiments, the compound comprising the modified oligonucleotide is prepared as a pharmaceutical composition. In certain embodiments, the modified oligonucleotide is prepared as a pharmaceutical composition.

In certain embodiments, the compound consists of a modified oligonucleotide. In certain embodiments, the modified oligonucleotide is a single-stranded modified oligonucleotide. In certain embodiments, the modified oligonucleotide is an antisense oligonucleotide.

Provided herein are compositions for use in the treatment, prevention, and/or amelioration of fibrosis. Further provided herein are compounds comprising modified oligonucleotides having a nucleobase sequence complementary to a miRNA, for use in the treatment, prevention, and/or amelioration of fibrosis.

Provided herein are antisense oligonucleotides complementary to miR-21 for the manufacture of a medicament for the treatment and/or prevention of fibrosis.

Provided herein are antisense oligonucleotides complementary to miR-21 for use in the treatment and/or prevention of fibrosis.

Provided herein is the use of miR-21 and/or an antisense oligonucleotide against miR-21 for the treatment of fibrosis. Provided herein is the use of miR-21 and/or an antisense oligonucleotide against miR-21 for the diagnosis of fibrosis.

DATA NOT SHOWN

Figure 1:
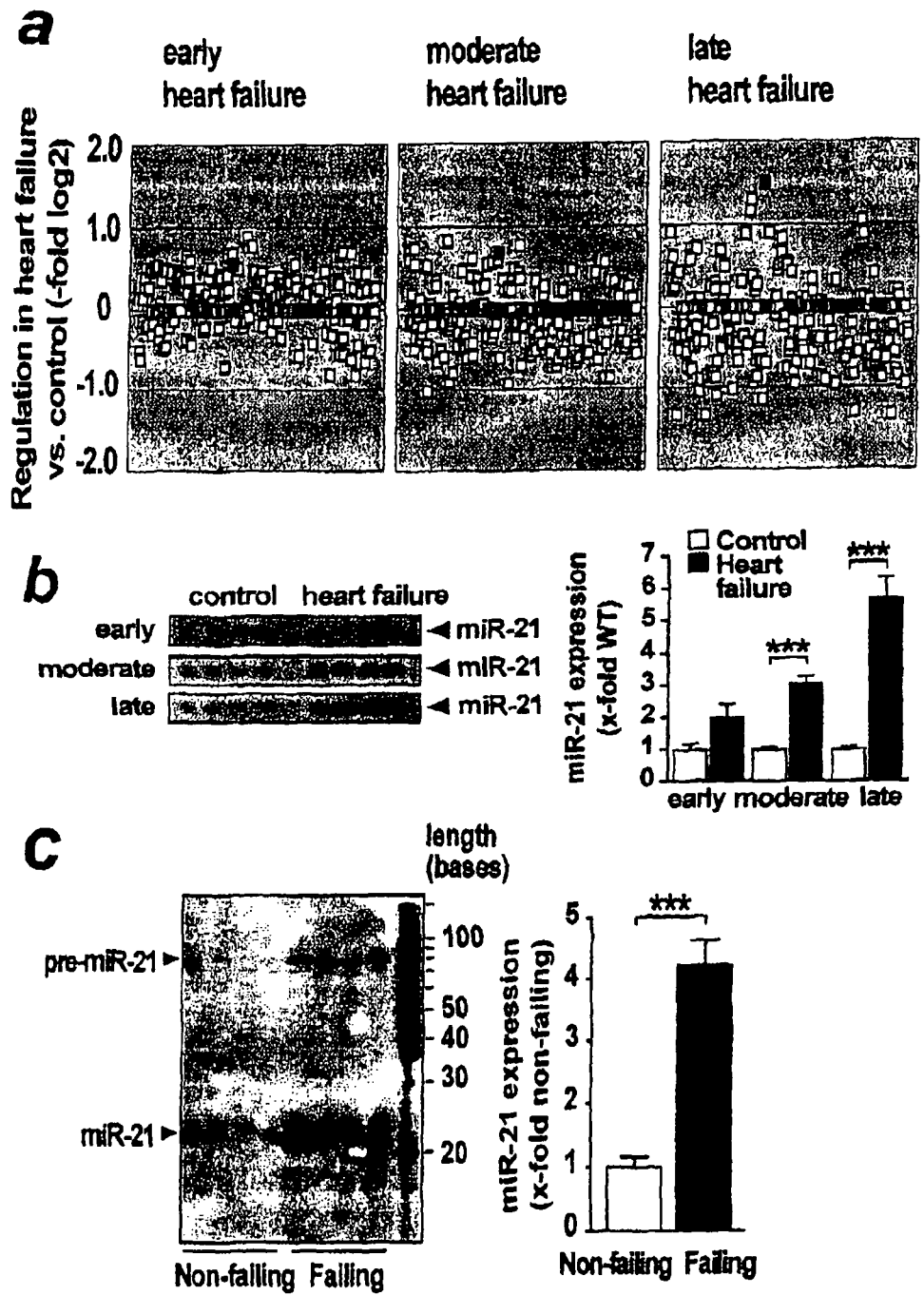
FIG. 1 Deregulation of miR-21 in Cardiac Disease and Predominant Expression in Cardiac Fibroblasts
(a) Analysis of microRNA-expression by microarrays. RNA was isolated from left ventricular myocardium of a murine model of heart failure (β1AR-TG mice) at early (three months old), moderate (six months old) and late stages (twelve months) of heart failure. Expression is presented as fold regulation vs. wild-type controls. miR-21 is marked in red. Data are from 3-4 independent hybridizations per group.
(b) Left Northern blot analysis of miR-21 expression at different stages of heart failure in β1AR-TG mice. Right Quantitative analysis of the data from the upper panel.
(c) Left Northern blot analysis of miR-21 expression in non-failing and failing human left ventricular myocardium. Right Quantitative analysis of the mature form of miR-21 in non-failing and failing human left ventricular myocardium.
(d) Upper Neonatal cardiomyocytes stained with 4',6-diamidino-2-phenylindole (DAPI) and an antibody directed against α-actinin after transfection with scrambled-miR (control-pre-miR, 50 nM, 72 h), synthetic miR-21 (pre-miR-21, 50 nM, 72 h) and a miR-21 inhibitor (anti-miR-21, 50 nM, 72 h). Cardiomyocytes were cultured under control conditions (see Supplemental Methods) or stimulated with FCS (5%) for 48 h. Lower Quantitative analysis of individual cardiomyocyte sizes (histogram analysis). n>200 cardiomyocytes were analyzed per group.
(e) Upper Generation of transgenic mice expressing miR-21 under the control of the alpha-MHC promoter. Middle Northern blot of mature miR-21 in wild type (WT) and transgenic (TG) animals. Lower Cross sectional cardiac areas from wild type and miR-21-transgenic mice stained to determine general morphology (HE-stain) and collagen deposition (Sirius red).
(f) miR-21 expression in cardiac fibroblasts and cardiomyocytes. Northern blot (Upper) and quantitative real-time-PCR analysis (Lower). All error bars indicate SEM. n=3-6 for a-f.
Figure 1:
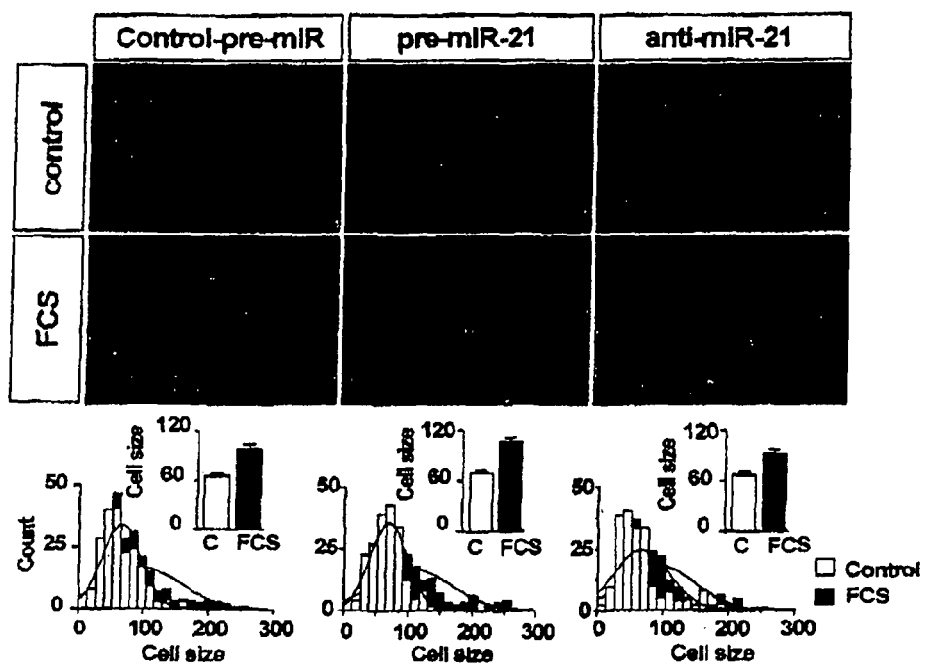
Figure 1:
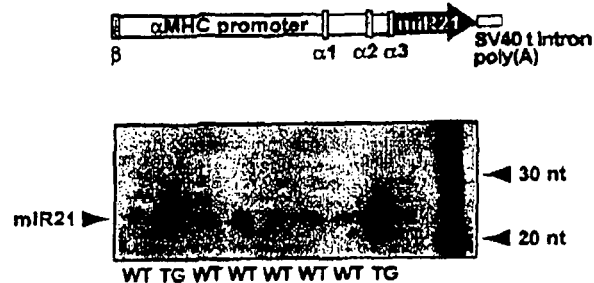
Figure 1:
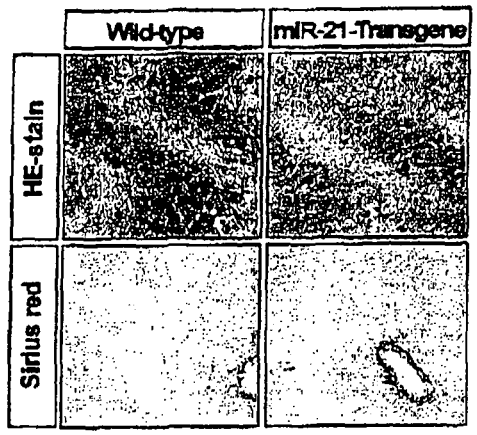
Figure 1:
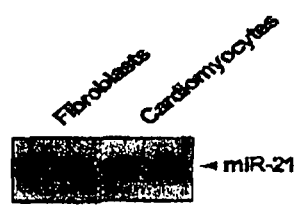
Figure 1:
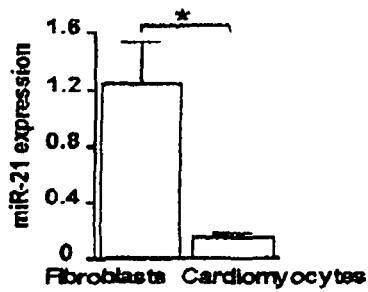

A screen for theoretical miR-21 targets revealed 22 known potential target genes, of which 8 were shown to be expressed within cardiac tissue. Combination of three different target prediction tools identified Spry1 (sprouty1) as a highly likely candidate.
Transcriptional Regulation of miR-21
There is sequence conservation within the miR-21-promoter regions of different species in comparison to the human miR-21-promoter. Luciferase activity of human miR-21-promoter constructs after deletion/mutation of individual transcription factor binding sites was shown. Progressive shortening of the native promoter leads to identification of a 117 by region that is responsible for expression of miR-21. n=3.
Transfection Efficacy in Cultured Cardiomyocytes
Cultured neonatal cardiomyocytes were transfected with Cy-3 labeled miR-21 (50 nM, 72 h, Ambion, USA) and stained with DAPI. For comparison cultured cardiomyocytes were stained with DAPI alone. Northern blotting of miR-21 expression in cultured cardiomyocytes after transfection with scrambled-microRNA (control-pre-miR, 50 nM, 72 h), a miR-21 inhibitor (anti-miR-21, 50 nM, 72 h), or synthetic miR-21 (pre-miR-21, 50 nM, 72 h) was analyzed.
MicroRNA-Binding Sites within the 3.UTR of the Spry1 Gene
There is a change in expression of various microRNAs with binding sites within the 3'UTR of the Spry1 gene. microRNAs with binding sites within the 3'UTR were analyzed by microRNA microarray.
miR-21 Real-Time PCR Expression Data
In addition to determination by Northern blotting, expression of miR-21 was analyzed by realtime-PCR in left ventricular tissue of mice after sham-operation, sham+miR-21 antagonist treatment, TAC and TAC+miR-21 antagonist treatment as well as in hearts from wildtype mice and miR-21 transgenic mice.

DETAILED DESCRIPTION

Definitions

"Fibrosis" means the formation or development of excess fibrous connective tissue in an organ or tissue. In certain embodiments, fibrosis occurs as a reparative or reactive process. In certain embodiments, fibrosis occurs in response to damage or injury. The term "fibrosis" is to be understood as the formation or development of excess fibrous connective tissue in an organ or tissue as a reparative or reactive process, as opposed to a formation of fibrous tissue as a normal constituent of an organ or tissue.

An antisense oligonucleotide is to be understood as a oligonucleotide which has a certain sequence complementary to another sequence, in particular a sequence complementary to miR-21. A target of miR-21 may also be understood to encompass a downstream target of miR-21. It is important to note that an inhibition of miR-21, e.g. via an oligonucleotide with a sequence at least complementary to miR-21 will lead to a derepression or even an overexpression of targets of miR-21, like Sprouty and the like.

"Subject" means a human or non-human animal selected for treatment or therapy.

"Subject suspected of having" means a subject exhibiting one or more clinical indicators of a disease or condition.

"Subject suspected of having fibrosis" means a subject exhibiting one or more clinical indicators of fibrosis.

"Preventing" or "prevention" refers to delaying or forestalling the onset, development or progression of a condition or disease for a period of time, including weeks, months, or years.

"Treatment" or "treat" means the application of one or more specific procedures used for the cure or amelioration of a disease. In certain embodiments, the specific procedure is the administration of one or more pharmaceutical agents.

"Amelioration" means a lessening of severity of at least one indicator of a condition or disease. In certain embodiments, amelioration includes a delay or slowing in the progression of one or more indicators of a condition or disease. The severity of indicators may be determined by subjective or objective measures which are known to those skilled in the art.

"Subject in need thereof" means a subject identified as in need of a therapy or treatment.

"Administering" means providing a pharmaceutical agent or composition to a subject, and includes, but is not limited to, administering by a medical professional and self-administering.

"Parenteral administration," means administration through injection or infusion.

Parenteral administration includes, but is not limited to, subcutaneous administration, intravenous administration, intramuscular administration, intraarterial administration, and intracranial administration.

"Subcutaneous administration" means administration just below the skin.

"Intravenous administration" means administration into a vein.

"Intraarterial administration" means administration into an artery.

"Intracardial administration" means administration into the heart. In certain embodiments, intracardial administration occurs by way of a catheter. In certain embodiments, intracardial administration occurs by way of open heart surgery.

"Pulmonary administration" means administration to the lungs.

"Improves liver function" means the changes liver function toward normal parameters. In certain embodiments, liver function is assessed by measuring molecules found in a subject's blood. For example, in certain embodiments, improved liver function is measured by a reduction in blood liver transaminase levels.

"Pharmaceutical composition" means a mixture of substances suitable for administering to an individual that includes a pharmaceutical agent. For example, a pharmaceutical composition may comprise a modified oligonucleotide and a sterile aqueous solution.

"Pharmaceutical agent" means a substance that provides a therapeutic effect when administered to a subject.

"Active pharmaceutical ingredient" means the substance in a pharmaceutical composition that provides a desired effect.

"Target nucleic acid," "target RNA," "target RNA transcript" and "nucleic acid target" all mean any nucleic acid capable of being targeted by antisense compounds.

"Targeting" means the process of design and selection of nucleobase sequence that will hybridize to a target nucleic acid and induce a desired effect.

"Targeted to" means having a nucleobase sequence that will allow hybridization to a target nucleic acid to induce a desired effect. In certain embodiments, a desired effect is reduction of a target nucleic acid.

"Modulation" means to a perturbation of function or activity. In certain embodiments, modulation means an increase in gene expression. In certain embodiments, modulation means a decrease in gene expression.

"Expression" means any functions and steps by which a gene's coded information is converted into structures present and operating in a cell.

"5' target site" refers to the nucleobase of a target nucleic acid which is complementary to the 5'-most nucleobase of a particular oligonucleotide.

"3' target site" means the nucleobase of a target nucleic acid which is complementary to the 3'-most nucleobase of a particular oligonucleotide.

"Region" means a portion of linked nucleosides within a nucleic acid. In certain embodiments, a modified oligonucleotide has a nucleobase sequence that is complementary to a region of a target nucleic acid. For example, in certain such embodiments a modified oligonucleotide is complementary to a region of a miRNA stem-loop sequence. In certain such embodiments, a modified oligonucleotide is 100% to a region of a miRNA stem-loop sequence.

"Segment" means a smaller or sub-portion of a region.

"Nucleobase sequence" means the order of contiguous nucleobases, in a 5' to 3' orientation, independent of any sugar, linkage, and/or nucleobase modification.

"Contiguous nucleobases" means nucleobases immediately adjacent to each other in a nucleic acid.

"Nucleobase complementarity" means the ability of two nucleobases to pair non-covalently via hydrogen bonding.

"Complementary" means a first nucleobase sequence is at least 60%, 65%, 70%, 75%, 80%, 85%, 90%, 95%, 97%, 98 or 99% identical, or is 100% identical, to the complement of a second nucleobase sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleobases, or that the two sequences hybridize under stringent hybridization conditions. In certain embodiments a modified oligonucleotide that has a nucleobase sequence which is 100% complementary to a miRNA, or precursor thereof, may not be 100% complementary to the miRNA, or precursor thereof, over the entire length of the modified oligonucleotide.

"Complementarity" means the nucleobase pairing ability between a first nucleic acid and a second nucleic acid.

"Full-length complementarity" means each nucleobase of a first nucleic acid is capable of pairing with each nucleobase at a corresponding position in a second nucleic acid. For example, in certain embodiments, a modified oligonucleotide wherein each nucleobase has complementarity to a nucleobase in an miRNA has full-length complementarity to the miRNA.

"Percent complementary" means the number of complementary nucleobases in a nucleic acid divided by the length of the nucleic acid. In certain embodiments, percent complementarity of a modified oligonucleotide means the number of nucleobases that are complementary to the target nucleic acid, divided by the number of nucleobases of the modified oligonucleotide. In certain embodiments, percent complementarity of a modified oligonucleotide means the number of nucleobases that are complementary to a miRNA, divided by the number of nucleobases of the modified oligonucleotide.

"Percent region bound" means the percent of a region complementary to an oligonucleotide region. Percent region bound is calculated by dividing the number of nucleobases of the target region that are complementary to the oligonucleotide by the length of the target region. In certain embodiments, percent region bound is at least 80%, at least 85%, at least 90%, at least 95%, at least 96%, at least 97%, at least 98%, at least 99%, or 100%.

"Percent identity" means the number of nucleobases in first nucleic acid that are identical to nucleobases at corresponding positions in a second nucleic acid, divided by the total number of nucleobases in the first nucleic acid.

"Substantially identical" used herein may mean that a first and second nucleobase sequence are at least 60%, 65%, 70%, 75%, 80%, 85%, 90%, 95%, 97%, 98% or 99% identical, or 100% identical, over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleobases.

"Hybridize" means the annealing of complementary nucleic acids that occurs through nucleobase complementarity.

"Mismatch" means a nucleobase of a first nucleic acid that is not capable of pairing with a nucleobase at a corresponding position of a second nucleic acid.

"Non-complementary nucleobase" means two nucleobases that are not capable of pairing through hydrogen bonding.

"Identical" means having the same nucleobase sequence.

"miRNA" or "miR" means a non-coding RNA between 18 and 25 nucleobases in length which hybridizes to and regulates the expression of a coding RNA. In certain embodiments, a miRNA is the product of cleavage of a pre-miRNA by the enzyme Dicer. Examples of miRNAs are found in the miRNA database known as miRBase (http://microrna.sanger.ac.uk/).

"Pre-miRNA" or "pre-miR" means a non-coding RNA having a hairpin structure, which contains a miRNA. In certain embodiments, a pre-miRNA is the product of cleavage of a pri-miR by the double-stranded RNA-specific ribonuclease known as Drosha.

"Stem-loop sequence" means an RNA having a hairpin structure and containing a mature miRNA sequence. Pre-miRNA sequences and stem-loop sequences may overlap. Examples of stem-loop sequences are found in the miRNA database known as miRBase (http://microrna.sanger.ac.uk/).

"Pri-miRNA" or "pri-miR" means a non-coding RNA having a hairpin structure that is a substrate for the double-stranded RNA-specific ribonuclease Drosha.

"miRNA precursor" means a transcript that originates from a genomic DNA and that comprises a non-coding, structured RNA comprising one or more miRNA sequences. For example, in certain embodiments a miRNA precursor is a pre-miRNA. In certain embodiments, a miRNA precursor is a pri-miRNA.

"Monocistronic transcript" means a miRNA precursor containing a single miRNA sequence.

"Polycistronic transcript" means a miRNA precursor containing two or more miRNA sequences.

"Seed region" means nucleotides 2 to 6 or 2 to 7 from the 5'-end of a mature miRNA sequence.

"Oligomeric compound" means a compound comprising a polymer of linked monomeric subunits.

"Oligonucleotide" means a polymer of linked nucleosides, each of which can be modified or unmodified, independent from one another.

"Naturally occurring internucleoside linkage" means a 3' to 5' phosphodiester linkage between nucleosides.

"Natural sugar" means a sugar found in DNA (2'-H) or RNA (2'-OH).

"Natural nucleobase" means a nucleobase that is unmodified relative to its naturally occurring form.

"Internucleoside linkage" means a covalent linkage between adjacent nucleosides.

"Linked nucleosides" means nucleosides joined by a covalent linkage.

"Nucleobase" means a heterocyclic moiety capable of non-covalently pairing with another nucleobase.

"Nucleoside" means a nucleobase linked to a sugar.

"Nucleotide" means a nucleoside having a phosphate group covalently linked to the sugar portion of a nucleoside.

"miR antagonist" means a modified oligonucleotide complementary to a miRNA, or a precursor thereof. For example, "miR-X antagonist" means a modified oligonucleotide having nucleobase complementarity to miR-X. In certain embodiments, an antagonist is a miR-21 antagonist.

"Modified oligonucleotide" means an oligonucleotide having one or more modifications relative to a naturally occurring terminus, sugar, nucleobase, and/or internucleoside linkage.

"Single-stranded modified oligonucleotide" means a modified oligonucleotide which is not hybridized to a complementary strand.

"Modified internucleoside linkage" means any change from a naturally occurring internucleoside linkage.

"Phosphorothioate internucleoside linkage" means a linkage between nucleosides where one of the non-bridging atoms is a sulfur atom.

"Modified sugar" means substitution and/or any change from a natural sugar.

"Modified nucleobase" means any substitution and/or change from a natural nucleobase.

"5-methylcytosine" means a cytosine modified with a methyl group attached to the 5' position.

"2'-O-methyl sugar" or "2'-OMe sugar" means a sugar having a O-methyl modification at the 2' position.

"2'-O-methoxyethyl sugar" or "2'-MOE sugar" means a sugar having a O-methoxyethyl modification at the 2' position.

"2'-O-fluoro sugar" or "2'-F sugar" means a sugar having a fluoro modification of the 2' position.

"Bicyclic sugar moiety" means a sugar modified by the bridging of two non-geminal ring atoms.

"2'-O-methoxyethyl nucleoside" means a 2'-modified nucleoside having a 2'-O-methoxyethyl sugar modification.

"2'-fluoro nucleoside" means a 2'-modified nucleoside having a 2'-fluoro sugar modification.

"2'-O-methyl" nucleoside means a 2'-modified nucleoside having a 2'-O-methyl sugar modification.

"Bicyclic nucleoside" means a 2'-modified nucleoside having a bicyclic sugar moiety.

"Motif" means a pattern of modified and/or unmodified nucleobases, sugars, and/or internucleoside linkages in an oligonucleotide.

A "fully modified oligonucleotide" means each nucleobase, each sugar, and/or each internucleoside linkage is modified.

A "uniformly modified oligonucleotide" means each nucleobase, each sugar, and/or each internucleoside linkage has the same modification throughout the modified oligonucleotide.

A "stabilizing modification" means a modification to a nucleoside that provides enhanced stability to a modified oligonucleotide, in the presence of nucleases, relative to that provided by 2'-deoxynucleosides linked by phosphodiester internucleoside linkages. For example, in certain embodiments, a stabilizing modification is a stabilizing nucleoside modification. In certain embodiments, a stabilizing modification is a internucleoside linkage modification.

A "stabilizing nucleoside" means a nucleoside modified to provide enhanced nuclease stability to an oligonucleotide, relative to that provided by a 2'-deoxynucleoside. In one embodiment, a stabilizing nucleoside is a 2'-modified nucleoside.

A "stabilizing internucleoside linkage" means an internucleoside linkage that provides enhanced nuclease stability to an oligonucleotide relative to that provided by a phosphodiester internucleoside linkage. In one embodiment, a stabilizing internucleoside linkage is a phosphorothioate internucleoside linkage.

Overview

It is discovered herein that modified oligonucleotides complementary to miR-21 are pharmaceutical agents for the inhibition of miR-21. In certain embodiments, the modified oligonucleotides are administered to a subject having a disease characterized by the upregulation of miR-21. In certain embodiments, the disease is cancer. In certain embodiments, the disease is heart failure. In certain embodiments, the disease is fibrosis. Fibrosis results from the development of excess fibrous connective tissue in an organ or tissue in response to damage or injury. Left untreated, fibrosis can lead to a variety of conditions of the heart, lungs, kidney, liver, and skin, among other tissues.

It is discovered herein that fibroblast-derived miR-21 plays a critical role in fibrosis. Enhancement of miR-21 levels promoted fibroblast survival, whereas suppression of endogenous miR-21 induced apoptotic cell death. Thus, herein identified is a mechanism by which miR-21 regulates fibroblast survival. Aberrant fibroblast proliferation and survival may lead to fibrosis. Accordingly, modified oligonucleotides complementary to miR-21 are pharmaceutical agents for the treatment of fibrosis. In certain embodiments, a modified oligonucleotide complementary to miR-21 is an antisense oligonucleotide complementary to miR-21.

The inventors demonstrate a critical role of fibroblast-derived miR-21 and SPRY1 in the heart (FIG. 3h). The data suggest that stress-induced and miRNA-mediated activation of ERK-MAPkinase activity may importantly regulate cardiac fibrosis. This study represents the first example of a microRNA therapeutic application in a disease model. Specifically antagonizing miR-21 prevented the structural and functional deterioration in a murine model. These findings suggest a new therapeutic entry point for heart failure and show the broad therapeutic potential of microRNA antagonists.

In one aspect the present invention relates to the use of miR-21, an antisense oligonucleotide against miR-21 and/or a target of miR-21 for the manufacture of a medicament for the treatment and/or prevention of fibrosis and/or fibrosis related diseases.

The invention particularly concerns cardiac specific diseases involving fibrosis (=fibrosis related diseases), like cardiac hypertrophy, hypertensive heart disease, diatolic and systolic heart failure, storage-diseases related to heart, such as M. Fabry, cardiomyopathies, e.g. dilatative cardiomyopathy, hypertrophic cardio-myopathy with and without obstruction, restrictive cardiomyopathy, arrhythmogenic right ventricular cardiomyopathy and other forms of cardiomyopathy, like e.g. diabetic cardiomyopathy, constrictive pericarditis, coronary artery disease, myocardial infarction, acute and chronic right heart failure, cardiac arrhythmias due to fibrosis, myocarditis-related fibrosis, diseases of the heart valves leading to valve stenosis or insufficiency (e.g. sclerosis), e.g. mitral valve stenosis and/or insufficiency, aortic valve stenosis and/or insufficiency, tricuspidal valve stenosis and/or insufficiency, pulmonary valve stenosis and/or insufficiency.

In a further aspect the invention concerns other diseases involving fibrosis (=fibrosis related diseases), not related to the cardiac system. Non-limiting examples are lung fibrosis, chronic obstructive lung diseases, pulmonary hypertension, liver fibrosis due to a toxic surrounding, hepatitis and/or secondary to right heart failure, skin fibrosis, e.g. development of keloids after injury, blood vessel-related diseases, such as arterial stiffness related to age or hypertension, mediasclerosis, arteriosclerosis, age-related fibrosis of different organs, gut sclerosis, e.g. during Crohn's disease, systemic sclerosis and CREST syndrome etc., kidney fibrosis, neoplastic fibrosis and/or rheumatoid arthritis.

Further well-known fibrosis-related diseases and disorders are e.g. endomyocardial fibrosis and idiopathic myocardiopathy, cirrhosis which can result from fibrosis of the liver, idiopathic pulmonary fibrosis of the lung, diffuse paren-chymal lung disease, mediastinal fibrosis, myelofibrosis, postvasectomy pain syndrome, retroperitoneal fibrosis and nephrogenic systemic fibrosis.

All aspects of the invention, in particular the aspects mentioned in the accompanying claims may be used for the diagnosis, treatment and/or prevention of the above mentioned diseases, disorders and conditions, which are given as possible examples. The list is not limiting.

In one embodiment, the invention relates to strategies for modulating miR-21. In another embodiment, the invention relates to strategies for modulating, e.g. overexpressing and/or upregulating targets of miR-21. Possible modulations are implantable devices, like viral vectors and liposomal formulations, etc, gene transfer systems, sponges and the like.

Sprouty (SPRY1) is herein identified as a target of miR-21. Both miR-21 and SPRY1 are expressed in cardiac fibroblasts, among other cell types. Increasing miR-21 expression in cardiac fibroblasts induced a strong repression of SPRY protein expression and further increased ERK-MAPkinase activation. In a preferred embodiment the target is selected from the group consisting of Sprouty1 (SPRY1), in particular SEQ ID NO: 7 or SEQ ID NO: 8, Tgfbi, Krit1, Pitx2, Fasl, Nfib, Lnx1 and Rtn4.

In one aspect the present invention relates to an antisense oligonucleotide against (or complementary to) SEQ ID NO: 2 to SEQ ID NO: 4, Sprouty1 (SPRY1), in particular SEQ ID NO: 7 or SEQ ID NO: 8, Tgfbi, Krit1, Pitx2, Fasl, Nfib, Lnx1 and/or Rtn4 for the diagnosis, treatment and/or prevention of fibrosis and/or fibrosis related diseases. In certain aspects, an antisense oligonucleotide complementary to a target selected from the group consisting of Sprouty1 (SPRY1), in particular SEQ ID NO: 7 or SEQ ID NO: 8, Tgfbi, Krit1, Pitx2, Fasl, Nfib, Lnx1 and/or Rtn4, interferes with the ability of a microRNA, such as miR-21, to bind to a target site and inhibit expression of the selected target. In certain aspects, such an antisense oligonucleotide comprises one or more nucleoside modifications.

In one aspect the present invention relates to a cell deficient for miR-21, SEQ ID NO: 2 to SEQ ID NO: 4, Sprouty1 (SPRY1), in particular SEQ ID NO: 7 or SEQ ID NO: 8, Tgfbi, Krit1, Pitx2, Fasl, Nfib, Lnx1 and/or Rtn4.

In one aspect the invention relates to a non-human mammal knock-out organism deficient for miR-21, SEQ ID NO: 2 to SEQ ID NO: 4, Sprouty1 (SPRY1), in particular SEQ ID NO: 7 or SEQ ID NO: 8, Tgfbi, Krit1, Pitx2, Fasl, Nfib, Lnx1 and/or Rtn4 as a disease model for fibrosis and/or fibrosis related diseases. Also encompassed are transgenic animals, in particular non-human mammals which overexpress miR-21.

It is discovered herein that fibroblast-derived miR-21 contributes to heart failure. Analysis of left ventricular cardiac tissue samples from subjects with end-stage heart failure due to idiopathic dilated cardiomyopathy revealed increased miR-21 expression and repressed SPRY1 protein expression. Additionally, ERK-MAPkinase was activated in samples from these subjects, as evidenced by an increased phosphor-ERK/ERK ratio. It is discovered herein that in an animal model of heart failure the administration of a modified oligonucleotide complementary to miR-21 resulted in significant attenuation of cardiac fibrosis. Heart failure is characterized by, among other parameters, cardiac fibrosis. Accordingly, modified oligonucleotides complementary to miR-21 are pharmaceutical agents for the treatment of cardiac fibrosis.

It is also discovered herein that in an animal model of heart failure, the attenuation of cardiac fibrosis is accompanied by attenuation of heart weight increases. Further, assessment of cardiac function by echocardiography revealed that the administration of a modified oligonucleotide complementary to miR-21 prevented left ventricular dilation and normalized parameters of fractional shortening. Heart failure may be characterized by, among other parameters, heart weight increases, left ventricular dilation, and impairment of fractional shortening. Accordingly, modified oligonucleotides complementary to miR-21 are therapeutic agents for the treatment, amelioration, and prevention of heart failure associated with cardiac fibrosis.

In one aspect the present invention relates to a promoter region of a microRNA (miRNA) comprising a modification of a calcium/cAMP response element protein (CREB) and/or serum response factor (SRF) binding site for diagnosis, prevention and/or therapy of fibrosis and/or fibrosis related diseases.

In one embodiment, the promoter region, the gene of mirR-21 itself and/or the 3'UTR of various messenger RNAs may contain polymorphisms, mutations, in particular point mutations, deletions, truncations and/or inversion. All these amendments to the wild-type sequence lead to the de novo formation of a novel miR-21 binding site or to the deletion of a miR-21 binding site. In another embodiment the modification of the promoter region is selected from the group consisting of a point mutation, a truncation, a deletion and an inversion. Further, the promoter region can be selected from the group consisting of SEQ ID NO: 2 to SEQ ID NO: 4.

Diagnostic Applications

In one aspect the present invention relates to the use of miR-21, an antisense oligonucleotide against miR-21 and/or a target of miR-21 for the diagnosis of fibrosis and/or fibrosis related diseases. An antisense oligonucleotide is to be understood as a oligonucleotide which has a certain sequence complementary to another sequence, in particular a sequence complementary to miR-21. A target of miR-21 may also be understood to encompass a downstream target of miR-21. It is important to note that an inhibition of miR-21, e.g. via an oligonucleotide with a sequence at least complementary to miR-21 will lead to a derepression or even an overexpression of targets of miR-21, like Sprouty and the like.

In one aspect the invention relates a method for diagnosing fibrosis and/or fibrosis related diseases comprising the steps of:
(a) providing a sample of an patient supposed to suffer from fibrosis and/or fibrosis related diseases;
(b) measuring the expression of miR-21, Sprouty1 (SPRY1), in particular SEQ ID NO: 7 or SEQ ID NO: 8, Tgfbi, Krit1, Pitx2, Fasl, Nfib, Lnx1 and/or Rtn4;
wherein an elevated level of miR-21 and/or a reduced level of Sproutyl (SPRY1), in particular SEQ ID NO: 7 or SEQ ID NO: 8, Tgfbi, Krit1, Pitx2, Fasl, Nfib, Lnx1 and/or Rtn4 in comparison to a control sample indicates fibrosis and/or fibrosis related diseases or a predisposition thereof.

In one aspect the present invention relates to a method for screening of a pharmaceutically active compound for the treatment and/or the prevention of fibrosis and/or fibrosis related diseases or a predisposition thereof, comprising the steps of:
(a) Providing a sample containing miR-21, Sprouty1 (SPRY1), in particular SEQ ID NO: 7 or SEQ ID NO: 8, Tgfbi, Krit1, Pitx2, Fasl, Nfib, Lnx1 and/or Rtn4;
(b) Contacting a candidate substance with the sample;
(c) Determining the effect of the candidate substance on the sample;
wherein an alteration of miR-21, Sprouty1 (SPRY1), in particular SEQ ID NO: 7 or SEQ ID NO: 8, Tgfbi, Krit1, Pitx2, Fasl, Nfib, Lnx1 and/or Rtn4 indicates a pharmaceutically active compound.

Certain Diseases and Conditions

Provided herein are methods for treating a subject having or suspected of having fibrosis. Also provided are methods for treating a subject identified as having or suspected of having fibrosis. In certain embodiments, such methods comprise administering to a subject a modified oligonucleotide having a nucleobase sequence complementary to a miRNA or a precursor thereof. In certain embodiments, the miRNA is miR-21.

Further provided herein are methods for preventing fibrosis in a subject at risk for developing fibrosis. In certain embodiments, such methods comprise administering to a subject at risk for developing fibrosis a modified oligonucleotide having a nucleobase sequence complementary to a miRNA or a precursor thereof. In certain embodiments, the miRNA is miR-21.

In certain embodiments, the fibrosis is liver fibrosis. In certain embodiments, the fibrosis is lung fibrosis. In certain embodiments the fibrosis is skin fibrosis. In certain embodiments the fibrosis is cardiac fibrosis. In certain embodiments the fibrosis is kidney fibrosis. In certain embodiments the fibrosis is lung fibrosis. In certain embodiments the fibrosis is age-related fibrosis. In certain embodiments the fibrosis is spleen fibrosis.

In certain embodiments, the subject having or suspected of having fibrosis has at least one cardiac disease or condition. In certain embodiments, a subject identified as having or suspected of having fibrosis has at least one cardiac disease or condition. In certain embodiments, such methods comprise administering to a subject a modified oligonucleotide having a nucleobase sequence complementary to a miRNA or a precursor thereof. In certain embodiments, the miRNA is miR-21.

In certain embodiments, a cardiac disease or condition is cardiac hypertrophy. In certain embodiments, a cardiac disease or condition is cardiomyopathy. In certain embodiments, cardiomyopathy is dilatative cardiomyopathy, hypertrophic cardiomyopathy with obstruction, hypertrophic cardiomyopathy without obstruction, restrictive cardiomyopathy, arrhythmogenic right ventricular cardiomyopathy, or diabetic cardiomyopathy.

In certain embodiments, a cardiac disease or condition is coronary artery disease. In certain embodiments, a cardiac disease or condition is heart-related storage disease, constrictive pericarditis, acute myocardial infarction, chronic myocardial infarction, cardiac arrhythmia, or myocarditis-related fibrosis.

In certain embodiments, a cardiac disease or condition is heart failure. In certain embodiments, heart failure is hypertensive heart failure, diastolic heart failure, systolic heart failure, or right heart failure.

In certain embodiments, a cardiac disease or condition is heart valve disease. In certain embodiments, heart valve disease is mitral valve stenosis, aortic valve stenosis, tricuspidal valve stenosis, or pulmonary valve stenosis. In certain embodiments, the heart valve disease is mitral valve insufficiency, aortic valve insufficiency, tricuspidal valve insufficiency, or pulmonary valve insufficiency.

Provided herein are methods for treating a subject having or suspected of having fibrosis, wherein the subject has a liver disease or condition. In certain embodiments, a subject identified as having or suspected of having fibrosis has at least one liver disease or condition. In certain embodiments, such methods comprise administering to a subject a modified oligonucleotide having a nucleobase sequence complementary to a miRNA or a precursor thereof. In certain embodiments, the miRNA is miR-21. In certain embodiments, a liver disease or condition is chronic liver injury. In certain embodiments, a liver disease or condition is hepatitis virus infection. In certain embodiments, a hepatitis infection is hepatitis C virus infection. In certain embodiments a liver disease or condition is non-alcoholic steatohepatitis. In certain embodiments a liver disease or condition is cirrhosis.

Provided herein are methods for the treatment of a subject having or suspected of having fibrosis, wherein the subject has at least one lung disease or condition. Also provided herein are methods for the treatment of a subject identified as having or suspected of having fibrosis, wherein the subject has at least one lung disease or condition. In certain embodiments, such methods comprise administering to a subject a modified oligonucleotide having a nucleobase sequence which is complementary to a miRNA or a precursor thereof. In certain embodiments, the miRNA is miR-21. In certain embodiments a lung disease or condition is chronic obstructive lung disease.

Provided herein are methods for the treatment of a subject having or suspected of having fibrosis, wherein the subject has at least one other disease or condition. Also provided herein are methods for the treatment of a subject identified as having or suspected of having fibrosis, wherein the subject has at least one other disease or condition. In certain embodiments, such methods comprise administering to a subject a modified oligonucleotide having a nucleobase sequence which is complementary to a miRNA or a precursor thereof. In certain embodiments, the miRNA is miR-21. In certain embodiments one other disease or condition is pulmonary hypertension. In certain embodiments one other disease or condition is a blood vessel-related disease. In certain such embodiments a blood-vessel related disease is arterial stiffness, mediasclerosis, or arteriosclerosis. In certain embodiments one other disease or condition is gut sclerosis. In certain embodiments another disease or condition is systemic sclerosis. In certain embodiments one other disease or condition is retroperitoneal fibrosis, proliferative fibrosis, neoplastic fibrosis, nephrogenic systemic fibrosis, injection fibrosis, mediastinal fibrosis, myelofibrosis, post-vasectomy pain syndrome, or rheumatoid arthritis.

Provided herein are methods for treating a subject having a fibroproliferative disorder. In certain embodiments such methods comprise administering to a subject having or suspected of having a fibroproliferative disorder a modified oligonucleotide having a nucleobase sequence which is complementary to a miRNA or a precursor thereof. In certain embodiments, the miRNA is miR-21.

The invention additionally relates to miRNA-21 based treatments for cancer that involve targeting specific cancers by modulation of SPRY-1-mediated ERK signalling in cancer cells. It is known that miR-21 is overexpressed in many different cancer types including esophageal, colon adenocarcinoma, breast cancer, gliomas, glioblastomas, ovarian cancer, hepatocellular cancer, head and neck cancer, chronic lymphocytic leukemia, pancreatic cancer, just to name some of them.

Therefore, the invention also relates to the diagnosis, prevention and/or therapy of the above mentioned cancer types. All features mentioned in the claims may be combined with the disclosure of these cancer types.

Certain Routes of Administration

In certain embodiments, administering to a subject comprises parenteral administration. In certain embodiments, administering to a subject comprises intravenous administration. In certain embodiments, administering to a subject comprises subcutaneous administration.

In certain embodiments, administering to a subject comprises intraarterial administration. In certain embodiments, administering to a subject comprises intracardial administration. Suitable means for intracardial administration include the use of a catheter, or administration during open heart surgery.

In certain embodiments, administration includes pulmonary administration. In certain embodiments, pulmonary administration comprises delivery of aerosolized oligonucleotide to the lung of a subject by inhalation. Following inhalation by a subject of aerosolized oligonucleotide, oligonucleotide distributes to cells of both normal and inflamed lung tissue, including alveolar macrophages, eosinophils, epithelium, blood vessel endothelium, and bronchiolar epithelium. A suitable device for the delivery of a pharmaceutical composition comprising a modified oligonucleotide includes, but is not limited to, a standard nebulizer device. Formulations and methods for modulating the size of droplets using nebulizer devices to target specific portions of the respiratory tract and lungs are well known to those skilled in the art. Additional suitable devices include dry powder inhalers or metered dose inhalers.

In certain embodiments, pharmaceutical compositions are administered to achieve local rather than systemic exposures. For example, pulmonary administration delivers a pharmaceutical composition to the lung, with minimal systemic exposure.

Additional suitable administration routes include, but are not limited to, oral, rectal, transmucosal, intestinal, enteral, topical, suppository, intrathecal, intraventricular, intraperitoneal, intranasal, intraocular, intramuscular, intramedullary, and intratumoral.

Certain Clinical Outcomes

In certain embodiments, the methods herein provide a clinically desirable outcome to a subject having or suspected of having fibrosis.

In certain embodiments, a clinically desirable outcome is the amelioration of heart weight increase. In certain such embodiments, a clinically desirable outcome is the amelioration of left ventricular dilation. In certain embodiments a clinically desirable outcome is the amelioration of impaired fractional shortening. In certain embodiments a clinically desirable outcome is the prevention of heart weight increase. In certain such embodiments, a clinically desirable outcome is the prevention of left ventricular dilation. In certain embodiments a clinically desirable outcome is the prevention of impaired fractional shortening.

In certain embodiments a clinically desirable outcome is improved cardiac function.

In certain embodiments a clinically desirable outcome is the amelioration of fibrosis. In certain embodiments a clinically desirable outcome is the slowing of further progression of fibrosis. In certain embodiments a clinically desirable outcome is the halting of further progression of fibrosis. In certain embodiments a clinically desirable outcome is a reduction in fibrosis. In certain embodiments a clinically desirable outcome is a reduction in collagen content.

In certain embodiments a therapeutically desirable outcome is improved liver function. Liver function may be assessed by liver function tests, which measure, among other things, blood levels of liver transaminases. In certain embodiments, a subject having abnormal liver function has elevated blood liver transaminases. Blood liver transaminases include alanine aminotransferase (ALT) and aspartate aminotransferase (AST). In certain embodiments, a subject having abnormal liver function has elevated blood bilirubin. In certain embodiments, a subject has abnormal blood albumin levels. In certain embodiments, the methods provided herein alter ALT, AST, bilirubin and/or albumin levels in the blood such that one or more of these levels is closer to normal limits.

In certain embodiments, a subject's liver function is assessed by the Child-Pugh classification system, which defines three classes of liver function. In this classification system, points are assigned to measurements in one of five categories: bilirubin levels, albumin levels, prothrombin time, ascites, and encephalopathy. One point is assigned per each of the following characteristics present: blood bilirubin of less than 2.0 mg/dl; blood albumin of greater than 3.5 mg/dl; a prothrombin time of less than 1.7 international normalized ratio (INR); ascites is absent; or encephalopathy is absent. Two points are assigned per each of the following characteristics present: blood bilirubin of 2-3 mg/dl; blood bilirubin of 3.5 to 2.8 mg/dl; prothrombin time of 1.7-2.3 INR; ascites is mild to moderate; or encephalopathy is mild. Three points are assigned per each of the following characteristics present: bilirubin of greater than 3.0 mg/dl; blood albumin of less than 2.8 mg/dl; prothrombin time of greater than 2.3 INR; ascites is severe to refractory; or encephalopathy is severe. The scores are added and Class A is assigned for a score of 5-6 points, Class B is assigned for a score of 7-9 points, and Class C is assigned for a score of 10-15 points. In certain embodiments, the methods provided herein result in an improvement in liver function as measured by the Child-Pugh classification system.

Certain Cellular Phenotypes

Provided herein are methods for inhibiting fibroblast cell proliferation. Also provided herein are methods for stimulating apoptosis in a fibroblast cell. Further provided herein are methods for increasing Sprouty 1 protein in a fibroblast cell. In certain embodiments, such methods comprise contacting a fibroblast with a compound comprising a modified oligonucleotide and having a nucleobase sequence which is complementary to a miRNA or a precursor thereof. In certain embodiments, the miRNA is miR-21.

In certain embodiments, the fibroblast cell is in vitro. In certain embodiments, the fibroblast cell is in vivo. In certain embodiments, the contacting occurs in vitro. In certain embodiments, the contacting occurs in vivo. In certain embodiments, the contacting occurs ex vivo.

Certain Additional Therapies

Treatments for fibrosis may comprise more than one therapy. As such, in certain embodiments provided herein are methods for treating a subject having or suspected of having fibrosis comprising administering at least one therapy in addition to administering a modified oligonucleotide having a nucleobase sequence complementary to a miRNA or a precursor thereof.

In certain embodiments, the methods provided herein comprise administering one or more additional pharmaceutical agents. In certain embodiments, additional pharmaceutical agents include, but are not limited to, diuretics (e.g. sprionolactone, eplerenone, furosemide), inotropes (e.g. dobutamine, milrinone), digoxin, vasodilators, angiotensin II converting enzyme (ACE) inhibitors (e.g. are captopril, enalapril, lisinopril, benazepril, quinapril, fosinopril, and ramipril), angiotensin II receptor blockers (ARB) (e.g. candesartan, irbesartan, olmesartan, losartan, valsartan, telmisartan, eprosartan), calcium channel blockers, isosorbide dinitrate, hydralazine, nitrates (e.g. isosorbide mononitrate, isosorbide dinitrate), hydralazine, beta-blockers (e.g. carvedilol, metoprolol), and natriuretic peptides (e.g. nesiritide).

In certain embodiments, an additional therapy may be a pharmaceutical agent that enhances the body's immune system, including low-dose cyclophosphamide, thymostimulin, vitamins and nutritional supplements (e.g., antioxidants, including vitamins A, C, E, beta-carotene, zinc, selenium, glutathione, coenzyme Q-10 and echinacea), and vaccines, e.g., the immunostimulating complex (ISCOM), which comprises a vaccine formulation that combines a multimeric presentation of antigen and an adjuvant.

In certain such embodiments, the additional therapy is selected to treat or ameliorate a side effect of one or more pharmaceutical compositions of the present invention. Such side effects include, without limitation, injection site reactions, liver function test abnormalities, renal function abnormalities, liver toxicity, renal toxicity, central nervous system abnormalities, and myopathies. For example, increased aminotransferase levels in serum may indicate liver toxicity or liver function abnormality. For example, increased bilirubin may indicate liver toxicity or liver function abnormality.

In certain embodiments, one or more pharmaceutical compositions of the present invention and one or more other pharmaceutical agents are administered at the same time. In certain embodiments, one or more pharmaceutical compositions of the present invention and one or more other pharmaceutical agents are administered at different times. In certain embodiments, one or more pharmaceutical compositions of the present invention and one or more other pharmaceutical agents are prepared together in a single formulation. In certain embodiments, one or more pharmaceutical compositions of the present invention and one or more other pharmaceutical agents are prepared separately.

Certain Pharmaceutical Compositions

In certain embodiments, a compound comprising a modified oligonucleotide complementary to a miRNA, or precursor thereof, described herein is prepared as a pharmaceutical composition for the treatment of fibrosis. In certain embodiments, a compound comprising a modified oligonucleotide having a nucleobase sequence complementary to a miRNA or a precursor thereof is prepared as a pharmaceutical composition for the prevention of fibrosis.

In certain embodiments, a pharmaceutical composition of the present invention is administered in the form of a dosage unit (e.g., tablet, capsule, bolus, etc.). In certain embodiments, such pharmaceutical compositions comprise a modified oligonucleotide in a dose selected from 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 205 mg, 210 mg, 215 mg, 220 mg, 225 mg, 230 mg, 235 mg, 240 mg, 245 mg, 250 mg, 255 mg, 260 mg, 265 mg, 270 mg, 270 mg, 280 mg, 285 mg, 290 mg, 295 mg, 300 mg, 305 mg, 310 mg, 315 mg, 320 mg, 325 mg, 330 mg, 335 mg, 340 mg, 345 mg, 350 mg, 355 mg, 360 mg, 365 mg, 370 mg, 375 mg, 380 mg, 385 mg, 390 mg, 395 mg, 400 mg, 405 mg, 410 mg, 415 mg, 420 mg, 425 mg, 430 mg, 435 mg, 440 mg, 445 mg, 450 mg, 455 mg, 460 mg, 465 mg, 470 mg, 475 mg, 480 mg, 485 mg, 490 mg, 495 mg, 500 mg, 505 mg, 510 mg, 515 mg, 520 mg, 525 mg, 530 mg, 535 mg, 540 mg, 545 mg, 550 mg, 555 mg, 560 mg, 565 mg, 570 mg, 575 mg, 580 mg, 585 mg, 590 mg, 595 mg, 600 mg, 605 mg, 610 mg, 615 mg, 620 mg, 625 mg, 630 mg, 635 mg, 640 mg, 645 mg, 650 mg, 655 mg, 660 mg, 665 mg, 670 mg, 675 mg, 680 mg, 685 mg, 690 mg, 695 mg, 700 mg, 705 mg, 710 mg, 715 mg, 720 mg, 725 mg, 730 mg, 735 mg, 740 mg, 745 mg, 750 mg, 755 mg, 760 mg, 765 mg, 770 mg, 775 mg, 780 mg, 785 mg, 790 mg, 795 mg, and 800 mg. In certain such embodiments, a pharmaceutical composition of the present invention comprises a dose of modified oligonucleotide selected from 25 mg, 50 mg, 75 mg, 100 mg, 150 mg, 200 mg, 250 mg, 300 mg, 350 mg, 400 mg, 500 mg, 600 mg, 700 mg, and 800 mg.

In certain embodiments, a pharmaceutical agent is sterile lyophilized modified oligonucleotide that is reconstituted with a suitable diluent, e.g., sterile water for injection or sterile saline for injection. The reconstituted product is administered as a subcutaneous injection or as an intravenous infusion after dilution into saline. The lyophilized drug product consists of a modified oligonucleotide which has been prepared in water for injection, or in saline for injection, adjusted to pH 7.0-9.0 with acid or base during preparation, and then lyophilized. The lyophilized modified oligonucleotide may be 25-800 mg of a modified oligonucleotide. It is understood that this encompasses 25, 50, 75, 100, 125, 150, 175, 200, 225, 250, 275, 300, 325, 350, 375, 425, 450, 475, 500, 525, 550, 575, 600, 625, 650, 675, 700, 725, 750, 775, and 800 mg of modified lyophilized oligonucleotide. The lyophilized drug product may be packaged in a 2 mL Type I, clear glass vial (ammonium sulfate-treated), stoppered with a bromobutyl rubber closure and sealed with aluminum FLIP-OFF® overseal.

In certain embodiments, the compositions of the present invention may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the oligonucleotide(s) of the formulation.

In certain embodiments, pharmaceutical compositions of the present invention comprise one or more modified oligonucleotides and one or more excipients. In certain such embodiments, excipients are selected from water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, a pharmaceutical composition of the present invention is prepared using known techniques, including, but not limited to mixing, dissolving, granulating, dragee-making, levigating, emulsifying, encapsulating, entrapping or tabletting processes.

In certain embodiments, a pharmaceutical composition of the present invention is a liquid (e.g., a suspension, elixir and/or solution). In certain of such embodiments, a liquid pharmaceutical composition is prepared using ingredients known in the art, including, but not limited to, water, glycols, oils, alcohols, flavoring agents, preservatives, and coloring agents.

In certain embodiments, a pharmaceutical composition of the present invention is a solid (e.g., a powder, tablet, and/or capsule). In certain of such embodiments, a solid pharmaceutical composition comprising one or more oligonucleotides is prepared using ingredients known in the art, including, but not limited to, starches, sugars, diluents, granulating agents, lubricants, binders, and disintegrating agents.

In certain embodiments, a pharmaceutical composition of the present invention is formulated as a depot preparation. Certain such depot preparations are typically longer acting than non-depot preparations. In certain embodiments, such preparations are administered by implantation (for example subcutaneously or intramuscularly) or by intramuscular injection. In certain embodiments, depot preparations are prepared using suitable polymeric or hydrophobic materials (for example an emulsion in an acceptable oil) or ion exchange resins, or as sparingly soluble derivatives, for example, as a sparingly soluble salt.

In certain embodiments, a pharmaceutical composition of the present invention comprises a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, a pharmaceutical composition of the present invention comprises one or more tissue-specific delivery molecules designed to deliver the one or more pharmaceutical agents of the present invention to specific tissues or cell types. For example, in certain embodiments, pharmaceutical compositions include liposomes coated with a tissue-specific antibody.

In certain embodiments, a pharmaceutical composition of the present invention comprises a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™ and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, a pharmaceutical composition of the present invention comprises a sustained-release system. A non-limiting example of such a sustained-release system is a semi-permeable matrix of solid hydrophobic polymers. In certain embodiments, sustained-release systems may, depending on their chemical nature, release pharmaceutical agents over a period of hours, days, weeks or months.

In certain embodiments, a pharmaceutical composition of the present invention is prepared for oral administration. In certain of such embodiments, a pharmaceutical composition is formulated by combining one or more compounds comprising a modified oligonucleotide with one or more pharmaceutically acceptable carriers. Certain of such carriers enable pharmaceutical compositions to be formulated as tablets, pills, dragees, capsules, liquids, gels, syrups, slurries, suspensions and the like, for oral ingestion by a subject. In certain embodiments, pharmaceutical compositions for oral use are obtained by mixing oligonucleotide and one or more solid excipient. Suitable excipients include, but are not limited to, fillers, such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). In certain embodiments, such a mixture is optionally ground and auxiliaries are optionally added. In certain embodiments, pharmaceutical compositions are formed to obtain tablets or dragee cores. In certain embodiments, disintegrating agents (e.g., cross-linked polyvinyl pyrrolidone, agar, or alginic acid or a salt thereof, such as sodium alginate) are added.

In certain embodiments, dragee cores are provided with coatings. In certain such embodiments, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to tablets or dragee coatings.

In certain embodiments, pharmaceutical compositions for oral administration are push-fit capsules made of gelatin. Certain of such push-fit capsules comprise one or more pharmaceutical agents of the present invention in admixture with one or more filler such as lactose, binders such as starches, and/or lubricants such as talc or magnesium stearate and, optionally, stabilizers. In certain embodiments, pharmaceutical compositions for oral administration are soft, sealed capsules made of gelatin and a plasticizer, such as glycerol or sorbitol. In certain soft capsules, one or more pharmaceutical agents of the present invention are be dissolved or suspended in suitable liquids, such as fatty oils, liquid paraffin, or liquid polyethylene glycols. In addition, stabilizers may be added.

In certain embodiments, pharmaceutical compositions are prepared for buccal administration. Certain of such pharmaceutical compositions are tablets or lozenges formulated in conventional manner.

In certain embodiments, a pharmaceutical composition is prepared for administration by injection (e.g., intravenous, subcutaneous, intramuscular, etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain substances that increase the viscosity of the suspension, such as sodium carboxymethyl cellulose, sorbitol, or dextran. Optionally, such suspensions may also contain suitable stabilizers or agents that increase the solubility of the pharmaceutical agents to allow for the preparation of highly concentrated solutions.

In certain embodiments, a pharmaceutical composition is prepared for transmucosal administration. In certain of such embodiments penetrants appropriate to the barrier to be permeated are used in the formulation. Such penetrants are generally known in the art.

In certain embodiments, a pharmaceutical composition is prepared for administration by inhalation. Certain of such pharmaceutical compositions for inhalation are prepared in the form of an aerosol spray in a pressurized pack or a nebulizer. Certain of such pharmaceutical compositions comprise a propellant, e.g., dichlorodifluoromethane, trichlorofluoromethane, dichlorotetrafluoroethane, carbon dioxide or other suitable gas. In certain embodiments using a pressurized aerosol, the dosage unit may be determined with a valve that delivers a metered amount. In certain embodiments, capsules and cartridges for use in an inhaler or insufflator may be formulated. Certain of such formulations comprise a powder mixture of a pharmaceutical agent of the invention and a suitable powder base such as lactose or starch.

In certain embodiments, a pharmaceutical composition is prepared for rectal administration, such as a suppositories or retention enema. Certain of such pharmaceutical compositions comprise known ingredients, such as cocoa butter and/or other glycerides.

In certain embodiments, a pharmaceutical composition is prepared for topical administration. Certain of such pharmaceutical compositions comprise bland moisturizing bases, such as ointments or creams. Exemplary suitable ointment bases include, but are not limited to, petrolatum, petrolatum plus volatile silicones, and lanolin and water in oil emulsions. Exemplary suitable cream bases include, but are not limited to, cold cream and hydrophilic ointment.

In certain embodiments, a pharmaceutical composition of the present invention comprises a modified oligonucleotide in a therapeutically effective amount. In certain embodiments, the therapeutically effective amount is sufficient to prevent, alleviate or ameliorate symptoms of a disease or to prolong the survival of the subject being treated. Determination of a therapeutically effective amount is well within the capability of those skilled in the art.

In certain embodiments, one or more modified oligonucleotides of the present invention is formulated as a prodrug. In certain embodiments, upon in vivo administration, a prodrug is chemically converted to the biologically, pharmaceutically or therapeutically more active form of a modified oligonucleotide. In certain embodiments, prodrugs are useful because they are easier to administer than the corresponding active form. For example, in certain instances, a prodrug may be more bioavailable (e.g., through oral administration) than is the corresponding active form. In certain instances, a prodrug may have improved solubility compared to the corresponding active form. In certain embodiments, prodrugs are less water soluble than the corresponding active form. In certain instances, such prodrugs possess superior transmittal across cell membranes, where water solubility is detrimental to mobility. In certain embodiments, a prodrug is an ester. In certain such embodiments, the ester is metabolically hydrolyzed to carboxylic acid upon administration. In certain instances the carboxylic acid containing compound is the corresponding active form. In certain embodiments, a prodrug comprises a short peptide (polyaminoacid) bound to an acid group. In certain of such embodiments, the peptide is cleaved upon administration to form the corresponding active form.

In certain embodiments, a prodrug is produced by modifying a pharmaceutically active compound such that the active compound will be regenerated upon in vivo administration. The prodrug can be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) Medicinal Chemistry A Biochemical Approach, Oxford University Press, New York, pages 388-392).

Certain Compounds

In certain embodiments, the methods provided herein comprise administration of a compound comprising a modified oligonucleotide. In certain embodiments, the compound consists of a modified oligonucleotide.

In certain such embodiments, a compound comprises a modified oligonucleotide hybridized to a complementary strand, i.e. a compound comprises a double-stranded oligomeric compound. In certain embodiments, the hybridization of a modified oligonucleotide to a complementary strand forms at least one blunt end. In certain such embodiments, the hybridization of a modified oligonucleotide to a complementary strand forms a blunt end at each terminus of the double-stranded oligomeric compound. In certain embodiments, a terminus of a modified oligonucleotide comprises one or more additional linked nucleosides relative to the number of linked nucleosides of the complementary strand. In certain embodiments, the one or more additional nucleosides are at the 5' terminus of a modified oligonucleotide. In certain embodiments, the one or more additional nucleosides are at the 3' terminus of a modified oligonucleotide. In certain embodiments, at least one nucleobase of a nucleoside of the one or more additional nucleosides is complementary to the target RNA. In certain embodiments, each nucleobase of each one or more additional nucleosides is complementary to the target RNA. In certain embodiments, a terminus of the complementary strand comprises one or more additional linked nucleosides relative to the number of linked nucleosides of a modified oligonucleotide. In certain embodiments, the one or more additional linked nucleosides are at the 3' terminus of the complementary strand. In certain embodiments, the one or more additional linked nucleosides are at the 5' terminus of the complementary strand. In certain embodiments, two additional linked nucleosides are linked to a terminus. In certain embodiments, one additional nucleoside is linked to a terminus.

In certain embodiments, a compound comprises a modified oligonucleotide conjugated to one or more moieties which enhance the activity, cellular distribution or cellular uptake of the resulting antisense oligonucleotides. In certain such embodiments, the moiety is a cholesterol moiety or a lipid moiety. Additional moieties for conjugation include carbohydrates, phospholipids, biotin, phenazine, folate, phenanthridine, anthraquinone, acridine, fluoresceins, rhodamines, coumarins, and dyes. In certain embodiments, a conjugate group is attached directly to a modified oligonucleotide. In certain embodiments, a conjugate group is attached to a modified oligonucleotide by a linking moiety selected from amino, hydroxyl, carboxylic acid, thiol, unsaturations (e.g., double or triple bonds), 8-amino-3,6-dioxaoctanoic acid (ADO), succinimidyl 4-(N-maleimidomethyl)cyclohexane-1-carboxylate (SMCC), 6-aminohexanoic acid (AHEX or AHA), substituted C1-C10 alkyl, substituted or unsubstituted C2-C10 alkenyl, and substituted or unsubstituted C2-C10 alkynyl. In certain such embodiments, a substituent group is selected from hydroxyl, amino, alkoxy, carboxy, benzyl, phenyl, nitro, thiol, thioalkoxy, halogen, alkyl, aryl, alkenyl and alkynyl.

In certain such embodiments, the compound comprises a modified oligonucleotide having one or more stabilizing groups that are attached to one or both termini of a modified oligonucleotide to enhance properties such as, for example, nuclease stability. Included in stabilizing groups are cap structures. These terminal modifications protect a modified oligonucleotide from exonuclease degradation, and can help in delivery and/or localization within a cell. The cap can be present at the 5'-terminus (5'-cap), or at the 3'-terminus (3'-cap), or can be present on both termini. Cap structures include, for example, inverted deoxy abasic caps.

Suitable cap structures include a 4',5'-methylene nucleotide, a 1-(beta-D-erythrofuranosyl) nucleotide, a 4'-thio nucleotide, a carbocyclic nucleotide, a 1,5-anhydrohexitol nucleotide, an L-nucleotide, an alpha-nucleotide, a modified base nucleotide, a phosphorodithioate linkage, a threo-pentofuranosyl nucleotide, an acyclic 3',4'-seco nucleotide, an acyclic 3,4-dihydroxybutyl nucleotide, an acyclic 3,5-dihydroxypentyl nucleotide, a 3'-3'-inverted nucleotide moiety, a 3'-3'-inverted abasic moiety, a 3'-2'-inverted nucleotide moiety, a 3'-2'-inverted abasic moiety, a 1,4-butanediol phosphate, a 3'-phosphoramidate, a hexylphosphate, an aminohexyl phosphate, a 3'-phosphate, a 3'-phosphorothioate, a phosphorodithioate, a bridging methylphosphonate moiety, and a non-bridging methylphosphonate moiety 5'-aminoalkyl phosphate, a 1,3-diamino-2-propyl phosphate, 3-aminopropyl phosphate, a 6-aminohexyl phosphate, a 1,2-aminododecyl phosphate, a hydroxypropyl phosphate, a 5'-5'-inverted nucleotide moiety, a 5'-5'-inverted abasic moiety, a 5'-phosphoramidate, a 5'-phosphorothioate, a 5'-amino, a bridging and/or non-bridging 5'-phosphoramidate, a phosphorothioate, and a 5'-mercapto moiety.

Certain Nucleobase Sequences

Provided herein are methods for the treatment or prevention of fibrosis. In certain embodiments, the methods comprise administration of a pharmaceutical composition comprising a modified oligonucleotide. In certain embodiments, the methods comprise administration of a compound comprising a modified oligonucleotide. In certain embodiments, a modified oligonucleotide has a sequence that is complementary to a miRNA or a precursor thereof. In certain embodiments, the miRNA is miR-21.

Nucleobase sequences of mature miRNAs and their corresponding stem-loop sequences described herein are the sequences found in miRBase, an online searchable database of miRNA sequences and annotation, found at http://microrna.sanger.ac.uk/. Entries in the miRBase Sequence database represent a predicted hairpin portion of a miRNA transcript (the stem-loop), with information on the location and sequence of the mature miRNA sequence. The miRNA stem-loop sequences in the database are not strictly precursor miRNAs (pre-miRNAs), and may in some instances include the pre-miRNA and some flanking sequence from the presumed primary transcript. The miRNA nucleobase sequences described herein encompass any version of the miRNA, including the sequences described in Release 10.0 of the miRBase sequence database and sequences described in any earlier Release of the miRBase sequence database. A sequence database release may result in the re-naming of certain miRNAs. A sequence database release may result in a variation of a mature miRNA sequence. The compounds of the present invention encompass modified oligonucleotides that are complementary any nucleobase sequence version of the miRNAs described herein.

It is understood that any nucleobase sequence set forth herein is independent of any modification to a sugar moiety, an internucleoside linkage, or a nucleobase. It is further understood that a nucleobase sequence comprising U's also encompasses the same nucleobase sequence wherein 'U' is replaced by 'T' at one or more positions having 'U.' Conversely, it is understood that a nucleobase sequence comprising T's also encompasses the same nucleobase sequence wherein 'T; is replaced by 'U' at one or more positions having 'T.'

In certain embodiments, a modified oligonucleotide has a nucleobase sequence that is complementary to a miRNA or a precursor thereof, meaning that the nucleobase sequence of a modified oligonucleotide is a least 60%, 65%, 70%, 75%, 80%, 85%, 90%, 95%, 97%, 98% or 99% identical to the complement of a miRNA or precursor thereof over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleobases, or that the two sequences hybridize under stringent hybridization conditions. Accordingly, in certain embodiments the nucleobase sequence of a modified oligonucleotide may have one or more mismatched basepairs with respect to its target miRNA or target miRNA precursor sequence, and is capable of hybridizing to its target sequence. In certain embodiments, a modified oligonucleotide has a nucleobase sequence that is 100% complementary to a miRNA or a precursor thereof. In certain embodiments, the nucleobase sequence of a modified oligonucleotide has full-length complementary to a miRNA.

In certain embodiments, a miR-21 has the nucleobase sequence 5'-UAGCUUAUCAGACUGAUGUUGA-3' (SEQ ID NO: 1). In certain embodiments a miR-21 stem-loop sequence has the nucleobase sequence 5'-UGUCGGGUAGCUUAUCAGACUGAUG-UUGACUGUUGAAUCUCAUGGCAAC ACCAGUC-GAUGGGCUGUCUGACA-3' (SEQ ID NO: 11).

In certain embodiments, a modified oligonucleotide has a sequence that is complementary to the nucleobase sequence of miR-21 set forth as SEQ ID NO: 1.

In certain embodiments, a modified oligonucleotide has a sequence that is complementary to the nucleobase sequence of a miRNA stem-loop sequence set forth as SEQ ID NO: 11. In certain embodiments, a modified oligonucleotide has a nucleobase sequence that is complementary to the region of nucleobases 8-29 of SEQ ID NO: 11. In certain embodiments a modified oligonucleotide has a sequence that is complementary to the region of nucleobases 46 to 66 of SEQ ID NO: 11.

In certain embodiments, a modified oligonucleotide has a nucleobase sequence comprising the nucleobase sequence 5'-UCAACAUCAGUCUGAUAAGCUA-3' (SEQ ID NO: 12).

In certain embodiments, a modified oligonucleotide has a nucleobase sequence consisting of the nucleobase sequence set forth as SEQ ID NO: 12.

In certain embodiments, a modified oligonucleotide has a nucleobase sequence that is complementary to a nucleobase sequence of a pri-miR sequence comprising miR-21.

In certain embodiments, a modified oligonucleotide has a nucleobase sequence that is complementary to a nucleobase sequence having at least 80% identity to the nucleobase sequence set forth in SEQ ID NO: 1. In certain embodiments, a modified oligonucleotide has a nucleobase sequence that is complementary to a nucleobase sequence having at least 85%, at least 90%, at least 92%, at least 94%, at least 96%, or at least 98% identity to the nucleobase sequence set forth in SEQ ID NO: 1.

In certain embodiments, a modified oligonucleotide has a nucleobase sequence that is complementary to a nucleobase sequence having at least 80% identity to a nucleobase sequence of a miR-21 stem-loop sequence set forth in SEQ ID NO: 11. In certain embodiments, a modified oligonucleotide has a nucleobase sequence that is complementary to a nucleobase sequence having at least 85%, at least 90%, at least 92%, at least 94%, at least 96%, or at least 98% identity to a nucleobase sequence of a miR-21 stem-loop sequence set forth in SEQ ID NO: 11.

In certain embodiments, a nucleobase sequence of a modified oligonucleotide has full-length complementary to a miRNA nucleobase sequence listed herein, or a precursor thereof. In certain embodiments, a modified oligonucleotide has a nucleobase sequence having one mismatch with respect to the nucleobase sequence of the mature miRNA, or a precursor thereof. In certain embodiments, a modified oligonucleotide has a nucleobase sequence having two mismatches with respect to the nucleobase sequence of the miRNA, or a precursor thereof. In certain, such embodiments, a modified oligonucleotide has a nucleobase sequence having no more than two mismatches with respect to the nucleobase sequence of the mature miRNA, or a precursor thereof. In certain such embodiments, the mismatched nucleobases are contiguous. In certain such embodiments, the mismatched nucleobases are not contiguous.

In certain embodiments, a modified oligonucleotide consists of a number of linked nucleosides that is equal to the length of the mature miRNA to which it is complementary.

In certain embodiments, the number of linked nucleosides of a modified oligonucleotide is less than the length of the mature miRNA to which it is complementary. In certain such embodiments, the number of linked nucleosides of a modified oligonucleotide is one less than the length of the mature miRNA to which it is complementary. In certain such embodiments, a modified oligonucleotide has one less nucleoside at the 5' terminus. In certain such embodiments, a modified oligonucleotide has one less nucleoside at the 3' terminus. In certain such embodiments, a modified oligonucleotide has two fewer nucleosides at the 5' terminus. In certain such embodiments, a modified oligonucleotide has two fewer nucleosides at the 3' terminus. A modified oligonucleotide having a number of linked nucleosides that is less than the length of the miRNA, wherein each nucleobase of a modified oligonucleotide is complementary to each nucleobase at a corresponding position in a miRNA, is considered to be a modified oligonucleotide having a nucleobase sequence 100% complementary to a portion of a miRNA sequence.

In certain embodiments, the number of linked nucleosides of a modified oligonucleotide is greater than the length of the miRNA to which it is complementary. In certain such embodiments, the nucleobase of an additional nucleoside is complementary to a nucleobase of a miRNA stem-loop sequence. In certain embodiments, the number of linked nucleosides of a modified oligonucleotide is one greater than the length of the miRNA to which it is complementary. In certain such embodiments, the additional nucleoside is at the 5' terminus of a modified oligonucleotide. In certain such embodiments, the additional nucleoside is at the 3' terminus of a modified oligonucleotide. In certain embodiments, the number of linked nucleosides of a modified oligonucleotide is two greater than the length of the miRNA to which it is complementary. In certain such embodiments, the two additional nucleosides are at the 5' terminus of a modified oligonucleotide. In certain such embodiments, the two additional nucleosides are at the 3' terminus of a modified oligonucleotide. In certain such embodiments, one additional nucleoside is located at the 5' terminus and one additional nucleoside is located at the 3' terminus of a modified oligonucleotide.

In certain embodiments, a portion of the nucleobase sequence of a modified oligonucleotide is 100% complementary to the nucleobase sequence of the miRNA, but the modified oligonucleotide is not 100% complementary over its entire length. In certain such embodiments, the number of nucleosides of a modified oligonucleotide having a 100% complementary portion is greater than the length of the miRNA. For example, a modified oligonucleotide consisting of 24 linked nucleosides, where the nucleobases of nucleosides 1 through 23 are each complementary to a corresponding position of a miRNA that is 23 nucleobases in length, has a 23 nucleoside portion that is 100% complementary to the nucleobase sequence of the miRNA and approximately 96% overall complementarity to the nucleobase sequence of the miRNA.

In certain embodiments, the nucleobase sequence of a modified oligonucleotide is 100% complementary to a portion of the nucleobase sequence of a miRNA. For example, a modified oligonucleotide consisting of 22 linked nucleosides, where the nucleobases of nucleosides 1 through 22 are each complementary to a corresponding position of a miRNA that is 23 nucleobases in length, is 100% complementary to a 22 nucleobase portion of the nucleobase sequence of a miRNA. Such a modified oligonucleotide has approximately 96% overall complementarity to the nucleobase sequence of the entire miRNA, and has 100% complementarity to a 22 nucleobase portion of the miRNA.

In certain embodiments, a portion of the nucleobase sequence of a modified oligonucleotide is 100% complementary to a portion of the nucleobase sequence of a miRNA, or a precursor thereof. In certain such embodiments, 15 contiguous nucleobases of a modified oligonucleotide are each complementary to 15 contiguous nucleobases of a miRNA, or a precursor thereof. In certain such embodiments, 16 contiguous nucleobases of a modified oligonucleotide are each complementary to 16 contiguous nucleobases of a miRNA, or a precursor thereof. In certain such embodiments, 17 contiguous nucleobases of a modified oligonucleotide are each complementary to 17 contiguous nucleobases of a miRNA, or a precursor thereof. In certain such embodiments, 18 contiguous nucleobases of a modified oligonucleotide are each complementary to 18 contiguous nucleobases of a miRNA, or a precursor thereof. In certain such embodiments, 19 contiguous nucleobases of a modified oligonucleotide are each complementary to 19 contiguous nucleobases of a miRNA, or a precursor thereof. In certain such embodiments, 20 contiguous nucleobases of a modified oligonucleotide are each complementary to 20 contiguous nucleobases of a miRNA, or a precursor thereof. In certain such embodiments, 22 contiguous nucleobases of a modified oligonucleotide are each complementary to 22 contiguous nucleobases of a miRNA, or a precursor thereof. In certain such embodiments, 23 contiguous nucleobases of a modified oligonucleotide are each complementary to 23 contiguous nucleobases of a miRNA, or a precursor thereof. In certain such embodiments, 24 contiguous nucleobases of a modified oligonucleotide are each complementary to 24 contiguous nucleobases of a miRNA, or a precursor thereof.

Certain Modified Oligonucleotides

In certain embodiments, a modified oligonucleotide consists of 12 to 30 linked nucleosides. In certain embodiments, a modified oligonucleotide consists of 15 to 25 linked nucleosides. In certain embodiments, a modified oligonucleotide consists of 19 to 24 linked nucleosides. In certain embodiments, a modified oligonucleotide consists of 21 to 24 linked nucleosides.

In certain embodiments, a modified oligonucleotide consists of 12 linked nucleosides. In certain embodiments, a modified oligonucleotide consists of 13 linked nucleosides. In certain embodiments, a modified oligonucleotide consists of 14 linked nucleosides. In certain embodiments, a modified oligonucleotide consists of 15 linked nucleosides. In certain embodiments, a modified oligonucleotide consists of 16 linked nucleosides. In certain embodiments, a modified oligonucleotide consists of 17 linked nucleosides. In certain embodiments, a modified oligonucleotide consists of 18 linked nucleosides. In certain embodiments, a modified oligonucleotide consists of 19 linked nucleosides. In certain embodiments, a modified oligonucleotide consists of 20 linked nucleosides. In certain embodiments, a modified oligonucleotide consists of 21 linked nucleosides. In certain embodiments, a modified oligonucleotide consists of 22 linked nucleosides. In certain embodiments, a modified oligonucleotide consists of 23 linked nucleosides. In certain embodiments, a modified oligonucleotide consists of 24 linked nucleosides. In certain embodiments, a modified oligonucleotide consists of 25 linked nucleosides. In certain embodiments, a modified oligonucleotide consists of 26 linked nucleosides. In certain embodiments, a modified oligonucleotide consists of 27 linked nucleosides. In certain embodiments, a modified oligonucleotide consists of 28 linked nucleosides. In certain embodiments, a modified oligonucleotide consists of 29 linked nucleosides. In certain embodiments, a modified oligonucleotide consists of 30 linked nucleosides. In certain such embodiments, a modified oligonucleotide comprises linked nucleosides selected from contiguous nucleobases of SEQ ID NO: 12.

Certain Modifications

Modified oligonucleotides of the present invention comprise one or more modifications to a nucleobase, sugar, and/or internucleoside linkage. A modified nucleobase, sugar, and/or internucleoside linkage may be selected over an unmodified form because of desirable properties such as, for example, enhanced cellular uptake, enhanced affinity for other oligonucleotides or nucleic acid targets and increased stability in the presence of nucleases.

In certain embodiments, a modified oligonucleotide of the present invention comprises one or more modified nucleosides. In certain such embodiments, a modified nucleoside is a stabilizing nucleoside. An example of a stabilizing nucleoside is a sugar-modified nucleoside.

In certain embodiments, a modified nucleoside is a sugar-modified nucleoside. In certain such embodiments, the sugar-modified nucleosides can further comprise a natural or modified heterocyclic base moiety and/or a natural or modified internucleoside linkage and may include further modifications independent from the sugar modification. In certain embodiments, a sugar modified nucleoside is a 2'-modified nucleoside, wherein the sugar ring is modified at the 2' carbon from natural ribose or 2'-deoxy-ribose.

In certain embodiments, a 2'-modified nucleoside has a bicyclic sugar moiety. In certain such embodiments, the bicyclic sugar moiety is a D sugar in the alpha configuration. In certain such embodiments, the bicyclic sugar moiety is a D sugar in the beta configuration. In certain such embodiments, the bicyclic sugar moiety is an L sugar in the alpha configuration. In certain such embodiments, the bicyclic sugar moiety is an L sugar in the beta configuration.

In certain embodiments, the bicyclic sugar moiety comprises a bridge group between the 2' and the 4'-carbon atoms. In certain such embodiments, the bridge group comprises from 1 to 8 linked biradical groups. In certain embodiments, the bicyclic sugar moiety comprises from 1 to 4 linked biradical groups. In certain embodiments, the bicyclic sugar moiety comprises 2 or 3 linked biradical groups. In certain embodiments, the bicyclic sugar moiety comprises 2 linked biradical groups. In certain embodiments, a linked biradical group is selected from —O—, —S—, —N($R_1$)—, —C($R_1$)($R_2$)—, —C($R_1$)=C($R_1$)—, —C($R_1$)=N—, —C(=$NR_1$)—, —Si($R_1$)($R_2$)—, —S(=O)$_2$—, —S(=O)—, —C(=O)— and —C(=S)—; where each $R_1$ and $R_2$ is, independently, H, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, a heterocycle radical, a substituted hetero-cycle radical, heteroaryl, substituted heteroaryl, $C_5$-$C_7$ alicyclic radical, substituted $C_5$-$C_7$ alicyclic radical, halogen, substituted oxy (—O—), amino, substituted amino, azido, carboxyl, substituted carboxyl, acyl, substituted acyl, CN, thiol, substituted thiol, sulfonyl (S(=O)$_2$—H), substituted sulfonyl, sulfoxyl (S(=O)—H) or substituted sulfoxyl; and each substituent group is, independently, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, amino, substituted amino, acyl, substituted acyl, $C_1$-$C_{12}$ aminoalkyl, $C_1$-$C_{12}$ aminoalkoxy, substituted $C_1$-$C_{12}$ aminoalkyl, substituted $C_1$-$C_{12}$ aminoalkoxy or a protecting group.

In some embodiments, the bicyclic sugar moiety is bridged between the 2' and 4' carbon atoms with a biradical group selected from —O—($CH_2$)$_p$—, —O—$CH_2$—, —O—$CH_2CH_2$—, —O—CH(alkyl)-, —NH—($CH_2$)$_p$—, —N(alkyl)-($CH_2$)$_p$—, —O—CH(alkyl)-, —(CH(alkyl))—($CH_2$)$_p$—, —NH—O—($CH_2$)$_p$—, —N(alkyl)-O—($CH_2$)$_p$—, or —O—N(alkyl)-($CH_2$)$_p$—, wherein p is 1, 2, 3, 4 or 5 and each alkyl group can be further substituted. In certain embodiments, p is 1, 2 or 3.

In certain embodiments, a 2'-modified nucleoside comprises a 2'-substituent group selected from halo, allyl, amino, azido, SH, CN, OCN, $CF_3$, $OCF_3$, O—, S—, or N($R_m$)-alkyl; O—, S—, or N($R_m$)-alkenyl; O—, S— or N($R_m$)-alkynyl; O-alkylenyl-O-alkyl, alkynyl, alkaryl, aralkyl, O-alkaryl, O-aralkyl, O($CH_2$)$_2$$SCH_3$, O—($CH_2$)$_2$—O—N($R_m$)($R_n$) or O—$CH_2$—C(=O)—N($R_m$)($R_n$), where each $R_m$ and $R_n$ is, independently, H, an amino protecting group or substituted or unsubstituted $C_1$-$C_{10}$ alkyl. These 2'-substituent groups can be further substituted with one or more substituent groups independently selected from hydroxyl, amino, alkoxy, carboxy, benzyl, phenyl, nitro ($NO_2$), thiol, thioalkoxy (S-alkyl), halogen, alkyl, aryl, alkenyl and alkynyl.

In certain embodiments, a 2'-modified nucleoside comprises a 2'-substituent group selected from F, $NH_2$, $N_3$, $OCF_3$, O—$CH_3$, O($CH_2$)$_3$$NH_2$, $CH_2$—CH=$CH_2$, O—$CH_2$—CH=$CH_2$, $OCH_2CH_2OCH_3$, O($CH_2$)$_2$$SCH_3$, O—($CH_2$)$_2$—O—N($R_m$)($R_n$), —O($CH_2$)$_2$—O—($CH_2$)$_2$N($CH_3$)$_2$, and N-substituted acetamide (O—$CH_2$—C(=O)—N($R_m$)($R_n$) where each $R_m$ and $R_n$ is, independently, H, an amino protecting group or substituted or unsubstituted $C_1$-$C_{10}$ alkyl.

In certain embodiments, a 2'-modified nucleoside comprises a 2'-substituent group selected from F, $OCF_3$, O—$CH_3$, $OCH_2CH_2OCH_3$, 2'—O($CH_2$)$_2$$SCH_3$, O—($CH_2$)$_2$—O—N($CH_3$)$_2$, —O($CH_2$)$_2$—O—($CH_2$)$_2$N($CH_3$)$_2$, and O—$CH_2$—C(=O)—N(H)$CH_3$.

In certain embodiments, a 2'-modified nucleoside comprises a 2'-substituent group selected from F, O—$CH_3$, and $OCH_2CH_2OCH_3$.

In certain embodiments, a sugar-modified nucleoside is a 4'-thio modified nucleoside. In certain embodiments, a sugar-modified nucleoside is a 4'-thio-2'-modified nucleoside. A 4'-thio modified nucleoside has a β-D-ribonucleoside where the 4'-O replaced with 4'-S. A 4'-thio-2'-modified nucleoside is a 4'-thio modified nucleoside having the 2'-OH replaced with a 2'-substituent group. Suitable 2'-substituent groups include 2'-$OCH_3$, 2'-O—($CH_2$)$_2$—$OCH_3$, and 2'-F.

In certain embodiments, a modified oligonucleotide of the present invention comprises one or more internucleoside modifications. In certain such embodiments, each internucleoside linkage of a modified oligonucleotide is a modified internucleoside linkage. In certain embodiments, a modified internucleoside linkage comprises a phosphorus atom.

In certain embodiments, a modified oligonucleotide of the present invention comprises at least one phosphorothioate internucleoside linkage. In certain embodiments, each internucleoside linkage of a modified oligonucleotide is a phosphorothioate internucleoside linkage.

In certain embodiments, a modified internucleoside linkage does not comprise a phosphorus atom. In certain such embodiments, an internucleoside linkage is formed by a short chain alkyl internucleoside linkage. In certain such embodiments, an internucleoside linkage is formed by a cycloalkyl internucleoside linkages. In certain such embodiments, an internucleoside linkage is formed by a mixed heteroatom and alkyl internucleoside linkage. In certain such, embodiments, an internucleoside linkage is formed by a mixed heteroatom and cycloalkyl internucleoside linkages. In certain such embodiments, an internucleoside linkage is formed by one or more short chain heteroatomic internucleoside linkages. In certain such embodiments, an internucleoside linkage is formed by one or more heterocyclic internucleoside linkages. In certain such embodiments, an internucleoside linkage has an amide backbone. In certain such embodiments, an internucleoside linkage has mixed N, O, S and $CH_2$ component parts.

In certain embodiments, a modified oligonucleotide comprises one or more modified nucleobases. In certain embodiments, a modified oligonucleotide comprises one or more 5-methylcytosines. In certain embodiments, each cytosine of a modified oligonucleotide comprises a 5-methylcytosine.

In certain embodiments, a modified nucleobase is selected from 5-hydroxymethyl cytosine, 7-deazaguanine and 7-deazaadenine. In certain embodiments, a modified nucleobase is selected from 7-deaza-adenine, 7-deazaguanosine, 2-aminopyridine and 2-pyridone. In certain embodiments, a modified nucleobase is selected from 5-substituted pyrimidines, 6-azapyrimidines and N-2, N-6 and O-6 substituted purines, including 2 aminopropyladenine, 5-propynyluracil and 5-propynylcytosine.

In certain embodiments, a modified nucleobase comprises a polycyclic heterocycle. In certain embodiments, a modified nucleobase comprises a tricyclic heterocycle. In certain embodiments, a modified nucleobase comprises a phenoxazine derivative. In certain embodiments, the phenoxazine can be further modified to form a nucleobase known in the art as a G-clamp.

Certain Oligonucleotide Motifs

Suitable motifs for modified oligonucleotides of the present invention include, but are not limited to, fully modified, uniformly modified, positionally modified, and gapmer. Modified oligonucleotides having a fully modified motif, including a uniformly modified motif, may be designed to target mature miRNAs. Alternatively, modified oligonucleotides having a fully modified motif, including a uniformly modified motif, may be designed to target certain sites of pri-miRNAs or pre-miRNAs, to block the processing of miRNA precursors into mature miRNAs. Modified oligonucleotides having a fully modified motif or uniformly modified motif are effective inhibitors of miRNA activity.

In certain embodiments, a fully modified oligonucleotide comprises a sugar modification at each nucleoside. In certain such embodiments, pluralities of nucleosides are 2'-O-methoxyethyl nucleosides and the remaining nucleosides are 2'-fluoro nucleosides. In certain such embodiments, each of a plurality of nucleosides is a 2'-O-methoxyethyl nucleoside and each of a plurality of nucleosides is a bicyclic nucleoside. In certain such embodiments, a fully modified oligonucleotide further comprises at least one modified internucleoside linkage. In certain such embodiments, each internucleoside linkage of a fully sugar-modified oligonucleotide is a modified internucleoside linkage. In certain embodiments, a fully sugar-modified oligonucleotide further comprises at least one phosphorothioate internucleoside linkage. In certain such embodiments, each internucleoside linkage of a fully sugar-modified oligonucleotide is a phosphorothioate internucleoside linkage.

In certain embodiments, a fully modified oligonucleotide is modified at each internucleoside linkage. In certain such embodiments, each internucleoside linkage of a fully modified oligonucleotide is a phosphorothioate internucleoside linkage.

In certain embodiments, a uniformly modified oligonucleotide comprises the same sugar modification at each nucleoside. In certain such embodiments, each nucleoside of a modified oligonucleotide comprises a 2'-O-methoxyethyl sugar modification. In certain embodiments, each nucleoside of a modified oligonucleotide comprises a 2'-O-methyl sugar modification. In certain embodiments, each nucleoside of a modified oligonucleotide comprises a 2'-fluoro sugar modification. In certain such embodiments, a uniformly modified oligonucleotide further comprises at least one modified internucleoside linkage. In certain such embodiments, each internucleoside linkage of a uniformly sugar-modified oligonucleotide is a modified internucleoside linkage. In certain embodiments, a uniformly sugar-modified oligonucleotide further comprises at least one phosphorothioate internucleoside linkage. In certain such embodiments, each internucleoside linkage of a uniformly sugar-modified oligonucleotide is a phosphorothioate internucleoside linkage.

In certain embodiments, a uniformly modified oligonucleotide comprises the same internucleoside linkage modifications throughout. In certain such embodiments, each internucleoside linkage of a uniformly modified oligonucleotide is a phosphorothioate internucleoside linkage.

In certain embodiments, a modified oligonucleotide comprises the same sugar modification at each nucleoside, and further comprises one or more internucleoside linkage modifications. In certain such embodiments, the modified oligonucleotide comprises one modified internucleoside linkage at the 5' terminus and one modified internucleoside linkage at the 3' terminus. In certain embodiments, the modified oligonucleotide comprises two modified internucleoside linkages at the 5' terminus and two modified internucleoside linkages at the 3' terminus. In certain embodiments, the modified oligonucleotide comprises two modified internucleoside linkages at the 5' terminus and three modified internucleoside linkages at the 3' terminus. In certain embodiments, the modified oligonucleotide comprises two modified internucleoside linkages at the 5' terminus and four modified internucleoside linkages at the 3' terminus. In certain such embodiments, the modified internucleoside linkage is a phosphorothioate internucleoside linkage.

In certain embodiments, a modified oligonucleotide is represented by the following formula III:

(5')QxQz$^1$(Qy)$_n$Qz$^2$Qz$^3$Qz$^4$Q-L(3')

In certain such embodiments, an compound is represented by formula III. In certain embodiments, Q is a 2'-O-methyl modified nucleoside. In certain embodiments, x is phosphorothioate. In certain embodiments, y is phosphodiester. In certain embodiments, each of z1, z2, z3, and z4 is, independently phosphorothioate or phosphodiester. In certain embodiments, n is 6 to 17. In certain embodiments, L is cholesterol. In certain embodiments, n is 12 to 17.

In certain embodiments, x is

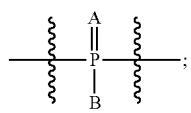

One of A and B is S while the other is O;

y is

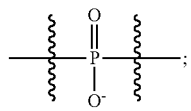

Each of z1, z2, z3, and z4 is independently x or y;
n=6-17
L is

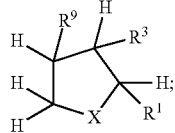

Wherein:
X is N(CO)R$^7$, or NR$^7$;
Each of R$^1$, R$^3$ and R$^9$, is independently, H, OH, or —CH$_2$OR$^b$ provided that at least one of R$^1$, R$^3$ and R$^9$ is OH and at least one of R$^1$, R$^3$ and R$^9$ is —CH$_2$OR$^b$;
R$^7$ is R$^d$ or C$_1$-C$_{20}$ alkyl substituted with NR$^c$R$^d$ or NHC(O)R$^d$;
R$^c$ is H or C$_1$-C$_6$ alkyl;
R$^d$ is a carbohydrate radical; or a steroid radical, which is optionally tethered to at least one carbohydrate radical; and
R$^b$ is

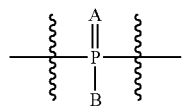

with one of A and B is S while the other is O.

In certain embodiments, R$^d$ is cholesterol. In certain embodiments each of z$^1$, z$^2$, z$^3$, and z$^4$ is

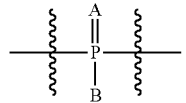

with one of A and B is S while the other is O.

In certain embodiments, R$^1$ is —CH$_2$OR$^b$. In certain embodiments, R$^9$ is OH. In certain embodiments, R$^1$ and R$^9$ are trans. In certain embodiments, R$^9$ is OH. In certain embodiments, R$^1$ and R$^3$ are trans. In certain embodiments, R$^3$ is —CH$_2$OR$^b$. In certain embodiments, R$^1$ is OH. In certain embodiments, R$^1$ and R$^3$ are trans. In certain embodiments, R$^9$ is OH. In certain embodiments, R$^3$ and R$^9$ are trans. In certain embodiments, R$^9$ is CH$_2$OR$^b$. In certain embodiments, R$^1$ is OH. In certain embodiments, R$^1$ and R$^9$ are trans. In certain embodiments, X is NC(O)R$^7$. In certain embodiments, R$^7$ is —CH$_2$(CH$_2$)$_3$CH$_2$NHC(O)R$^d$.

In certain embodiments, a positionally modified oligonucleotide comprises regions of linked nucleosides, where each nucleoside of each region comprises the same sugar moiety, and where each nucleoside of each region comprises a sugar moiety different from that of an adjacent region.

In certain embodiments, a positionally modified oligonucleotide comprises at least 10 2'-fluoro modified nucleosides. Such a positionally modified oligonucleotide may be represented by the following formula I:

5'-T$_1$-(Nu$_1$-L$_1$)$_{n1}$-(Nu$_2$-L$_2$)$_{n2}$-Nu$_2$-(L$_3$-Nu$_3$)$_{n3}$-T$_2$-3', wherein:
each Nu$_1$ and Nu$_3$ is, independently, a stabilizing nucleoside;
at least 10 Nu$_2$ are 2'-fluoro nucleosides;
each L$_1$, L$_2$ and L$_3$ is, independently, an internucleoside linkage;
each T$_1$ and T$_2$ is, independently, H, a hydroxyl protecting group, an optionally linked conjugate group or a capping group;
n$_1$ is from 0 to about 3;
n$_2$ is from about 14 to about 22;
n$_3$ is from 0 to about 3; and
provided that if n$_1$ is 0 then T$_1$ is not H or a hydroxyl protecting group, and if n$_3$ is 0, then T$_2$ is not H or a hydroxyl protecting group.

In certain such embodiments, n1 and n3 are each, independently, from 1 to about 3. In certain embodiments, n$_1$ and n$_3$ are each, independently, from 2 to about 3. In certain embodiments, n$_1$ is 1 or 2 and n$_3$ is 2 or 3. In certain embodiments, n$_1$ and n$_3$ are each 2. In certain embodiments, at least one of n1 and n3 is greater than zero. In certain embodiments, n1 and n3 is each greater than zero. In certain embodiments, one of n1 and n3 is greater than zero. In certain embodiments, one of n1 and n3 is greater than one.

In certain embodiments, n$_2$ is from 16 to 20. In certain embodiments, n$_2$ is from 17 to 19. In certain embodiments, n$_2$ is 18. In certain embodiments, n$_2$ is 19. In certain embodiments, n$_2$ is 20.

In certain embodiments, about 2 to about 8 of the Nu$_2$ nucleosides are stabilizing nucleosides. In certain embodiments, from about 2 to about 6 of the Nu$_2$ nucleosides are stabilizing nucleosides. In certain embodiments, from about 3 to about 4 of the Nu$_2$ nucleosides are stabilizing nucleosides. In certain embodiments, 3 of the Nu$_2$ nucleosides are stabilizing nucleosides.

In certain embodiments, each of the Nu$_2$ stabilizing nucleosides is separated from the Nu$_3$ stabilizing nucleosides by from 2 to about 8 2'-fluoro nucleosides. In certain embodiments each of the Nu$_2$ stabilizing nucleosides is separated from the Nu$_3$ stabilizing nucleosides by from 3 to about 8 2'-fluoro nucleosides. In certain embodiments each of the Nu$_2$ stabilizing nucleosides is separated from the Nu$_3$ stabilizing nucleosides by from 5 to about 8 2'-fluoro nucleosides.

In certain embodiments, a modified oligonucleotide comprises from 2 to about 6 Nu$_2$ stabilizing nucleosides. In certain embodiments, a modified oligonucleotide comprises 3 Nu$_2$ stabilizing nucleosides.

In certain embodiments, each of the Nu$_2$ stabilizing nucleosides is linked together in one contiguous sequence. In certain embodiments, at least two of the Nu$_2$ stabilizing nucleosides are separated by at least one of the 2'-fluoro nucleosides. In certain embodiments, each of the Nu$_2$ stabilizing nucleosides is separated by at least one of the 2'-fluoro nucleosides.

In certain embodiments, at least two contiguous sequences of the Nu$_2$ 2'-fluoro nucleosides are separated by at least one of the stabilizing nucleosides wherein each of the contiguous sequences have the same number of 2'-fluoro nucleosides.

In certain embodiments, T$_1$ and T$_2$ are each, independently, H or a hydroxyl protecting group. In certain embodiments, at least one of T$_1$ and T$_2$ is 4,4'-dimethoxytrityl. In certain embodiments, at least one of T$_1$ and T$_2$ is an optionally linked conjugate group. In certain embodiments, at least one of T$_1$ and T$_2$ is a capping group. In certain embodiments, the capping group is an inverted deoxy abasic group.

In certain embodiments, a positionally modified oligonucleotide comprises at least one modified internucleoside linkage. In certain such embodiments, each internucleoside linkage of a positionally modified oligonucleoside is a modified internucleoside linkage. In certain embodiments, at least one internucleoside linkage of a positionally modified oligonucleotide is a phosphorothioate internucleoside linkage. In certain such embodiments, each internucleoside linkage of a positionally modified oligonucleotide is a phosphorothioate internucleoside linkage.

In certain embodiments, a positionally modified motif is represented by the following formula II, which represents a modified oligonucleotide consisting of linked nucleosides:

$$T_1\text{-}(Nu_1)_{n1}\text{-}(Nu_2)_{n2}\text{-}(Nu_3)_{n3}\text{-}(Nu_4)_{n4}\text{-}(Nu_5)_{n5}\text{-}T_2,$$

wherein:
$Nu_1$ and $Nu_5$ are, independently, 2' stabilizing nucleosides;
$Nu_2$ and $Nu_4$ are 2'-fluoro nucleosides;
$Nu_3$ is a 2'-modified nucleoside;
each of n1 and n5 is, independently, from 0 to 3;
the sum of n2 plus n4 is between 10 and 25;
n3 is from 0 and 5; and
each $T_1$ and $T_2$ is, independently, H, a hydroxyl protecting group, an optionally linked conjugate group or a capping group.

In certain embodiments, the sum of n2 and n4 is 16. In certain embodiments, the sum of n2 and n4 is 17. In certain embodiments, the sum of n2 and n4 is 18. In certain embodiments, n1 is 2; n3 is 2 or 3; and n5 is 2.

In certain embodiments, $Nu_1$ and $Nu_5$ are, independently, 2'-modified nucleosides.

In certain embodiments, $Nu_1$ is $O-(CH_2)_2-OCH_3$, $Nu_3$ is $O-(CH_2)_2-OCH_3$, $Nu_5O-(CH_2)_2-OCH_3$, $T_1$ is H and $T_2$ is H.

In certain embodiments, a modified oligonucleotide complementary to a miRNA and consisting of 22 linked nucleosides has a Formula II selected from Table A, where each internucleoside linkage is a phosphorothioate internucleoside linkage. In certain embodiments, a modified oligonucleotide having a Formula II selected from Table A has the nucleobase sequence of SEQ ID NO: 12.

TABLE A

| n1 | n2 | n3 | n4 | n5 | $Nu_1$ | $Nu_3$ | $Nu_5$ | $T_1$ | $T_2$ |
|---|---|---|---|---|---|---|---|---|---|
| 2 | 18 | 0 | 0 | 2 | 2'-MOE | 2'-MOE | 2'-MOE | H | H |
| 2 | 2 | 2 | 14 | 2 | 2'-MOE | 2'-MOE | 2'-MOE | H | H |
| 2 | 3 | 2 | 13 | 2 | 2'-MOE | 2'-MOE | 2'-MOE | H | H |
| 2 | 4 | 2 | 12 | 2 | 2'-MOE | 2'-MOE | 2'-MOE | H | H |
| 2 | 5 | 2 | 11 | 2 | 2'-MOE | 2'-MOE | 2'-MOE | H | H |
| 2 | 6 | 2 | 10 | 2 | 2'-MOE | 2'-MOE | 2'-MOE | H | H |
| 2 | 7 | 2 | 9 | 2 | 2'-MOE | 2'-MOE | 2'-MOE | H | H |
| 2 | 8 | 2 | 8 | 2 | 2'-MOE | 2'-MOE | 2'-MOE | H | H |
| 2 | 9 | 2 | 7 | 2 | 2'-MOE | 2'-MOE | 2'-MOE | H | H |
| 2 | 10 | 2 | 6 | 2 | 2'-MOE | 2'-MOE | 2'-MOE | H | H |
| 2 | 11 | 2 | 5 | 2 | 2'-MOE | 2'-MOE | 2'-MOE | H | H |
| 2 | 12 | 2 | 4 | 2 | 2'-MOE | 2'-MOE | 2'-MOE | H | H |
| 2 | 13 | 2 | 3 | 2 | 2'-MOE | 2'-MOE | 2'-MOE | H | H |
| 2 | 14 | 2 | 2 | 2 | 2'-MOE | 2'-MOE | 2'-MOE | H | H |
| 2 | 2 | 3 | 13 | 2 | 2'-MOE | 2'-MOE | 2'-MOE | H | H |
| 2 | 3 | 3 | 12 | 2 | 2'-MOE | 2'-MOE | 2'-MOE | H | H |
| 2 | 4 | 3 | 11 | 2 | 2'-MOE | 2'-MOE | 2'-MOE | H | H |
| 2 | 5 | 3 | 10 | 2 | 2'-MOE | 2'-MOE | 2'-MOE | H | H |
| 2 | 6 | 3 | 9 | 2 | 2'-MOE | 2'-MOE | 2'-MOE | H | H |
| 2 | 7 | 3 | 8 | 2 | 2'-MOE | 2'-MOE | 2'-MOE | H | H |
| 2 | 8 | 3 | 7 | 2 | 2'-MOE | 2'-MOE | 2'-MOE | H | H |
| 2 | 9 | 3 | 6 | 2 | 2'-MOE | 2'-MOE | 2'-MOE | H | H |
| 2 | 10 | 3 | 5 | 2 | 2'-MOE | 2'-MOE | 2'-MOE | H | H |
| 2 | 11 | 3 | 4 | 2 | 2'-MOE | 2'-MOE | 2'-MOE | H | H |
| 2 | 12 | 3 | 3 | 2 | 2'-MOE | 2'-MOE | 2'-MOE | H | H |
| 2 | 13 | 3 | 2 | 2 | 2'-MOE | 2'-MOE | 2'-MOE | H | H |
| 2 | 8 | 6 | 4 | 2 | 2'-MOE | 2'-MOE | 2'-MOE | H | H |

A modified oligonucleotide having a gapmer motif may have an internal region consisting of linked 2'-deoxynucleotides, and external regions consisting of linked 2'-modified nucleosides. Such a gapmer may be designed to elicit RNase H cleavage of a miRNA precursor. The internal 2'-deoxynucleoside region serves as a substrate for RNase H, allowing the cleavage of the miRNA precursor to which a modified oligonucleotide is targeted. In certain embodiments, each nucleoside of each external region comprises the same 2'-modified nucleoside. In certain embodiments, one external region is uniformly comprised of a first 2'-modified nucleoside and the other external region is uniformly comprised of a second 2'-modified nucleoside.

A modified oligonucleotide having a gapmer motif may have a sugar modification at each nucleoside. In certain embodiments, the internal region is uniformly comprised of a first 2'-modified nucleoside and each of the wings is uniformly comprised of a second 2'-modified nucleoside. In certain such embodiments, the internal region is uniformly comprised of 2'-fluoro nucleosides and each external region is uniformly comprised of 2'-O-methoxyethyl nucleosides.

In certain embodiments, each external region of a gapmer consists of linked 2'-O-methoxyethyl nucleosides. In certain embodiments, each external region of a gapmer consists of linked 2'-O-methyl nucleosides. In certain embodiments, each external region of a gapmer consists of 2'-fluoro nucleosides. In certain embodiments, each external region of a gapmer consists of linked bicyclic nucleosides.

In certain embodiments, each nucleoside of one external region of a gapmer comprises 2'-O-methoxyethyl nucleosides and each nucleoside of the other external region comprises a different 2'-modification. In certain such embodiments, each nucleoside of one external region of a gapmer comprises 2'-O-methoxyethyl nucleosides and each nucleoside of the other external region comprises 2'-O-methyl nucleosides. In certain such embodiments, each nucleoside of one external region of a gapmer comprises 2'-O-methoxyethyl nucleosides and each nucleoside of the other external region comprises 2'-fluoro nucleosides. In certain such embodiments, each nucleoside of one external region of a gapmer comprises 2'-O-methyl nucleosides and each nucleoside of the other external region comprises 2'-fluoro nucleosides. In certain such embodiments, each nucleoside of one external region of a gapmer comprises 2'-O-methoxyethyl nucleosides and each nucleoside of the other external region comprises bicyclic nucleosides. In certain such embodiments, each nucleoside of one external region of a gapmer comprises 2'-O-methyl nucleosides and each nucleoside of the other external region comprises bicyclic nucleosides.

In certain embodiments, nucleosides of one external region comprise two or more sugar modifications. In certain embodiments, nucleosides of each external region comprise two or more sugar modifications. In certain embodiments, at least one nucleoside of an external region comprises a 2'-O-methoxyethyl sugar and at least one nucleoside of the same external region comprises a 2'-fluoro sugar. In certain embodiments, at least one nucleoside of an external region comprises a 2'-O-methoxyethyl sugar and at least one nucleoside of the same external region comprises a bicyclic sugar moiety. In certain embodiments, at least one nucleoside of an external region comprises a 2'-O-methyl sugar and at least one nucleoside of the same external region comprises a bicyclic sugar moiety. In certain embodiments at least one nucleoside of an external region comprises a 2'-O-methyl sugar and at least one nucleoside of the same external region comprises a 2'-fluoro sugar. In certain embodiments, at least one nucleoside of an external region comprises a 2'-fluoro sugar and at least one nucleoside of the same external region comprises a bicyclic sugar moiety.

In certain embodiments, each external region of a gapmer consists of the same number of linked nucleosides. In certain embodiments, one external region of a gapmer consists a number of linked nucleosides different that that of the other external region.

In certain embodiments, the external regions comprise, independently, from 1 to 6 nucleosides. In certain embodiments, an external region comprises 1 nucleoside. In certain embodiments, an external region comprises 2 nucleosides. In certain embodiments, an external region comprises 3 nucleosides. In certain embodiments, an external region comprises 4 nucleosides. In certain embodiments, an external region comprises 5 nucleosides. In certain embodiments, an external region comprises 6 nucleosides. In certain embodiments, the internal region consists of 17 to 28 linked nucleosides. In certain embodiments, an internal region consists of 17 to 21 linked nucleosides. In certain embodiments, an internal region consists of 17 linked nucleosides. In certain embodiments, an internal region consists of 18 linked nucleosides. In certain embodiments, an internal region consists of 19 linked nucleosides. In certain embodiments, an internal region consists of 20 linked nucleosides. In certain embodiments, an internal region consists of 21 linked nucleosides. In certain embodiments, an internal region consists of 22 linked nucleosides. In certain embodiments, an internal region consists of 23 linked nucleosides. In certain embodiments, an internal region consists of 24 linked nucleosides. In certain embodiments, an internal region consists of 25 linked nucleosides. In certain embodiments, an internal region consists of 26 linked nucleosides. In certain embodiments, an internal region consists of 27 linked nucleosides. In certain embodiments, an internal region consists of 28 linked nucleosides.

Certain Quantitation Assays

The effects of antisense inhibition of a miRNA following the administration of modified oligonucleotides may be assessed by a variety of methods known in the art. In certain embodiments, these methods are be used to quantitate miRNA levels in cells or tissues in vitro or in vivo. In certain embodiments, changes in miRNA levels are measured by microarray analysis. In certain embodiments, changes in miRNA levels are measured by one of several commercially available PCR assays, such as the TaqMan® MicroRNA Assay (Applied Biosystems). In certain embodiments, antisense inhibition of a miRNA is assessed by measuring the mRNA and/or protein level of a target of a miRNA. Antisense inhibition of a miRNA generally results in the increase in the level of mRNA and/or protein of a target of the miRNA.

Certain Experimental Models

In certain embodiments, the present invention provides methods of using and/or testing modified oligonucleotides of the present invention in an experimental model. In certain embodiments, experimental models are employed to evaluate the effectiveness of modified oligonucleotides of the invention for the treatment of fibrosis. Those having skill in the art are able to select and modify the protocols for such experimental models to evaluate a pharmaceutical agent of the invention.

Modified oligonucleotides may first be tested in cultured cells. Suitable cell types include those that are related to the cell type to which delivery of a modified oligonucleotide is desired in vivo. For example, suitable cell types for the study of modified oligonucleotides for the treatment of fibrosis include fibroblasts, cardiomyocytes, and stellate cells.

In certain embodiments, the extent to which a modified oligonucleotide inhibits the activity of a miRNA is assessed in cultured cells. In certain embodiments, inhibition of miRNA activity may be assessed by measuring the levels of the miRNA. Alternatively, the level of a predicted or validated miRNA target may be measured. An inhibition of miRNA activity may result in the increase in the mRNA and/or protein of a miRNA target. Further, in certain embodiments, certain phenotypic outcomes may be measured. For example, suitable phenotypic outcomes include inhibition of cell proliferation, the induction of cell death, and/or the induction of apoptosis.

Following the in vitro identification of a modified oligonucleotide that effectively inhibits the activity of a miRNA, modified oligonucleotides are further tested in in vivo experimental models.

Suitable experimental models for the testing of pharmaceutical agents for the treatment of fibrosis, including pharmaceutical agents comprising modified oligonucleotides complementary to a miR-122, include a pressure overload-induced hypertrophy model, described herein.

An additional experimental model for the testing of pharmaceutical agents for the treatment of fibrosis includes, but is not limited to, the methionine choline deficient (MCD) diet model (see, for example, Yamaguchi et al., Hepatology, 2008, 47, 625-635). db/db mice spontaneously develop obesity, diabetes, and fatty livers. Feeding such mice a MCD diet induces non-alcoholic steatohepatitis (NASH) and liver fibrosis within 4 to 8 weeks. Modified oligonucleotides having nucleobase complementary to a miRNA are tested in this model for their effects on liver fibrosis.

The following examples are presented in order to more fully illustrate some embodiments of the invention. They should, in no way be construed, however, as limiting the broad scope of the invention.

EXAMPLES

Example 1

A Role for miR-21 in Cardiac Disease

Figure 4:
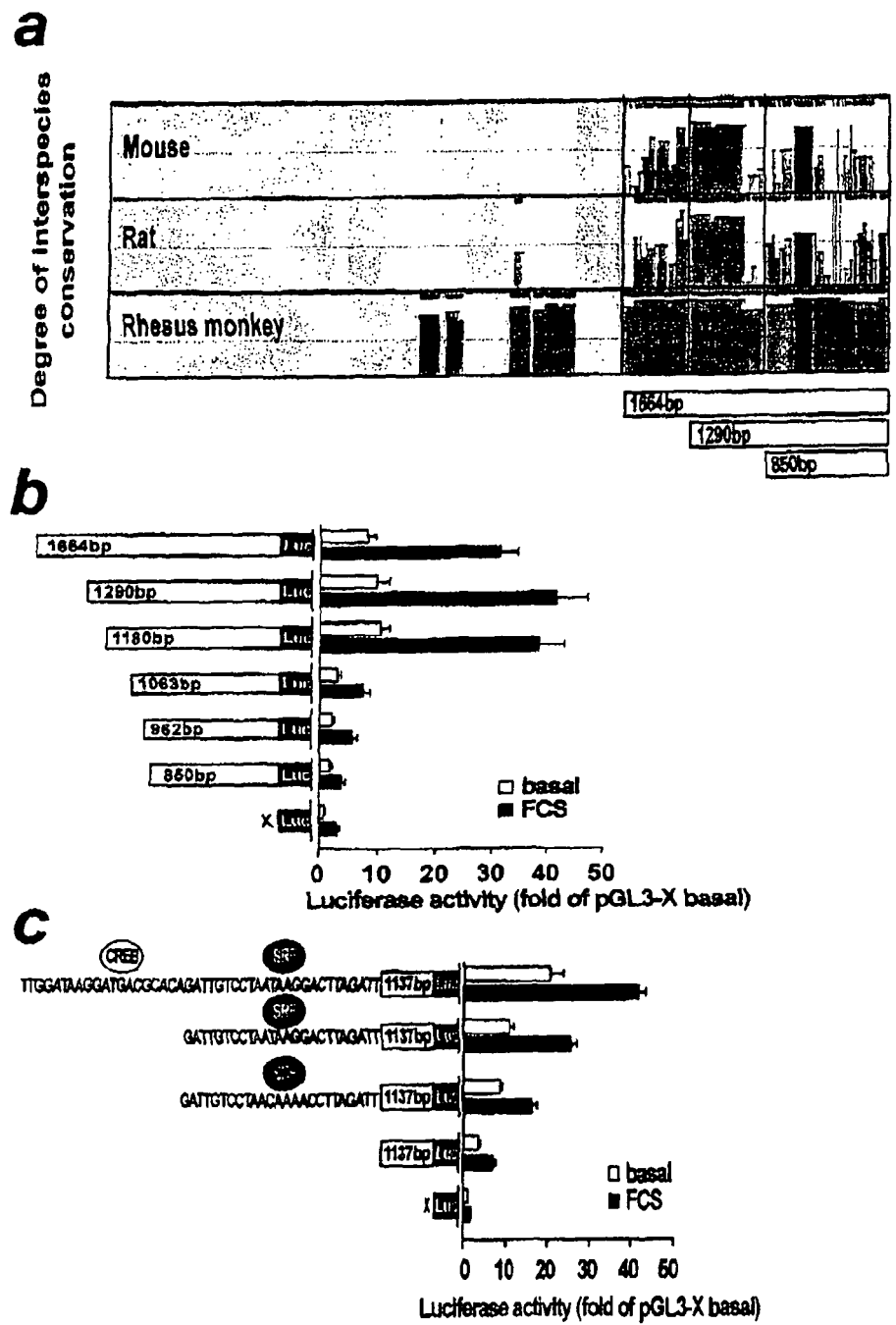
FIG. 4 Transcriptional Regulation of miR-21
(a) Sequence conservation within the miR-21-promoter regions of different species in comparison to the human miR-21-promoter. Bars indicate degree of conservation.
(b) Luciferase activity of human miR-21-promoter constructs. Progressive shortening of the native promoter leads to identification of a 117 by region that is responsible for expression of miR-21. n=3.
(c) Luciferase data of human miR-21-promoter constructs after deletion/mutation of individual transcription factor binding sites. n=3.
Figure 5:
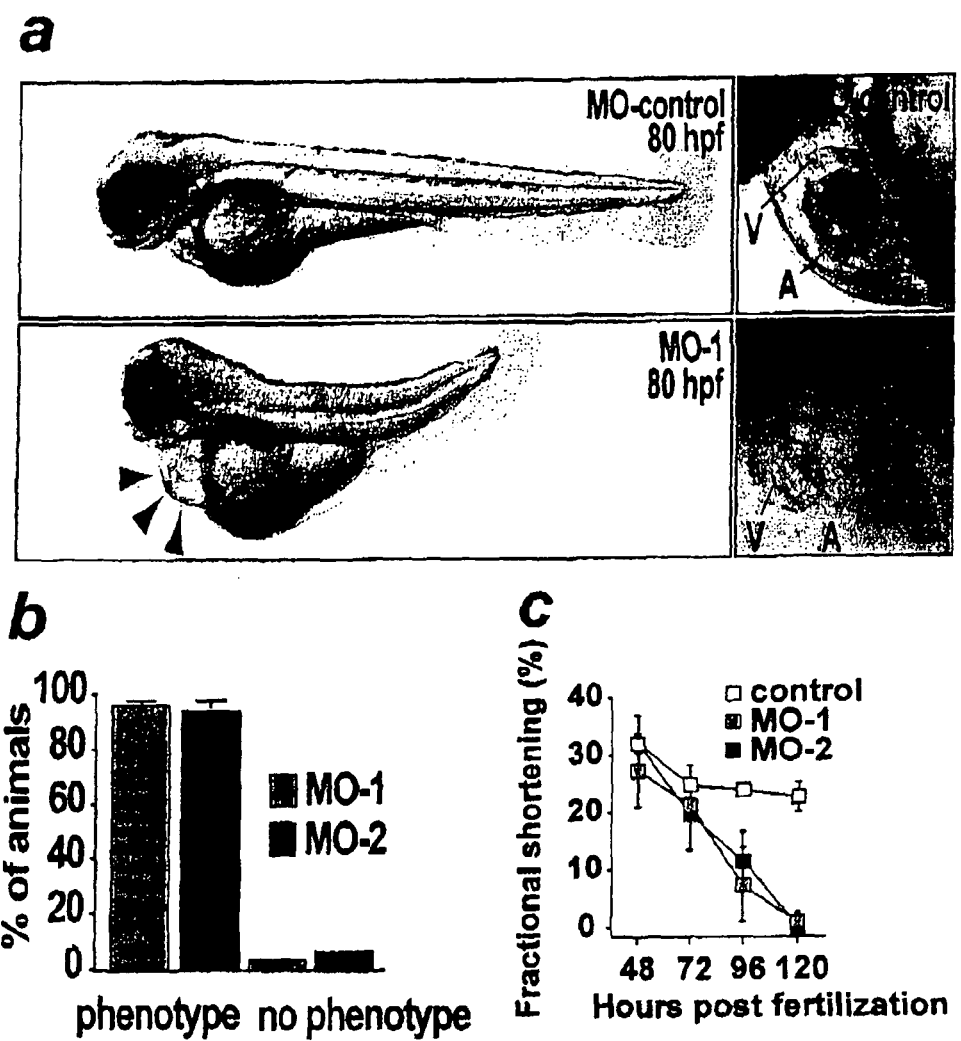
FIG. 5 Knockdown of the Ubiquitously expressed miR-21 Induces a Cardiac Phenotype in Zebrafish
(a) Left Lateral view of MO-control embryos and miR-21 morphants at 80 hpf. A, atrium; V, ventricle; dark arrows highlight pericardial edema.
Right Upper Control-morpholino (MO-control) injected hearts display normal heart morphology at 80 hours post fertilization (hpf). The hearts are looped, endocardial and myocardial layers are well developed and the ventricle (V) and atrium (A) is separated by the atrio-ventricular (AV)-ring. Lower miR-21 morphants (MO-1 injected) develop pericardial edema due to loss of ventricular contractility and display shortened tails, whereas the development of other organ systems proceeds normally.
(b) Inhibition of miR-21 function by two different morpholino-modified antisense oligonucleotides (MO-1, n=496 and MO-2, n=460) leads to identical phenotypes in >90% of the injected embryos. Data are from 3 independent injections per group.
(c) Myocardial function displayed as fractional shortening (FS) of the ventricular chamber of MO-control (n=6) and miR-21 morphants injected by two different morpholinos (MO-1, n=8 and MO-2, n=8) at 48, 72, 96 and 120 hpf. Ventricular FS of miR-21 morphant ventricles severely decreases over time.

Microarray analysis in a transgenic mouse model of cardiac failure (heart-restricted overexpression of the β1-adrenergic receptor (Engelhardt et al., 1999)) revealed progressive de-regulation of the cardiac microRNA expression signature with increasing severity of the disease (FIG. 1 a). While miR-21 expression was modest in normal myocardium, this microRNA was among the strongest regulated microRNAs in the failing heart. In fact, in mice with end-stage heart failure, miR-21 was the single strongest upregulated microRNA (FIG. 1 a). Quantitative Northern blot analysis confirmed upregulation of miR-21 in the mouse and further revealed a marked upregulation in human heart failure (FIG. 1 b, c). Increased expression of the miR-21 precursor as assessed by Northern blotting suggested a transcriptional mechanism. Thus, the human miR-21 promoter was studied in more detail. A miR-21 promoter region was identified and is highly conserved in several species (FIG. 4 a). Studies on human miR-21 expression (FIG. 4 a-c) confirmed its transcriptional regulation by two transcription factors, calcium/cAMP response element protein (CREB) and serum response factor (SRF), which are classically activated during the cardiac stress response. Deletion of CREB and mutation of the SRF binding sites in the miR-21 promoter resulted in markedly decreased miR-21 expression in response to serum stimulation, indicating a major role for these two transcription factors in miR-21 regulation (FIG. 4 c). An essential role for miR-21 in cardiac morphology and function was detected by a morpholino-based approach in a biased screen to knock down several ubiquitously expressed microRNAs in zebrafish. Knockdown of miR-21 led to a dramatic impairment of cardiac structure and function (FIG. 5). More than 95% of injected animals displayed massive pericardial effusions (FIG. 5 a, inset and b) and impaired ventricular function as determined by video microscopy (FIG. 5 c).

Figure 6:
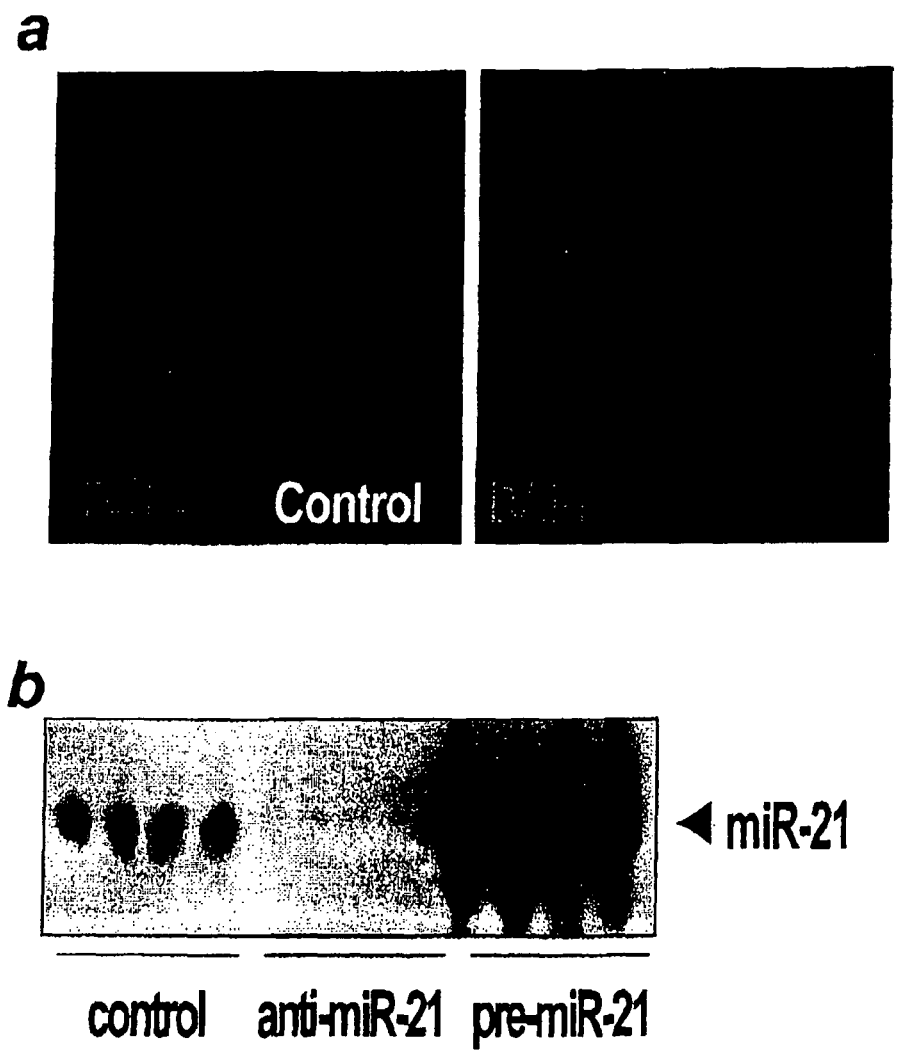
FIG. 6 Transfection Efficacy in Cultured Cardiomyocytes
(a) Cultured neonatal cardiomyocytes were transfected with Cy-3 labeled miR-21 (50 nM, 72 h, Ambion, USA) and stained with DAPI (right). For comparison cultured cardiomyocytes were stained with DAPI alone (left).
(b) Northern blot analysis of miR-21 expression in cultured cardiomyocytes after transfection with scrambled-microRNA (control-pre-miR, 50 nM, 72 h), a miR-21 inhibitor (anti-miR-21, 50 nM, 72 h), or synthetic miR-21 (pre-miR-21, 50 nM, 72 h)
All error bars indicate SEM; n=3-6 for a) and b).

To study these essential functions of miR-21 in the mammalian heart in further detail, the inventors modulated miR-21 expression in isolated cardiomyocytes. The inventors transfected synthetic miR-21-precursors as well as antisense miR-21-inhibitors, routinely achieving >95% transfection efficiency of oligonucleotide delivery (FIG. 6 a). Overexpression of miR-21 led to a robust enhancement of mature miR-21, while inhibition of miR-21 completely suppressed endogenous miR-21 expression as determined by Northern blot analysis (FIG. 6 b). However, neither enhancement nor suppression of miR-21 levels in cardiomyocytes significantly affected the morphology, size or number of primary rat cardiomyocytes under resting conditions or under conditions of cardiomyocyte hypertrophy (FIG. 1 d). Cardiomyocyte-specific miR-21 transgenic mice overexpressing miR-21 25-fold relative to wildtype littermates displayed no obvious cardiac phenotype with intact structure of the left ventricular myocardium and absence of interstitial fibrosis (FIG. 1 e, bottom). Contrary to the substantially increased miR-21 expression in the failing heart, these data show that manipulation of miR-21 expression levels in isolated cardiomyocytes and cardiomyocyte-specific miR-21 transgenic mice models fails to corroborate a significant function of miR-21 in the heart as indicated by the observed effects in zebrafish and the substantially increased miR-21 expression in the failing heart. Therefore, the inventors next explored a potential role of miR-21 in a non-cardiomyocyte cell type, e.g. cardiac fibroblasts. Using in situ hybridization, weak miR-21 signals were detected in normal myocardium, whereas in failing myocardium the hybridization signal was greatly enhanced. At high magnification, the hybridization signal was restricted primarily to small interstitial cells, presumably cardiac fibroblasts. Using a pre-plating procedure, the inventors fractionated neonatal rat hearts into a cardiomyocyte and fibroblast fraction. Indeed, the inventors detected endogenous miR-21 expression primarily in cardiac fibroblasts (FIG. 1 f).

Example 2 miR-21 Derepresses Cardiac Fibroblast ERK-Signaling

MiR-21 expression is selectively increased in various human cancers (Lu et al., 2005; Iorio et al., 2005) and was shown to contribute to tumor growth and spread by diverse mechanisms in different cells. Since miR-21 appears to target distinct mRNAs in a cell type-specific manner, the inventors decided to investigate potential heart specific miR-21 targets. Using a bioinformatic approach the inventors screened several microRNA databases for potential miR-21 targets with 3' UTR-comprising seed sequences and matching flanking nucleotides and focused this analysis on candidates with reported cardiac expression. A summary is depicted in Table 1 below.

TABLE 1

| gene symbol | gene name | cardiac expression (ID Reference) | number of conserved species (miRBase) | Predicted target (miRBase) | Predicted target (PicTar) | Seed match for miR-21 (Target Scan) |
|---|---|---|---|---|---|---|
| Spry1 | sprouty homolog 1 | 15306693 | 7 | yes | yes | 8mer |
| Tgfbi | transforming growth factor, beta induced | 10913330 | 7 | yes | yes | 8mer |
| Krit1 | KRIT1, ankyrin repeat containing | 16455310 | 7 | yes | yes | 7mer |
| Pitx2 | paired-like homeodomain transcription factor 2 | 16836994 | 7 | yes | yes | 7mer |
| Fasl | Fas ligand (TNF superfamily, member 6) | 16698421 | 7 | yes | yes | 7mer |
| Nfib | nuclear facor I/B | 9056636 | 7 | yes | no | 7mer |
| Lnx1 | ligand of numb-protein X1 | 17118964 | 7 | yes | no | 7mer |
| Rtn4 | reticulon 4 | 16202479 | 8 | yes | no | 7mer |

Figure 2:
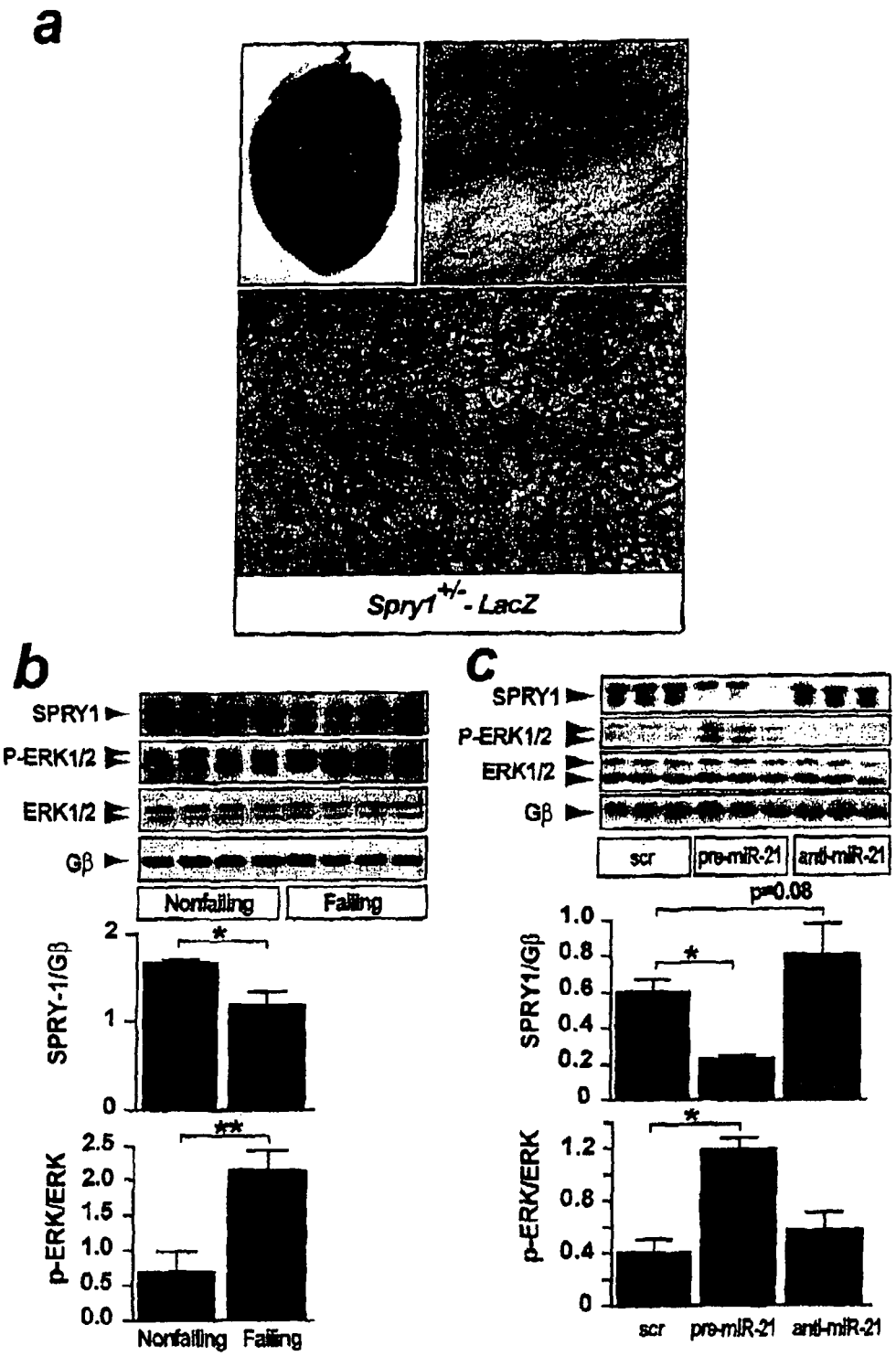
FIG. 2 Inhibition of Sprouty1 through miR-21 derepresses ERK-Signaling and Enhances Fibroblast Survival
(a) Hearts from Spry1LacZ+/− mice were stained with X-gal. Macroscopic (upper) and microscopic (lower) analysis shows detection of LacZ in cardiac fibroblasts. Short black bar represents 100 μm. Big black bar represents 10 μm
(b, c) Upper Detection of SPRY1, ERK1/2 and phospho-ERK1/2 in failing human left ventricles (b) and after transfection of co-cultured cardiomyocytes and fibroblasts with scrambled-microRNA (Pre-miR™ negative Control #2, 50 nM, 72 h), synthetic miR-21 (pre-miR-21, 50 nM, 72 h) or a miR-21 inhibitor (anti-miR-21, 50 nM, 72 h). Lower Quantitative analysis of Western blotting results.
(d) Upper Determination of SPRY1, ERK1/2, phospho-ERK1/2 after siRNA-mediated knockdown of SPRY1 (150 nM, 72 h) or treatment with scrambled siRNA (150 nM, 72 h) of the co-cultured cardiac cells. Lower Quantitative analysis of Western blotting results.
(e) Upper FACS analysis of annexin V-positive cardiac fibroblasts after treatment with scrambled-microRNA (control-pre-miR, 100 nM, 72 h), synthetic miR-21 (pre-miR-21, 100 nM, 72 h), miR-21 antagonists (anti-miR-21, 100 nM, 72 h) or respective controls (100 nM, 72 h). Lower Quantitative analysis of annexin V-positive cells after respective treatments.
(f) Upper FGF2 concentration in supernatants of cultured cardiac fibroblasts after treatment with scrambled-microRNA (control pre-miR, 100 nM, 72 h), synthetic miR-21 (pre-miR-21, 100 nM, 72 h) or miR-21 antagonists (anti-miR-21, 100 nM, 72 h) or (lower) after siRNA-mediated knockdown of SPRY1 (150 nM, 72 h) or treatment with scrambled siRNA (150 nM, 72 h) All error bars indicate SEM. n=3-6 for a-f.
Figure 2:
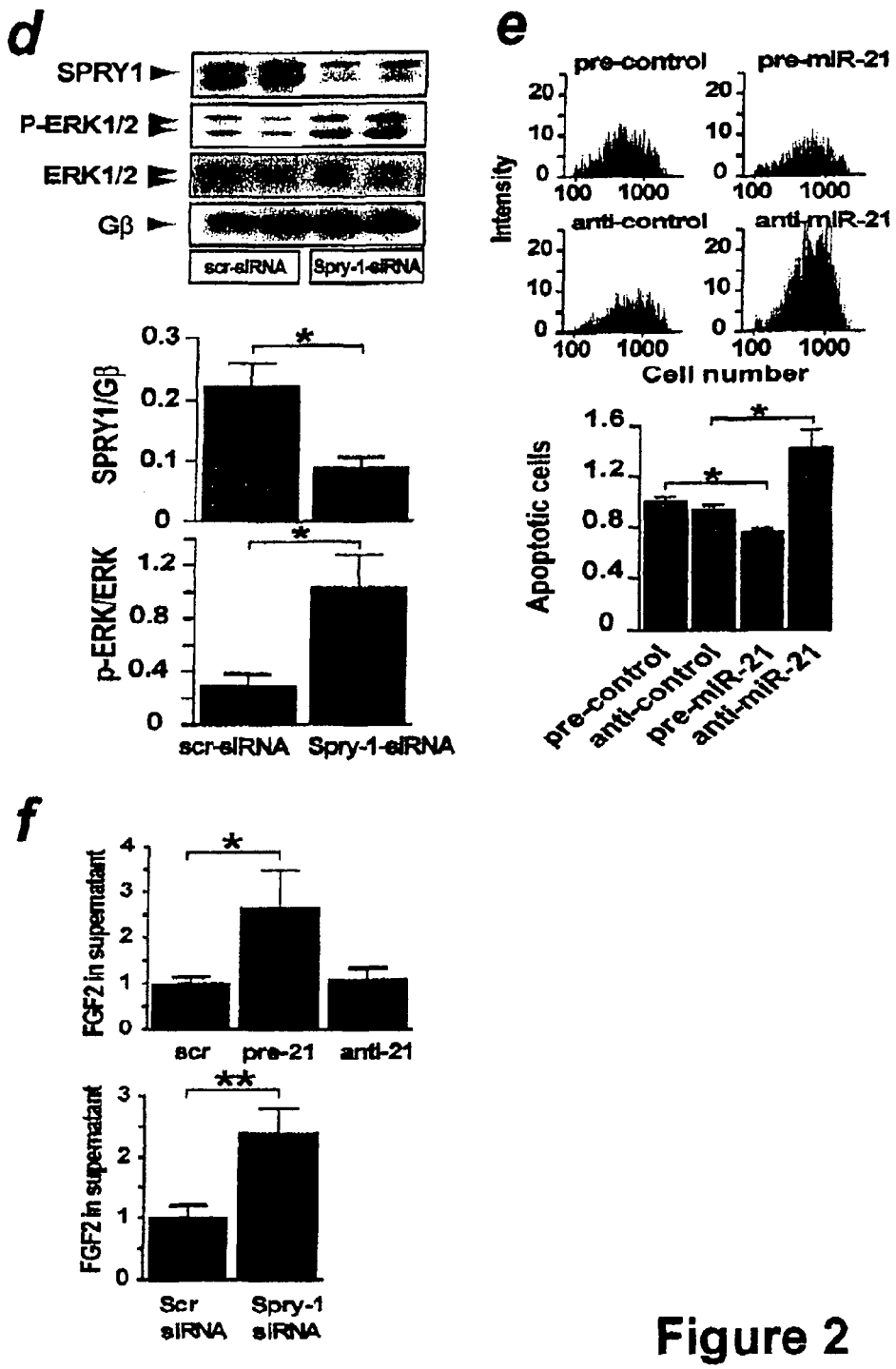
Figure 7:
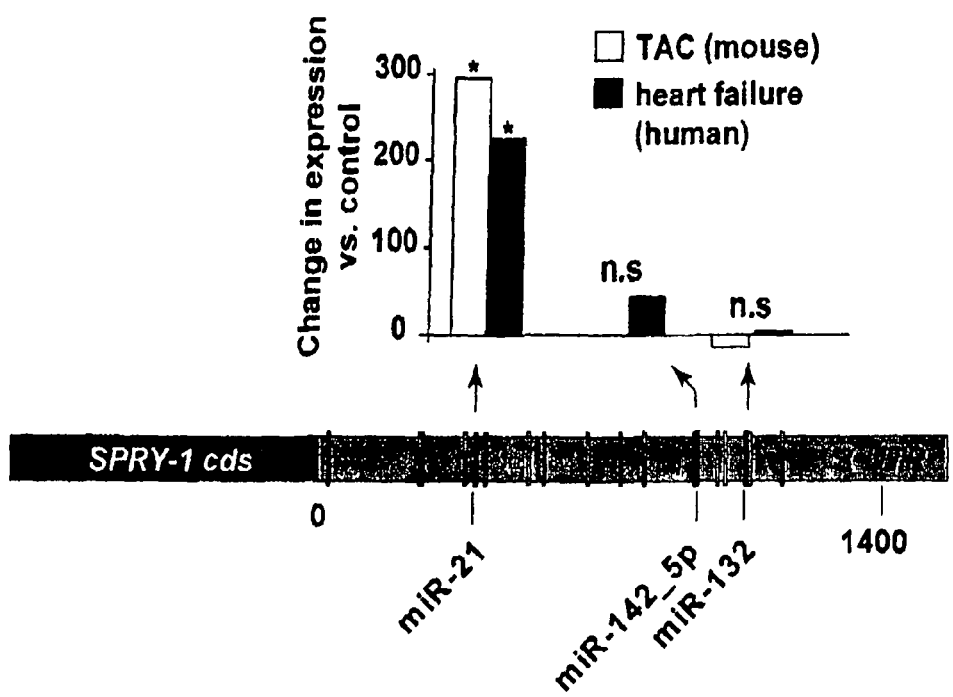
FIG. 7 MicroRNA-Binding Sites within the 3'UTR of the Spry1 Gene
Upper Change in expression of various microRNAs with binding sites within the 3'UTR of the Spry1 gene.
Lower microRNAs with binding sites within the 3'UTR analyzed by microRNA microarray are presented in grey. Cds=coding sequence
FIG. 8 miR-21 Real-Time PCR Expression Data
In addition to determination by Northern blotting, expression of miR-21 was analyzed by real-time-PCR in left ventricular tissue of mice after sham-operation, sham+antagomir-21 treatment, TAC and TAC+antagomir-21 treatment (left), as well as in hearts from wildtype mice and miR-21 transgenic mice (right). n=4-6 per group.

A screen for theoretical miR-21 targets revealed 22 known potential target genes, of which 8 were previously shown to be expressed within cardiac tissue. Combination of three different target prediction tools identified Spry1 (sprouty1) as a highly likely candidate. Sprouty1 (SPRY1), a known inhibitor of the Ras/MEK/ERK-pathway (Hanafusa et al., 2002, Casci et al., 1999) emerged as a potential target due to its high score and significant expression level in the heart (Table 1). The 3'UTR of the Spry1 mRNA contains several predicted microRNA binding sites, of which only one corresponds to a microRNA highly upregulated during cardiac disease (miR-21, see FIG. 7). To determine the cell type in which Spry1 is expressed, the inventors employed an allele of Spry1, in which the lacZ gene replaces part of the Spry1 coding sequence. Assays for lacZ expression showed prominent staining in the adult mouse heart (FIG. 2 a). Higher magnification identified a spotted pattern of Spry1 expression originating from interstitial fibroblasts (FIG. 2 a, lower panel). Thus, both miR-21 and its putative target, Spry1, are co-expressed in cardiac fibroblasts, and not in the cardiomyocyte fraction. In accordance with these observations, no detectable downregulation of SPRY1 expression was found in transgenic mice overexpressing miR-21 in a cardiomyocyte-specific manner. In addition, cardiac CREB, the transcriptional activator of miR-21 expression (FIG. 4) is localized exclusively in fibroblasts. The inventors then tested the relevance of these findings to human disease. Indeed, analysis of left ventricular cardiac tissue samples from patients with end-stage heart failure due to idiopathic dilated cardiomyopathy demonstrated increased miR-21 expression (FIG. 1c) and significant repression of SPRY1 protein expression (FIG. 2 b). These findings were accompanied by activation of ERK-MAPkinase, as evidenced by an increased phospho-ERK/ERK ratio (FIG. 2 b).

MiR-21 functions were then characterized in co-cultures of interstitial fibroblasts and cardiomyocytes to mimic the composition of intact cardiac tissue. The inventors assessed miR-21 function by transfection of synthetic miR-21 precursor molecules or inhibitors. Increasing miR-21 induced a strong repression of SPRY1 protein expression and increased ERK-MAPkinase activation (FIG. 2 c). SiRNA-mediated Spry1 silencing likewise resulted in ERK-MAPkinase activation (FIG. 2 d). The inventors next evaluated whether miR-21-mediated derepression of fibroblast ERK-MAPkinase signaling would suffice to affect fibroblast survival. In agreement with a potential role of ERK-MAPkinase signaling in myocardial fibrosis, enhancement of miR-21 levels promoted cardiac fibroblast survival, whereas suppression of endogenous miR-21 induced apoptotic cell death (FIG. 2 e). The inventors also found miR-21-based regulation of SPRY1 expression to be critical for the secretory function of cardiac fibroblasts, as both overexpression of miR-21 as well as siRNA-mediated silencing of SPRY1 expression significantly augmented secretion of fibroblast growth factor 2 (FGF2) into the supernatant (FIG. 2 f). This study thus delineated a novel signaling paradigm in the failing heart, where re-expression of miR-21 during cardiac disease augments ERK-MAPkinase activity through inhibition of SPRY1. In the mammalian heart, this mechanism may regulate fibroblast survival and thereby critically govern the extent of interstitial fibrosis and cardiac remodeling.

Example 3

Therapeutic Silencing of miR-21 In Vivo

To evaluate the function of miR-21 in vivo, in a normal setting and in heart failure, miR-21 activity was inhibited using modified oligonucleotide complementary to miR-21 (miR-21 antagonist). A pressure overload-induced hypertrophy mouse model in was used as a model for human heart failure. In this model a reproducible cardiac stress response is achieved through transverse aortic constriction (TAC). This model highly resembles the failing human heart due to its matching pattern of both microRNA and mRNA changes in global expression profiles (Thum et al. 2007).

Figure 3:
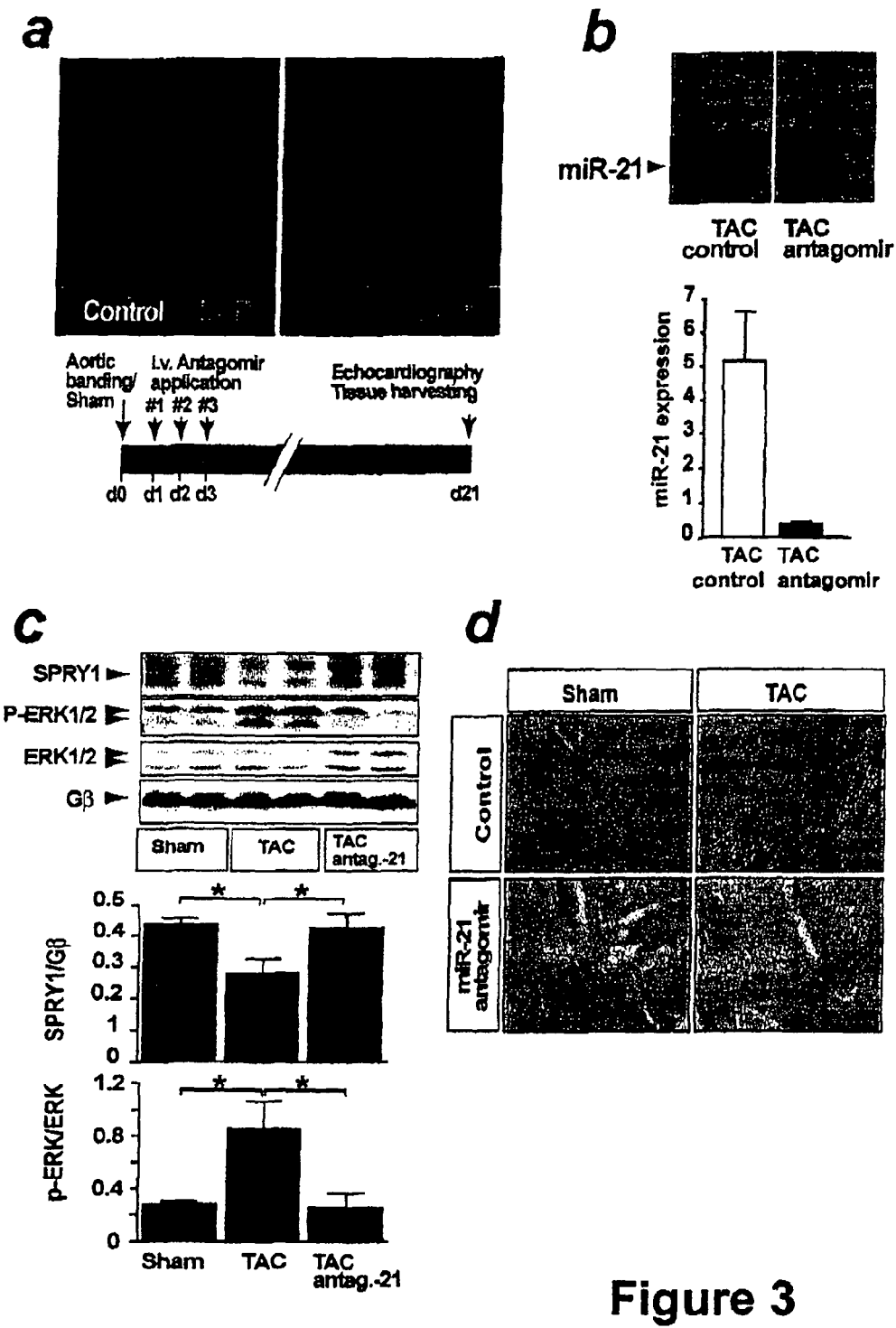
FIG. 3 Therapeutic Silencing of miR-21 In Vivo Prevents Cardiac Fibrosis and Heart Failure
(a) Upper Fluorescence microscopic detection of Cy3 and DAPI staining in left ventricular heart tissue after injection of Cy3-labeled modified oligonucleotide via the jugular vein. Controls received PBS injections. Lower Mice subjected to transaortic constriction (TAC) or sham operation were injected with control (PBS, 200 µl) or antagomir-21 (200 µl; 80 mg/kg/d) 24 h post-operation for consecutive three days.
(b) Upper Northern blot analysis of miR-21 expression in untreated (control) and antagomir-21 treated mice after TAC. Lower Quantitative analysis of cardiac miR-21 expression.
(c) Upper Western blot analysis of SPRY1, ERK1/2 and phospho-ERK1/2 in mice after sham-operation or after TAC treated with either control or antagomir-21. Expression of G beta was shown as a housekeeping control. Lower Quantitative analysis of Western blot results.
(d) Cardiac sections after Sirius red staining for detection of myocardial fibrosis in control- and antagomir-21 treated mice.
(e) Quantitative analysis of myocardial fibrosis (left) and heart/body weight (right) in control- and antagomir-21 treated mice.
(f) Upper Global transcriptome analysis of the mouse genome in heart tissue of mice after sham-operation or after TAC treated with control or antagomir-21. Red (green) boxes show significantly (p<0.05) induced (repressed) genes. Lower Normalization of upregulated genes coding for proteins involved in myocardial fibrosis after TAC by antagomir-21 treatment.
(g) Echocardiographic analyses. LVD, left ventricular diameter; FS, fractional shortening.
(h) Proposed mechanism underlying the derepression of cardiac ERK signaling through miR-21-mediated inhibition of SPRY1. All error bars indicate SEM, n=3-6 for a-g.
Figure 3:
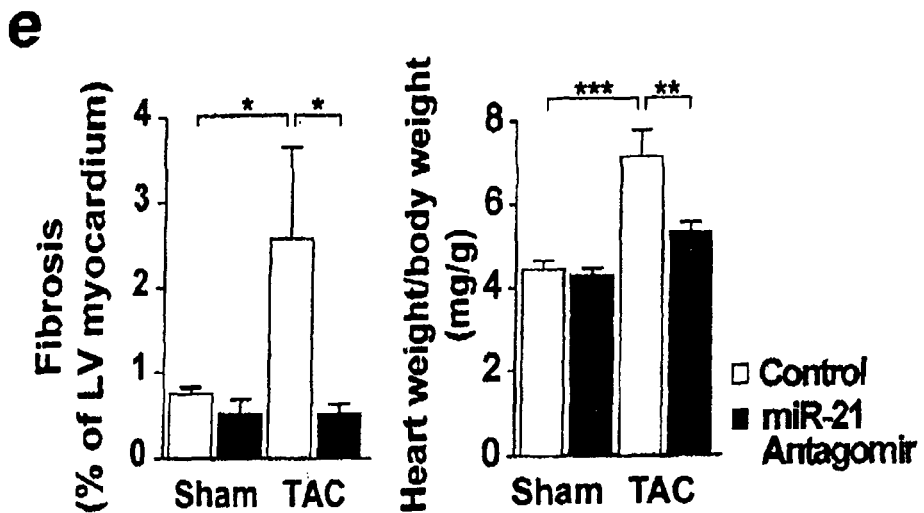
Figure 3:
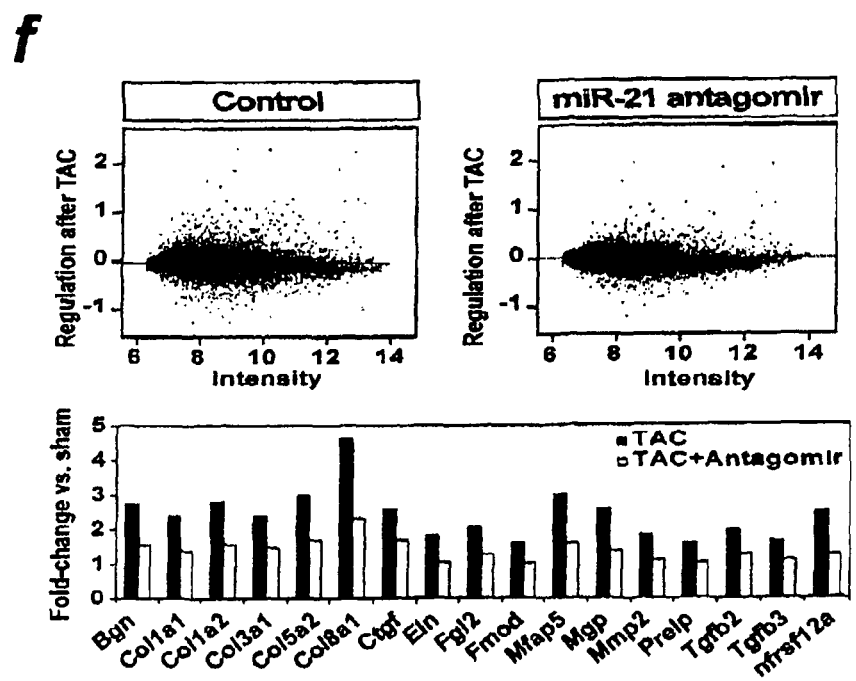
Figure 3:
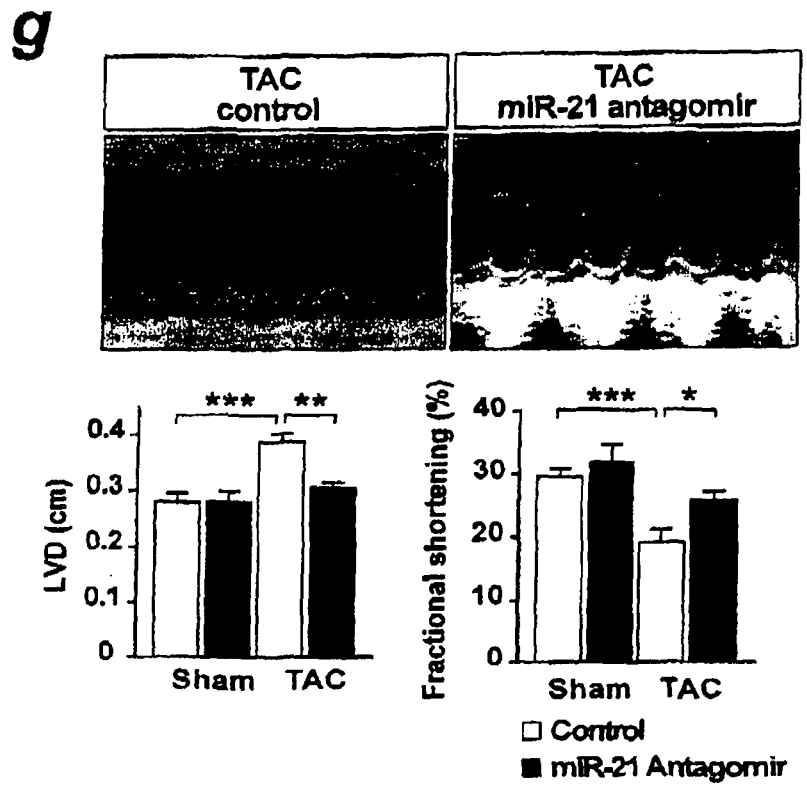
Figure 3:
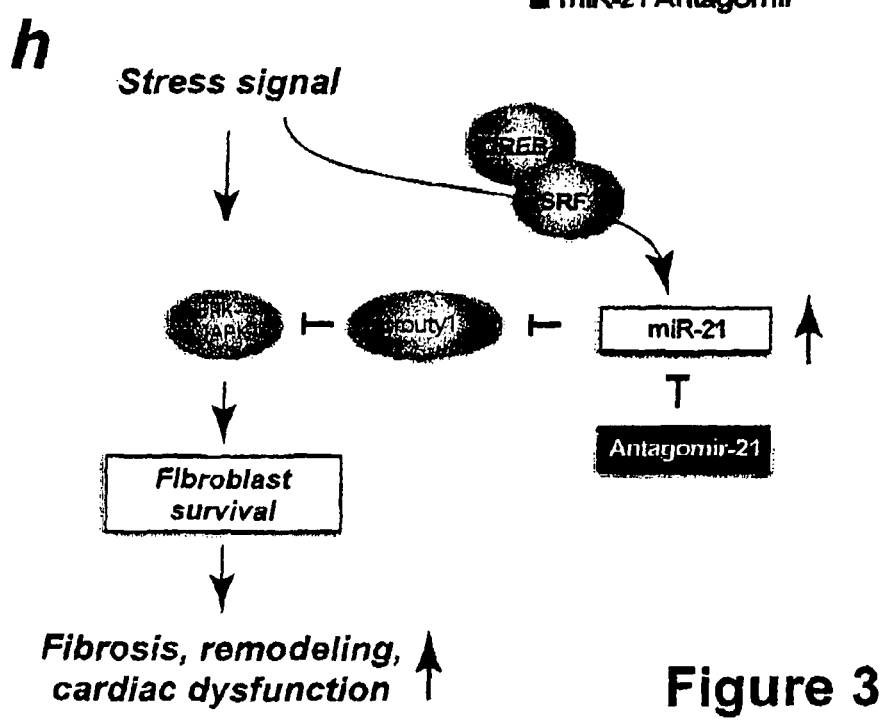
Figure 8:
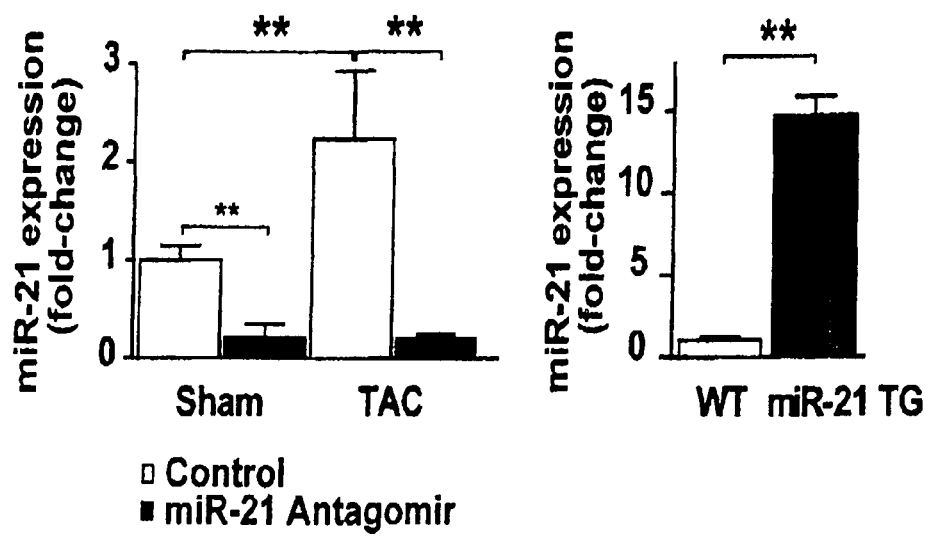

To determine the localization of antagomir-21 within the heart, a Cy-3-labeled antagomir-21 was injected intravenously via a jugular vein catheter. Strong staining throughout the left ventricular myocardium was observed (FIG. 3 a), indicating that modified oligonucleotides complementary to miR-21 achieve distribution to cardiac tissue. The miR-21 antagonist comprised 2'-O-methyl sugars at each nucleoside, two phosphorothioate internucleoside linkages at the 5'-most end of the oligonucleotide, three phosphorothioate internucleoside linkages at the 3'-most end of the oligonucleotide, and a cholesterol linked through a hydroxyprolinol linker. miR-21 antagonists had the nucleobase sequence of SEQ ID NO: 1 or SEQ ID NO: 12. Untreated (sham) or TAC-operated mice were treated with antagomir-21 or a control oligonucleotide at doses of 80 mg/kg for three consecutive days. Treatment with antagomir-21 strongly repressed elevated cardiac miR-21 expression for up to three weeks as determined in Northern blots (FIG. 3 b) and real-time PCR analysis (FIG. 8). This treatment completely reversed TAC-induced downregulation of SPRY1 and ERK-MAPkinase activation during pressure overload to levels observed in sham-operated mice (FIG. 3 c). Interstitial fibrosis and heart weight were significantly increased three weeks after TAC in untreated mice, but were strongly attenuated by antagomir-21 treatment (FIGS. 3 d, e). Indeed, collagen content of the myocardium was essentially normalized by antagomir-21 treatment. Further, where heart weight doubled three weeks after TAC, antagomir-21 treatment prevented hypertrophy. In sham-operated mice, treatment with antagomir-21 did not result in significant changes in cardiac weight or interstitial fibrosis, indicating no discernable effect of miR-21 antagonism on the normal heart or overt cardiotoxicity of antagomir-21 treatment. After TAC operation and antagomir-21 treatment, global transcriptome analysis revealed normalization of various deregulated genes (FIG. 3 f). Specifically, genes highly upregulated during cardiac fibrosis such as collagen 1α1, collagen 3α1, biglycan, fibromodulin or connective tissue growth factor were reduced after specific inhibition of miR-21 by 42%, 39%, 44%, 38% and 37%, respectively (FIG. 3 f lower panel). In further studies, cardiac function was assessed by echocardiography. Left ventricular end-diastolic diameters increased significantly three weeks after TAC and fractional shortening was impaired (FIG. 3 g), as is commonly observed in human heart failure. When compared with controls, antagomir-21 treatment prevented left ventricular dilatation and normalized parameters of fractional shortening essentially to levels observed in sham-operated animals (FIG. 3 g). Similar results were obtained with antagomir-21 treatment in an isoproterenol-induced cardiac disease model.

An additional experiment was performed, in which mice were subject to pressure overload of the left ventricle for three weeks before treatment with antagomir-21. During this period the animals displayed significant left ventricular hypertrophy, fibrosis and impaired cardiac function. After this three week time period, mice were treated with antagomir-21 and observed for an additional three weeks. Whereas animals treated with control displayed progressive impairment of left ventricular function as well as interstitial fibrosis and cardiac hypertrophy, animals treated with antagomir-21 showed significant attenuation of the impairment of cardiac function as well as regression of cardiac hypertrophy and fibrosis.

These data demonstrate a critical role for fibroblast-derived miR-21 and SPRY1 in the heart. Abnormal expression of miR-21 in cardiac fibroblasts inhibits SPRY1 protein expression, resulting in augmentation of ERK-MAP kinase activity. In turn, this enhances cardiac fibroblast survival and thereby the interstitial fibrosis and cardiac remodeling that is characteristic of the failing heart. This model (summarized in FIG. 3 h) assigns a primary role to cardiac fibroblast activation in myocardial disease. Antagonizing miR-21 in the murine model of heart disease prevented structural and function deterioration. Accordingly, the present invention provides methods for the treatment of fibrosis, comprising administering a modified oligonucleotide complementary to miR-21. The present invention further provides methods for the treatment of fibrosis related to cardiac disease, comprising administering a modified oligonucleotide complementary to miR-21.

Example 4 miR-21 Regulation of the Extracellular Signal-Regulated Kinase MAPK Pathway

Malignant transformation of normal to cancer cells requires the acquisition of several oncogenic traits such as uncontrolled cell division, resistance to programmed cell death (apoptosis), invasion and angiogenesis. Genetic alterations often result in constitutive activation of common downstream signal transduction pathways such as the mitogen activated protein (MAP) kinase cascade involving c-RAF-1, MEK-1, ERK 1/2, p38 and JNK and others. Mitogen-activated protein kinase (MAPK) cascades are key signaling pathways involved in the regulation of normal cell proliferation, survival and differentiation. Aberrant regulation of MAPK cascades contribute to cancer and other human diseases. In particular, the extracellular signal-regulated kinase (ERK) MAPK pathway has been the subject of intense research leading to the development of pharmacologic inhibitors for the treatment of cancer. In normal cells, it is well established that the activation of the kinase ERK 1/2 is regulated by receptor tyrosine kinases such as EGF-receptors and platelet-derived growth factor receptors (PDGFRs) via activation of Ras, which in turn activates the RAF-1/MEK-I/ERK 1/2 cascade. Because this signal transduction pathway is hyperactivated in many human cancers, inhibitors of receptor tyrosine kinases, Ras, c-RAF-1 and MEK-1 have all been developed and are at various stages of development. The treatment of cancer may therefore be possible by administering an effective amount of an inhibitor of the RAF-1/MEK-I/P-ERK 1/2 pathway.

Sprouty (SPRY) is a family of intracellular proteins that are endogenous regulators of receptor tyrosine kinase pathways such as the Ras/MAP kinase pathway. Mammalian species express four isoforms of Sprouty, which act as inhibitors of growth factor-induced cellular differentiation, migration, and proliferation. The inventors identified sprouty-1 to inhibit ERK phosphorylation which may result in modulation of tumor formation. The inventors suggest that upregulation of miR-21 in many human cancers inhibits sprouty-1 thus activating ERK to result in enhanced tumor formation and progression. Antagonism of miR-21 (e.g. by an antagomir-21) is therefore able to prevent and/or attenuate tumor formation and/or progression.

Example 5

Experimental Procedures

Expression Analyses (MicroRNA Array, Affymetrix Genechip Analysis, Northern Blotting, Real-Time PCR)

MicroRNA (Castoldi et al., 2007) and global mRNA expression profiles were generated from RNA preparations from murine left ventricular myocardium. Deregulated microRNAs were confirmed by Northern blotting and stem-loop specific real-time PCR. For both oligonucleotide arrays and spotted microRNA arrays, data analysis was done with the use of R packages from the Bioconductor project (www.bioconductor.org) as previously described (Thum et al., 2007).

miR-21 Promoter Analysis 24 hours after isolation, cells were transfected with 1 ug of reporter plasmid using an established liposomal transfection method (Lipofectamine, Invitrogen, USA). After 12 hours medium was changed to FCS-free medium. 24 hours later cells were treated either with 5% FCS for 8 hours whereas the other group was cultured without FCS. Luciferase activity was measured in cell lysates using the Dual Luciferase Kit (Promega, Germany) according to the manufacturer's recommendation.

Cardiomyocyte Isolation, Culture and Transfection Experiments

Neonatal cardiomyocytes were isolated as described previously (Merkle et al., 2007). Cardiomyocyte size was determined from digitally recorded images using the AxioVision LE 4.1 software package (Carl Zeiss Vision GmbH, Jena, Germany). Cardiomyocyte cultures were transfected with precursor and inhibitors of miR-21 (Ambion, USA) or siRNA against sprouty1 (Promega, Germany). Using appropriate culture conditions the inventors also performed experiments with cardiac fibroblasts and fibroblast/cardiomyocyte co-cultures.

Zebrafish Maintenance, Microinjection of Morpholino Antisense Oligonucleotides and Determination of Cardiac Function A standard morpholino-modified oligonucleotide was directed against the mature dre-miR-21 (MO-1=5'-GCCAA-CACCAGTCTGATAAGCTA-3') and also a multi-blocking Morpholino-modified oligonucleotide was used to interfere with multiple steps in miR-21 processing and function (MO-2=5"-TGTAACAGCCAACACCAGTCTGATAAGCTAT-3'). A standard control oligonucleotide (MO-control) (GENETOOLS, LLC) was injected at the same concentration as a negative control. Morpholinos were microinjected into one-cell stage wild-type zebrafish embryos and overall morphology and especially heart function was evaluated at several time points during development. Pictures and movies were recorded and ventricular fractional shortening was measured 48, 72, 80, 96 and 120 hours post fertilization (hpf) essentially as described (Rottbauer et al., 2005).

Mouse Models of Cardiac Hypertrophy and Failure

Transaortic constriction was performed by routine methods. Beta1-adrenergic receptor transgenic mice (line TG4) have been described in detail previously (Engelhardt et al., 1999).

Human Heart Samples

The inventors examined cardiac tissue from patients undergoing heart transplantation because of end-stage heart failure due to dilatative cardiomyopathy and, for comparison, healthy adult heart samples. Immediately after explantation, tissue pieces were removed from the left ventricles, and excised tissue was shock frozen in liquid nitrogen and stored at −80° C. until analysis.

microRNA Target Prediction Methods

The microRNA databases and target prediction tools miR-Base (http://microrna.sanger.ac.uk/), PicTar (http://pictar.bio.nyu.edu/) and TargetScan (http://www.targetscan.org/index.html) were used to identify potential microRNA targets.

Western Blotting and Analysis of Cardiac Fibrosis

Protein lysates from explanted hearts or co-cultures were prepared as described (Buitrago et al., 2005) and expression of Spry1, ERK1/2, phosphoERK1/2 and G beta detected as described herein. For analysis of morphology and fibrosis hearts were fixed in 4% formalin and embedded in paraffin. Tissue sections (5 um) from the LV were stained with hematoxylin and eosin or picrosirius red. Picrosirius red sections were examined using a Nikon ECLIPSE 50i microscope equipped with filters to provide circularly polarized illumination. Tissue images were obtained with a 20× objective lens, recorded on a cooled digital camera (DS-5Mc, Nikon), and analyzed using SigmaScan Pro 5.0 image analysis software (SPSS Inc., USA). Collagen content was calculated as a percentage of the area of each image (expressed in pixels).

αMHC-miR-21 Transgenic Mice

Transgenic mice overexpressing miR-21 were generated by pronuclear injection of fertilized oocytes from FVB/N mice with a transgene construct containing the mature miR-21 sequence, flanked by 154 by upstream and 136 by downstream of the native precursor sequence under the control of the murine α-myosin heavy chain (αMHC) promoter.

X-Gal Staining of Myocardium from Spry-lacZ Mice

Hearts were collected from Spry1-lacZ+/− mice and fixed for 2 h in PBS containing 2% formaldehyde and 0.05% glutaraldehyde. Subsequently, the hearts were rinsed 4 times for 30 min in 0.01% Na-desoxycholate, 0.02% Nonidet P-40, 2 mM MgCl2 and 2 mM EGTA in PBS. For the detection of the β-galactosidase activity the hearts were incubated in rinsing solution containing 0.5 mg/ml X-gal, 10 mM $K_3Fe(CN)_6$, and 10 mM, $K_4Fe(CN)_6$ at 37° C. For whole mount analysis the hearts were transferred to 30% glycerol and digital images were taken using a Nikon Digi-tal Camera DXM1200F and ACT-1 software. For histological analysis the hearts were dehydrated in isopropanol, cleared in xylene and transferred to paraffin. 10 um paraffin sections were generated using standard protocols and documented.

Injection and Detection of Modified Oligonucleotides

A jugular vein catheter was permanently inserted in male C57/Bl6 mice (10-12 weeks old) before TAC procedure. 24 h post-TAC 80 mg/kg/d of modified oligonucleotide was injected daily for 3 days through the jugular vein catheter. As a positive control for effective delivery (Cy3-labeled modified oligonucleotide) was injected at 80 mg/kg once into the catheter and the heart was removed 3 h later, fixed and Cy3 staining observed by fluorescence microscopy.

Fibroblast Apoptosis and FGF2 Production

After treatment with miR-21 precursors, inhibitors or respective controls, Annexin V-positive fibroblasts were measured by FACS analysis (Annexin-V-FLUOS kit, Roche Diagnostics GmbH, Mannheim, Germany). Enzyme-linked immunosorbent assay (ELISA) was performed to quantify FGF2 concentrations in supernatants of miR-21 modulated cardiac fibroblasts. The FGF2 assay was carried out using the Quantikine FGF Basic Immunoassay kit (R&D Systems, Minneapolis, USA) according to the manufacturer's specifications.

Statistical Analysis

Average data are presented as mean±SEM. Statistical analysis was carried out using the Prism software (GraphPad, San Diego, Calif.) or StatView (SAS Institute Inc., Cary, USA) package. ANOVA followed by Bonferroni's test and Student's t-test were used as appropriate. Differences were considered significant when $P<0.05$ and are indicated by an asterisk. * indicates $p<0.05$,  indicates $p<0.01$, * indicates $p<0.005$.

RNA Isolation, Real-Time RT-PCR and Northern Blotting

For extraction of total RNA from frozen tissues or cell cultures the RNeasy Mini Kit (Qiagen, Hilden, Germany) was used according to the manufacturer's instructions. mRNAs were isolated by TRIZOL (Invitrogen, Karlsruhe, Germany) or a miRNA Isolation Kit (mirVana™, Ambion, USA). The integrity of the isolated RNA was verified with denaturing agarose gel electrophoresis or capillary electrophoresis (Bioanalyzer 2100; Agilent) as described (Thum and Borlak 2004). For real-time PCR the inventors employed an iCycler iQ™ Real-Time PCR Detection System (BioRad, Germany).

The inventors used target-specific stem loop structure and reverse transcription primer, and after reverse transcription used specific TaqMan hybridization probes to quantify miR-21 expression (TaqMan miR-21 MicroRNA Assay, Applied Biosystems, Foster City, USA). The small RNA molecule U6B small nuclear (RNU6B) was amplified as a control (TaqMan MicroRNA Assay Controls, Applied Biosystems, Foster City, USA). All miRNA samples were derived from isolations comprising the same total RNA concentration.

For Northern blot analysis, 3 μg of total RNA were loaded onto 15% acrylamide, 6 M urea, and TBE gels alongside an appropriate DNA marker. Following electrophoresis, RNA was transferred to a nylon membrane (Qiabrane Nylon, Qiagen) using semidry transfer. Membranes were then prehybridized for 1 h at 65° C. in hybridization buffer (UL-TRAhyb-Oligo Hybridization Buffer, Ambion, USA). LNA oligonucleotides (miRCURY LNA Array detection probes; Exiqon) that were previously labeled with T4 kinase (Exiqon) and 32P-ATP were then added to the buffer and membranes were hybridized over night at 42° C. Subsequently, the blot was washed three times at room temperature for 3 minutes (in 0.2×SSC), followed by one time at 42° C. for 15 minutes. Afterwards membranes were exposed on a phosphoimager.

microRNA Expression Analyses

For microarray microRNA expression analyses the inventors separately purified microRNAs using the flashPAGE Fractionator system (Ambion, USA). microRNA obtained from 8 μg total RNA was labeled with the dye Cy3 (Molecular Probes, Carlsbad, Calif.) by use of the mirVana microRNA Labeling Kit (Ambion, USA) according to the manufacturer's recommendations. Each sample was hybridized to a separate array. MicroRNA microarray hybridization, microRNA purification and enrichment, labeling and microarray hybridization procedures were performed according to the Ambion mirVana manuals (www.ambion.com/techlib/prot/) or as described 2. Data acquisition was done with the use of ScanAlyze Software (Eisen-Lab, Lawrence Berkeley National Lab (LBNL), Berkeley, USA). Alternatively, 5 μg total RNA was labeled with a Cy3-conjugated RNA linker (Dharmacon, USA) and hybridized to a microarray platform for genome-wide profiling of miRNAs [miChip; capture probes immobilized on the array correspond to (211 human, 51 murine) unique human miRNAs as deposited in miRbase version 6.1]. Hybridization signal intensities were acquired using the Axon scanner (4000B, Molecular Dynamics) with identical photomultiplier settings. Further analyses were performed using Genepix 6 (Molecular Dynamics) and Excel softwares. MiR-21 expression was validated by specific TaqMan RT-PCR analyses and Northern Blot analysis.

Global Transcriptome Analysis

For transcriptome analyses, reverse transcription, second-strand synthesis, and cleanup of double-stranded cDNA were performed according to the Affymetrix protocols (One-Cycle cDNA synthesis Kit, Affymetrix, USA) starting from 2 μg of total RNA (n=4 control hearts after sham-surgery, n=4 left ventricles after TAC and placebo treatment; n=4 left ventricles after TAC and miR-21 antagonist treatment). Synthesis of biotin-labeled cRNA was performed with the use of the IVT Labeling Kit (Affymetrix, USA). cRNA concentration was determined and the distribution of cRNA fragment sizes was checked by gel electrophoresis. 15 μg of fragmented cRNA was used for hybridization on the mouse genome 430 2.0 GeneChip (Affymetrix, USA). Data analysis from array studies R packages from the Bioconductor project (www.bioconductor.org) were used. Resulting signal intensities were normalized by variance stabilization. Quality of all data sets was tested and statistical analysis was performed using the limma (Linear Models for Microarray Analysis) package to select for differentially expressed genes.

Cardiac Co-Culture Experiments and microRNA/siRNA Transfection Procedures

Cardiomyocytes from neonatal rats were isolated and cultivated using as described (Merckle et al., 2007). For analysis of miR-21 modulation on cardiomyocyte size, pure cardiomyocyte cultures were used by addition of pre-plating steps to exclude major non-cardiomyocyte (e.g. fibroblasts) contaminations. More than 95% of cultured cardiomyocytes stained positive for actinin, demonstrating high purity of cell cultures. Scrambled-miR (prenegative control #2, Ambion; 50 nmol/L, 72 hours), miR-21 precursor molecules (pre-MiR, Ambion; 50 nmol/L, 72 hours) or miR-21 antagonists (anti-miR, Ambion; 50 nmol/L, 72 hours) were transfected by a liposomal-based method (Lipofectamine, Invitrogen, USA; see 6 for details). Cardiomyocytes were cultured with low FCS (0.1%, control condition) or 48 h with high FCS (5.0%) to induce cardiomyocyte hypertrophy. For determination of cell size, surface area of neonatal cardiomyocytes (72 hours after transfection) was calculated in a 96-well plate format (seeding density 40.000 cells/well) with the use of the Axio-Vison Rel 4.4 package (Carl Zeiss GmbH, Jena, Germany). Data are expressed as mean±SEM.

To mimic cardiac in vivo conditions the inventors used a co-culture system of cardiomyocytes and cardiac fibroblasts by ignoring the preplating step as described above. Here, the inventors studied in detail expression of Spry-1 and Erk activation after transfection of scrambled-miR (50 nmol/L, 72 hours), miR-21 precursor molecules (50 nmol/L, 72 hours) or miR-21 antagonists (50 nmol/L, 72 hours). In separate experiments scrambled siRNA or a specific siRNA cocktail against Spry1 (three different microRNAs, 16.7 nmol/L each) were transfected to the co-culture. Transfection" efficiency was monitored by realtime-PCR measurements (TaqMan MicroRNA Assays, Applied Biosystems) and Northern blotting.

microRNA Target Prediction Tools

The miRanda algorithm (Griffiths-Jones et al., 2006) was used to scan for potential miR-21 binding sites in 3' UTR sequences of the human and murine genome. Subsequently, Karlin-Altschul normalization was performed (miRBase Targets version 4.0; http://microrna:sanger.ac.uk/targets/v4/). In detail, the inventors used the miRBase data base (Version 4, Sanger Institute; USA) and sorted potential miR-21 targets by using the algorithms "high number of conserved species; >6"), "low p-value; <0.001" and high miRBase score; >15. This procedure revealed 22 known genes to be potential miR-21 targets, of which 8 were previously shown to be expressed within heart tissue based on their GEO-expression profile (http://www.ncbi.nlm.nih.gov/geo/) (see Table 1). 5 genes were additionally predicted as miR-21 targets using the PicTar miRNA data base 9 (Krek et al., 2005) (http://pictar.bio.nyu.edu/). Using the TargetScan miRNA target prediction software (Whitehead Institute for Biomedical Research, USA, Release 4.0; July 2007; http://www.targetscan.org/) the inventors identified targets with conserved sites with 8-mer seed matches for miR-21 only for two targets. Spry1 was then studied in more detail.

Western Blotting

Protein lysates from explanted hearts or cultured fibroblasts/cardiomyocytes were prepared as described (Buitrago et al., 2005). Extracts (20-50 µg protein per lane) were mixed with sample loading buffer and under reducing conditions separated on 10% SDS—polyacrylamide gels. Proteins were electrotransferred onto PVDF membrane (Immun-Blot®, Bio-Rad). The bands were detected using a chemiluminescence assay (ECL Plus, Amersham). The inventors used primary antibodies against sprouty-1 (Santa Cruz, sc-30048, dilution 1:250-1:500), Erk1/2 (Cell Signaling, #9102, dilution 1:1000); phospho-Erk1/2 (Cell Signaling, #9101, dilution 1:1000) and G-β (Santa Cruz Biotechnology, sc-378, dilution 1:1000), as well as appropriate secondary antibodies (Anti-mouse-HRP (Cell Signaling, #7076, dilution 1:10000; Anti-rabbit-HRP (Cell Signaling, #7074, dilution 1:10000).

In Vivo TAC Model and Modified Oligonucleotide Administration

The inventors used male C57BL/6 mice (10-12 weeks old, 25 g) from Charles River Laboratories (Sulzfeld, Germany). Transaortic constriction (TAC) was created using a 7-0 suture tied twice around the aorta and a 27-gauge needle. The needle was then gently retracted, yielding an about 80% constriction of the aorta. During the same operations, a jugular vein catheter was implanted by standard surgical procedures. The sequences were: antagomir-21, 5'-oUsoCsoAoAoCoAoUo-CoAoGoUoCoUoGoUoAoAoGsoCsoUsoAs-Chol-3'. All nucleotides used in synthesis are 2'-OMe-modified (Subscript V). Subscript 's' represents a phosphorothioate linkage; "Cy3" indicates Cy3 dye label at the 5' end of the oligo; "Chol" represents cholesterol linked through a hydroxyprolinol linkage. Treatment started 24 h post TAC and animals received PBS or miR-21 antagonist injections via an implanted jugular vein catheter (three consecutive days, jugular vein injections of PBS or miR-21 antagonist at doses of 80 mg per kg body weight in 0.2 ml per injection. As a positive control for effective cardiac delivery Cy-3-labeled modified oligonucleotide (antagomir-181a) (80 mg/kg) was injected into the jugular vein catheter and the heart was removed 3 h later, fixed and Cy3 staining observed by fluorescence microscopy.

Cardiac Functional Analysis

After 3 weeks of TAC, mice were anesthetized with isoflurane, and cardiac dimensions and function were analyzed by 15-MHz pulse-wave Doppler echocardiography. Then the heart was removed, weighted after removal of atria and subjected to further analysis. Echocardiographic studies were performed under light anesthesia with spontaneous respiration using isoflurane. Two independent ultrasonographer experienced in rodent imaging and blinded to the experimental groups performed the echocardiography, operating a Toshiba Power Vision 6000 with a 15 MHz transducer. 2D left-parasternal short-axis views at the level of the papillary muscles were recorded. Correct probe placement was judged by the round appearance of the left ventricular (LV) cavity after angulation and craniocaudal transducer movements. LV end-diastolic area was calculated by manual tracings of the endocardial border followed by planimetry with the Nice software package (Toshiba Medical Systems). Simultaneous transversal M-mode tracings were recorded with the cursor placed in the middle of the LV cavity. Fractional shortening was calculated as described (Collins et al., 2001).

Detection of Cardiac Fibrosis

Mouse hearts were fixed in 4% buffered formalin and embedded in paraffin. 5 µm picrosirius red sections were examined using a Nikon ECLIPSE 50i microscope equipped with filters to provide circularly polarized illumination (Whittaker et al., 1994). The lower filter was placed above the microscope's field iris diaphragm ring, while the upper filter was constructed from a combination of a quarter-wave plate placed below a linear polarizer aligned such that its transmission axis was at 45° to the fast axis of the wave plate. These two filters were crossed, that is aligned so that the background in the field of view was as dark as possible. Tissue images were obtained with a 20× objective lens, recorded on a cooled digital camera (DS-5Mc, Nikon), and analyzed using SigmaScan Pro 5.0 image analysis software (SPSS Inc., USA).

Precisely, original (circularly polarized) images, were resolved each into its cyan, yellow, magenta and black components (using the automated function CYMK provided by the image-analysis). The black component was subtracted from the polarized image. Prior to subtraction the black component was adequately brightness adjusted to ensure the elimination of the interstitial space and non-collagen elements but not of the thinnest collagen fibers (confirmed by inspection). Then the subtracted image was subjected to a final color separation into its hue, saturation, value (HSV) components using the automated function HSV provided by the image software. A histogram of hue frequency was obtained from the resolved 8-bit hue image, which contains 256 colors. The following hue definitions were used: red 2-9 and 230-256, orange 10-38, yellow 39-51, green 52-128. The hue range 129-229 consists of interstitial space and non-birefringent tissue elements. The number of pixels within hue red, orange, yellow and green ranges was determined, and expressed as a percentage of the total number of collagen pixels, which in turn was expressed as a percentage of the total number of pixels in the image.

Fibroblast Apoptosis and FGF-2 Production

Cardiac fibroblasts obtained by the preplating step during cardiomyocyte isolation were cultured until sub-confluence. Cell purity was >95% based on staining with the fibroblast marker anti-rat prolyl-4-hydroxylase (Acris Antibodies, AF5110-1; data not shown). After treatment with miR-21 precursors, inhibitors or respective controls (see above), Annexin V-positive fibroblasts were measured by FACS analysis (Annexin-VFLUOS kit, Roche Diagnostics GmbH, Mannheim, Germany). Enzyme-linked immunosorbent assay (ELISA) was performed to quantify FGF-2 concentrations in supernatants of miR-21 modulated cardiac fibroblasts. FGF-2-determination was carried out using the Quantikine FGF Basic Immunoassay kit (R&D Systems, Minneapolis, USA) according to the manufacturer's specifications.

References

Ambros, V. The functions of animal microRNAs. *Nature* 431, 350-355 (2004).

Buitrago, M. et al. The transcriptional repressor Nab1 is a specific regulator of pathological cardiac hypertrophy. *Nat Med* 11, 837-844 (2005).

Care, A. et al. MicroRNA-133 controls cardiac hypertrophy. *Nat Med* 13, 613-618 (2007).

Casci, T., Vinos, J. & Freeman, M. Sprouty, an Intracellular Inhibitor of Ras Signaling. *Cell* 96, 655-665 (1999).

Castoldi, M. et al. A sensitive array for microRNA expression profiling (miChip) based on locked nucleic acids (LNA). *RNA* 12, 913-920 (2006).

Collins, K. A. et al. Accuracy of echocardiographic estimates of left ventricular mass in mice. *Am J Physiol Heart Circ Physiol* 280, H1954-H1962 (2001).

Engelhardt, S., Hein, L., Wiesmann, F. & Lohse, M. J. Progressive hypertrophy and heart failure in beta 1-adrenergic receptor transgenic mice. *Proceedings of the National Academy of Sciences* 96, 7059-7064 (1999).

Griffiths-Jones, S., Grocock, R. J., van Dongen, S., Bateman, A. & Enright, A. J. miRBase: microRNA sequences, targets and gene nomenclature. *Nucleic Acids Research* 34, D140-D144 (2006).

Hanafusa, H., Torii, S., Yasunaga, T. & Nishida, E. Sprouty1 and Sprouty2 provide a control mechanism for the Ras/MAPK signalling pathway. *Nat Cell Biol* 4, 850-858 (2002).

Iorio, M. V. et al. MicroRNA Gene Expression Deregulation in Human Breast Cancer. *Cancer Res* 65, 7065-7070 (2005).

Kruetzfeldt J, et al. Silencing of microRNAs in vivo with 'antagomirs'. *Nature* 438, 685-689 (2005).

Lu, J. et al., MicroRNA expression profiles classify human cancers. *Nature* 435, 834-838 (2005).

Merkle, S. et al. A Role for Caspase-1 in Heart Failure. *Circ Res* 100, 645-653 (2007).

Mi, S. et al. MicroRNA expression signatures accurately discriminate acute lymphoblastic leukemia from acute myeloid leukemia. *Proceedings of the National Academy of Sciences* 104, 19971-19976 (2007).

Rottbauer, W. et al. VEGF-PLC{gamma}1 pathway controls cardiac contractility in the embryonic heart. *Genes Dev.* 19, 1624-1634 (2005).

Thum, T. & Borlak, J. Mechanistic role of cytochrome P450 monooxygenases in oxidized low-density lipoprotein-induced vascular injury: therapy through LOX-1 receptor antagonism? *Circ Res* 94, e1-13 (2004).

Thum, T. et al. MicroRNAs in the Human Heart: A Clue to Fetal Gene Reprogramming in Heart Failure. *Circulation* 116, 258-267 (2007).

Yang, B. et al. The muscle-specific microRNA miR-1 regulates cardiac arrhythmogenic potential by targeting GJA1 and KCNJ2. *Nat Med* 13, 486-491 (2007).

What is claimed:

1. A method comprising:
   a) administering to a subject having fibrosis or suspected of having fibrosis a compound comprising a modified oligonucleotide consisting of 12 to 30 linked nucleosides, where the modified oligonucleotide comprises a nucleobase sequence complementary to miR-21; and
   b) administering to the subject one or more additional pharmaceutical agents.

2. The method of claim 1, wherein the one or more additional pharmaceutical agents are selected from a diuretic, a vasodilator, an angiotensin II converting enzyme (ACE) inhibitor, an angiotensin II receptor blocker (ARB), a calcium channel blocker, hydralazine, and a beta blocker.

3. The method of claim 2, wherein the method comprises administering to the subject an ACE inhibitor selected from captopril, enalapril, lisinopril, benzzepril, quinapril, fosinopril, and ramipril.

4. The method of claim 2, wherein the method comprises administering to the subject an ARB selected from candesartan, irbesartan, olmesartan, losartan, valsaratan, telmisartan, and eprosartan.

5. The method of claim 1 wherein the fibrosis is liver fibrosis, cardiac fibrosis, kidney fibrosis, lung fibrosis, skin fibrosis, age-related fibrosis, or spleen fibrosis.

6. The method of claim 1 wherein the subject has at least one disease or condition chosen from a cardiac disease or condition, a liver disease or condition, a lung disease or condition, and a kidney disease or condition.

7. The method of claim 1, wherein administering the compound comprising a modified oligonucleotide:
   a) ameliorates the fibrosis;
   b) slows further progression of the fibrosis;
   c) halts further progression of the fibrosis; and/or
   d) reduces the fibrosis.

8. The method of claim 1 wherein the modified oligonucleotide consists of 15, 16, 17, 18, 19, 20, 21, 22, 23, or 24 linked nucleosides and the nucleobase sequence of the modified oligonucleotide has at least 15, at least 16, at least 17, at least 18, at least 19, at least 20, at least 21, or at least 22 contiguous nucleobases of the nucleobase sequence of SEQ ID NO: 12.

9. The method of claim 1, wherein the modified oligonucleotide comprises at least one modified internucleoside linkage or at least one modified sugar or at least one modified nucleobase or a combination thereof.

10. The method of claim 9, wherein the modified oligonucleotide comprises at least one modified sugar.

11. The method of claim 10, wherein each modified sugar is independently selected from a 2'-O-methoxyethyl sugar, a 2'-fluoro sugar, a 2'-O-methyl sugar, or a bicyclic sugar moiety.

12. The method of claim 9, wherein the modified oligonucleotide comprises at least one modified internucleoside linkage.

13. The method of claim 12, wherein each modified internucleoside linkage is a phosphorothioate internucleoside linkage.

14. The method of claim 9, wherein the modified oligonucleotide comprises at least one modified nucleobase.

15. The method claim 1 wherein the nucleobase sequence of the modified oligonucleotide is at least 90% complementary to the nucleobase sequence of SEQ ID NO: 1.

16. The method of claim 1, wherein the nucleobase sequence of the modified oligonucleotide is at least 95% complementary to the nucleobase sequence of SEQ ID NO: 1.

17. The method of claim 1, wherein the nucleobase sequence of the modified oligonucleotide is 100% complementary to the nucleobase sequence of SEQ ID NO: 1.

18. The method of claim 16, wherein the fibrosis is cardiac fibrosis.

19. The method of claim 16, wherein the fibrosis is liver fibrosis.

20. The method of claim 16, wherein the fibrosis is kidney fibrosis.

21. The method of claim 16, wherein the fibrosis is lung fibrosis.

* * * * *

SEQUENCE LISTING

<160> NUMBER OF SEQ ID NOS: 12

<210> SEQ ID NO 1
<211> LENGTH: 22
<212> TYPE: RNA
<213> ORGANISM: Artificial sequence
<220> FEATURE:
<223> OTHER INFORMATION: microRNA-21

<400> SEQUENCE: 1
uagcuuauca gacugauguu ga          22

<210> SEQ ID NO 2
<211> LENGTH: 45
<212> TYPE: DNA
<213> ORGANISM: Artificial sequence
<220> FEATURE:

<223> OTHER INFORMATION: promoter region of miR-21

<400> SEQUENCE: 2
ttggataagg atgacgcaca gattgtccta ataaggactt agatt        45

<210> SEQ ID NO 3
<211> LENGTH: 25
<212> TYPE: DNA
<213> ORGANISM: Artificial sequence
<220> FEATURE:
<223> OTHER INFORMATION: promoter region miR-21 deletion CREB binding
      site

<400> SEQUENCE: 3
gattgtccta ataaggactt agatt        25

<210> SEQ ID NO 4
<211> LENGTH: 25
<212> TYPE: DNA
<213> ORGANISM: Artificial sequence
<220> FEATURE:
<223> OTHER INFORMATION: promoter region miR-21 deletion of CREB binding
      site and point mutation of the SRF binding site

<400> SEQUENCE: 4
gattgtccta aacaaaactt agatt        25

<210> SEQ ID NO 5
<211> LENGTH: 23
<212> TYPE: DNA
<213> ORGANISM: Artificial sequence
<220> FEATURE:
<223> OTHER INFORMATION: morpholino antisense oligo against mature dre-
      mirR-21

<400> SEQUENCE: 5
gccaacacca gtctgataag cta        23

<210> SEQ ID NO 6
<211> LENGTH: 31
<212> TYPE: DNA
<213> ORGANISM: Artificial sequence
<220> FEATURE:
<223> OTHER INFORMATION: multiblockign morpholino antisense oligo to
      interfere with mirR-21

<400> SEQUENCE: 6
tgtaacagcc aacaccagtc tgataagcta t        31

<210> SEQ ID NO 7
<211> LENGTH: 960
<212> TYPE: DNA
<213> ORGANISM: Homo sapiens

<400> SEQUENCE: 7
atggatcccc aaaatcaaca tggcagtggc agttcgttag ttgtgatcca gcagccttct        60
ttggatagcc gtcagagatt agactatgag agagagattc agcctactgc tatttttgtcc       120 ttagaccaga tcaaggccat aagaggcagc aatgaataca cagaagggcc ttcggtggtg       180
aaaagacctg ctcctcggac agcaccaaga caagaaaagc atgaaaggac tcatgaaatc       240
ataccaatta atgtgaataa taactacgag cacagacaca caagccacct gggacatgca       300
gtactcccaa gtaatgccag gggcccccatt ttgagcagat caaccagcac tggaagtgca       360
gccagctctg ggagcaacag cagtgcctct tctgaacagg gactgttagg aaggtcacca       420

```
ccaaccagac cagtccctgg tcataggtct gaaagggcaa tccggaccca gcccaagcaa    480
ctgattgtgg atgacttgaa gggttccttg aaagaggacc tgacacagca caagttcatt    540
tgtgaacagt gtgggaagtg caagtgtgga gaatgcactg ctcccaggac cctaccatcc    600
tgtttggcct gtaaccggca gtgcctttgc tctgctgaga gcatggtgga atatggaacc    660
tgcatgtgct tagtcaaggg catcttctac cactgctcca atgacgacga agggattcc     720 tattcagata tccttgctc ctgttcacaa tcacactgct gctctagata cctgtgtatg     780
ggagccatgt ctttattttt accttgctta ctctgttatc ctcctgctaa aggatgcctg    840
aagctgtgca ggaggtgtta tgactggatc catcgcccag ggtgcagatg taagaactcc    900
aacactgtct attgtaagct ggagagctgc ccctcccggg gtcagggtaa accatcatga    960
```

<210> SEQ ID NO 8
<211> LENGTH: 319
<212> TYPE: PRT
<213> ORGANISM: Homo sapiens

<400> SEQUENCE: 8

```
Met Asp Pro Gln Asn Gln His Gly Ser Gly Ser Ser Leu Val Val Ile
1               5                   10                  15

Gln Gln Pro Ser Leu Asp Ser Arg Gln Arg Leu Asp Tyr Glu Arg Glu
            20                  25                  30

Ile Gln Pro Thr Ala Ile Leu Ser Leu Asp Gln Ile Lys Ala Ile Arg
        35                  40                  45

Gly Ser Asn Glu Tyr Thr Glu Gly Pro Ser Val Val Lys Arg Pro Ala
    50                  55                  60

Pro Arg Thr Ala Pro Arg Gln Glu Lys His Glu Arg Thr His Glu Ile
65                  70                  75                  80

Ile Pro Ile Asn Val Asn Asn Tyr Glu His Arg His Thr Ser His
                85                  90                  95

Leu Gly His Ala Val Leu Pro Ser Asn Ala Arg Gly Pro Ile Leu Ser
            100                 105                 110

Arg Ser Thr Ser Thr Gly Ser Ala Ala Ser Ser Gly Ser Asn Ser Ser
        115                 120                 125

Ala Ser Ser Glu Gln Gly Leu Leu Gly Arg Ser Pro Pro Thr Arg Pro
    130                 135                 140

Val Pro Gly His Arg Ser Glu Arg Ala Ile Arg Thr Gln Pro Lys Gln
145                 150                 155                 160

Leu Ile Val Asp Asp Leu Lys Gly Ser Leu Lys Glu Asp Leu Thr Gln
                165                 170                 175

His Lys Phe Ile Cys Glu Gln Cys Gly Lys Cys Lys Cys Gly Glu Cys
            180                 185                 190

Thr Ala Pro Arg Thr Leu Pro Ser Cys Leu Ala Cys Asn Arg Gln Cys
        195                 200                 205

Leu Cys Ser Ala Glu Ser Met Val Glu Tyr Gly Thr Cys Met Cys Leu
    210                 215                 220

Val Lys Gly Ile Phe Tyr His Cys Ser Asn Asp Asp Glu Gly Asp Ser
225                 230                 235                 240

Tyr Ser Asp Asn Pro Cys Ser Cys Ser Gln Ser His Cys Cys Ser Arg
                245                 250                 255

Tyr Leu Cys Met Gly Ala Met Ser Leu Phe Leu Pro Cys Leu Leu Cys
            260                 265                 270

Tyr Pro Pro Ala Lys Gly Cys Leu Lys Leu Cys Arg Arg Cys Tyr Asp
        275                 280                 285
```

```
Trp Ile His Arg Pro Gly Cys Arg Cys Lys Asn Ser Asn Thr Val Tyr
    290                 295                 300

Cys Lys Leu Glu Ser Cys Pro Ser Arg Gly Gln Gly Lys Pro Ser
305                 310                 315

<210> SEQ ID NO 9
<211> LENGTH: 21
<212> TYPE: RNA
<213> ORGANISM: Artificial sequence
<220> FEATURE:
<223> OTHER INFORMATION: antisense oligonucleotide against miR-21

<400> SEQUENCE: 9
ucaacaucag ucuguaagcu a                                                   21

<210> SEQ ID NO 10
<211> LENGTH: 22
<212> TYPE: RNA
<213> ORGANISM: Artificial sequence
<220> FEATURE:
<223> OTHER INFORMATION: antisense oligonucleotide against miR-181a

<400> SEQUENCE: 10
acucaccgac agguugaaug uu                                                  22

<210> SEQ ID NO 11
<211> LENGTH: 72
<212> TYPE: RNA
<213> ORGANISM: Artificial sequence
<220> FEATURE:
<223> OTHER INFORMATION: microRNA-21 stem-loop sequence

<400> SEQUENCE: 11
ugucggguag cuuaucagac ugauguugac uguugaaucu cauggcaaca ccagucgaug         60
ggcugucuga ca                                                             72

<210> SEQ ID NO 12
<211> LENGTH: 22
<212> TYPE: RNA
<213> ORGANISM: Artificial sequence
<220> FEATURE:
<223> OTHER INFORMATION: antisense oligonucleotide against miR-21

<400> SEQUENCE: 12
ucaacaucag ucugauaagc ua                                                  22
```